United States Patent
Yoo et al.

(10) Patent No.: US 6,323,238 B1
(45) Date of Patent: Nov. 27, 2001

(54) BENZOPYRANYL GUANIDINE DERIVATIVES, PROCESS FOR PREPARATION THEREOF, AND PHARMACEUTICAL COMPOSITIONS CONTAINING THEM

(75) Inventors: Sung-Eun Yoo, Chungchongnam-do; Kyu Yang Yi, Taejon-si; Sun Kyung Lee, Taegon-si; Nak-Jeong Kim, Taejon-si; Jee Hee Suh, Taejon-si; Young Sook Park, Chullanam-do; Sun Kyung Hwang, Pusan-si; Hwa Sup Shin, Taejon-si; Byung Ho Lee, Taejon-si; Ho Won Seo, Taejon-si; Hong Lim, Seoul; Sun-Ok Kim, Taejon-si; In Sun Cho, Taejon-si; Miae Namgoong, Taejon-si; Dongsoo Jang, Taejon-si, all of (KR)

(73) Assignee: Dongbu Hannong Chemical Co., Ltd., Seoul (KR)

( * ) Notice: Subject to any disclaimer, the term of this patent is extended or adjusted under 35 U.S.C. 154(b) by 0 days.

(21) Appl. No.: 09/693,082

(22) Filed: Oct. 20, 2000

Related U.S. Application Data

(63) Continuation-in-part of application No. 09/586,655, filed on Jun. 3, 2000.

(30) Foreign Application Priority Data

Oct. 21, 1999  (KR) .................................................. 99-45871
Oct. 13, 2000  (KR) ............................................. 2000-60467

(51) Int. Cl.$^7$ .......................... C07D 311/74; A61K 31/35
(52) U.S. Cl. ........................ 514/456; 514/449; 514/450; 514/452; 514/463; 514/475; 549/347; 549/370; 549/399; 549/404; 549/448; 549/510; 549/511
(58) Field of Search ................................. 549/404, 347, 549/370, 399, 448, 510, 511; 514/456, 449, 450, 452, 475, 463

(56) References Cited

PUBLICATIONS

Hee Kim, et al, "KR 31372, a benzopyran derivative, inhibits oxidized LDL–stimulated proliferation and migration of vascular smooth muscle cells" CA 134:188015 (2000).*

Cho, Hidetsura, et al, "Synthesis and Selective Coronary Vasodilatory Activity of 3,4–Dihydro–2,2–bis(methoxymethyl)–2H–1–benzopyran–3–ol Derivatives: Novel Potassium Channel Openers" CA 125:157769 (1996).*

Kato, Susumu, et al, "Preparation of chroman derivs. as coronary vasodilators" CA 123:285779 (1995).*

"Cadioselective Antiischemic ATP Sensitive Potassium, Channel Openers . . ", By Karnail S. Atwal et al., published by J. Med. Chem. 1995. vol. 38. pp. 1996–1973.

"Cardioselective Anti–Ischemic ATP–sensitive Potassium, Channel Openers . . . ", By Karnail S. Atwal et al., published by J. Med. Chem. 1995, vol. 38 , pp. 3236–3245.

"Cardioselective Anti–Ischemic ATP–Sensitive Potasisum Channel Openers" By Karnail S. Atwal et al., published by J. Med. Chem. 1993, vol. 36, pp. 3971–3974.

"Treatment of Myocardial Ischemia with ATP–Sensitive Potassium Channel KATP Openers", By Karnail S. Atwal et al., published by Current Pharmaceutical Design, 1996. vol. 2. pp. 585–595.

* cited by examiner

*Primary Examiner*—Amelia Owens
(74) *Attorney, Agent, or Firm*—Bachman & LaPointe, P.C.

(57) ABSTRACT

The present invention relates to novel benzopyranyl guanidine derivatives of the formula 1, process for preparation therof and pharmaceutical use of the benzopyranyl guanidine derivatives. The benzopyranyl guanidine derivatives of the present invention can be used for protecting heart, neuronal cell or brain damage, preserving organs, and also the benzopyranyl guanidine derivatives are pharmacologically useful for inhibiting NO generation, and for suppressing lipid peroxidation, angiogenesis or restenosis.

FORMULA 1

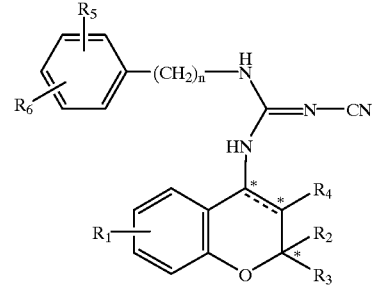

Wherein $R_1$, $R_2$, $R_3$, $R_4$, $R_5$, $R_6$, n and * are each defined in specification.

18 Claims, No Drawings

BENZOPYRANYL GUANIDINE DERIVATIVES, PROCESS FOR PREPARATION THEREOF, AND PHARMACEUTICAL COMPOSITIONS CONTAINING THEM

CROSS-REFERENCE TO RELATED APPLICATION

The instant application is a continuation-in-part of application Ser. No. 09/586,655 filed Jun. 3, 2000.

BACKGROUND OF THE INVENTION

1. Field of the Invention

The present invention relates to novel benzopyranyl guanidine derivatives of formula 1. IL also relates to process for preparing the novel compounds and pharmaceutical formulations comprising one or more of the compounds as an active ingredient.

The present invention also relates to pharmaceutical use of the benzopyranyl guanidine derivatives. In particular, the present invention is pharmacologically useful in the protection of heart, neurconsonal cell or brain injury, or preserving organs, and also pharmacologically useful for inhibition of NO generation, lipid peroxidation, angiogenesis or restenosis.

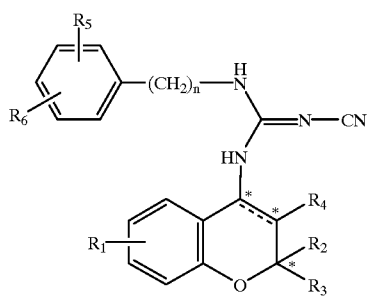

FORMULA 1

Wherein $R_1$, $R_2$, $R_3$, $R_4$, $R_5$, $R_6$, n and * are each defined in specification.

2. Description of the Prior Art

Ischemic heart diseases usually occur as a result of myocardial ischemia, when the oxygen supply is significantly decreased compared to the oxygen demand due to the imbalance between them. In most cases, a coronary artery disorder was found to be a main reason of the ischemic heart diseases. If the inner diameter of coronary artery becomes narrow, the blood supply, resulting in oxygen supply, becomes insufficient, which can cause angina pectoris, myocardial infarction, acute cardioplegia, arrhythmia, and so on (G. J. Grover, *Can. J. Physiol.* 75, 309 (1997); G. D. Lopaschuk et al., *Science & Medicine* 42 (1997)). Because ischemic heart diseases are also caused by other complex factors besides coronary artery disorders, drug therapy as well as operational method such as perculaneous transluminal coronary angioplasty (PTCA) is required for its treatment. For that purpose, several drugs are being used, including anti-thrombotic agents, arteriosclerosis curatives, especially by beta blockers, nitrate, calcium antagonists such as nifedipin, thromobolytics, aspirin, and angiotensin converting enzyme (ACE) inhibitors.

Differently from conventional potassium channel openers, the pyranyl guanidine compound (BMS-180448) represented by the following formula 2, has been reported to act selectively on ATP-sensitive potassium channels ($K_{ATP}$) located in the heart (K. S. Atwal et al., *J. Mde. Chem.* 36, 3971 (1993); K. S. Atwal et al., *J. Me. Chem.* 38, 1966 (1995)). The BMS 180448 compound was found to protect ischemic hearts without a significant lowering of blood pressure, which gives the prospects for novel drug development as a cardionprotectant.

FORMULA 2

Both global and focal ischemia initiate progressive cellular changes, which lead to ischemic brain injury (M. D. Ginsburg, *Neuros Scientist* 1, 95 (1995)). Even after blood flow is restored, oxygen can enhance the biochemical reactions that generate free radicals, which can lead to a potential for "reperconsfusion injury" to occur. In order to prevent the brain injury caused by ischemia-reperfusion, the brain must be protected during ischemic period to avoid additional injury and pathological progressive cellular to changes have to be minimized. For that purpose, neuroproteconstives such as excitatory amino acid antagonists and anti-oxidants are being used.

Damage or death of neurons is known to be a main cause for various neurological disorders such as stroke, head trauma, Alzheimer's disease, Parkinson's disease, infant asphyxia, glaucoma and daiabetic neuropathy, etc. (G. J. Zoppo et al., *Drugs* 54, 9(1997); I. Sziraki et al., *Neurosci.* 85, 110(1998)). Neurons are damaged by various consfactors and typically by increase in iron concentration, reactive oxygen species, and peroconsxidants within neurons (M. P. Mattson et al. , *Methods Cell Biol.* 46, 187 (1995); Y. Goodman et al., *Brain Res.* 706, 328 (1996)).

An increase of iron concentration in neuronal cells induces the formation of highly reactive hydroxyl radicals. An excess of oxygen free radicals facilitates lipid peroxidation, so that peroxidants are accumulated in neurons. The reactive free radicals accumulated in cells are known o be responsible for inflammatory diseases such as arthritis; atherosclerosis; cardiac infarction; and neurodegenerative disease such as dementia as well as acute and chronic injury of tissues and organs caused by ischemia-reperfusion or by endotoxins via bacterial infection.

Therefore, therapeutic approaches to minimize the damage or death of neurons have been pursued, including the inhibition of lipid peroxidation, NO formation, and reactive oxygen species induced by endotoxins. To date, antioxidants are reported to ameliorate the neuronal damage and death caused by an increase of iron concentration within neurons. Much effort has been continued to develop pharmaceutical drugs which are able to prevent neuronal damage by oxidative stress (Y. Zhang et al., *J. Cereb. Blood Flow Metab.* 13, 378 (1993)).

Infant asphyxia (IA), triggered by transient deficiency of oxygen supply during delivery, was reported to be caused by the reduction of energy production, damage of cell membrane due to oxygen free radical, release of excitatory neurotransmitters, change of intracellular ion concentrations including calcium, zinc, etc. IA is a major worldwide problem, because if IA is severe, the chances of mortality are high (around 1/3 of the cases) [C. F. Loid et. al. *Physiology and Behavior* 68; 263–269 (2000)]. In addition, it can produce long term sequela such as movement disorders, learning disabilities, epilepsy, dystonia, mental retardation, and spasticity.

Antioxidant enzymes, allopurinol, Vitamine C & E, free radical scavengers, inhibitors of excitatory neurotransmitters, calcium channel blockers such as nimodipinconsa and flunarizine, inhibitors of NO formation, hyperglycemic and hypothermic therapy may be beneficial for the protection of brain injury, but their clinical application is still limited. Thus more intensive research is required to treat infant asphyxia properly.

Glaucoma, one of the leading causes of blindness, is defined as an optic neuropathy associated with characteristic changes in optic nerve. In humans, the optic nerve consists of 1 million axons from neurons whose perikarya reside primarily in the ganglion cell layer and, to a less extent, in the inner part of the inner nuclear layer. The excavated appearance of the optic nerve head in glaucoma is thought to be caused by the death and subsequent loss of ganglion cells and their axons [N. N. Osborne, et. *Al. Survey of Ophthalmology*, 43; suppl. S102–s128 (1999)]. Neuroprotective agents in glaucoma may protect death of retinal neurons, in particular the ganglion cells, either directly or indirectly. A variety agents such as NMDA receptor antagonist, β-blockers, calcium antagonists, and antioxidants can be used to protect the death of retinal neurons induced by ischemia.

Although the pathogenesis of diabetic neuropathy has not been clearly established, two main hypotheses have been proposed for it. One is metabolic abnormalities, and the other is blood flow deficits in peripheral nerve [K. Naka et. *Al. Diabetes Research and Clinical Practice*, 30: 153–162 (1995)]. Acetyl-L-carnitine (ALC) by stimulating metabolism of lipid and improving impaired nociceptive responses of neurons, and Prosaptide by releasing neutrophic factors are in clinical trials. In addition, memantime showing good effects on vascular dementia through the regulation of NMDA receptor, is pursuing clinical trial. Then, neuroprotective agents having a variety of mechanisms of action may be developed to treat diabetic neuropathy.

The ratio of cancer in human diseases is being gradually increased. Angiogenesis, formation of new blood vessels, is recognized as the core process for growth and metastasis of solid tumors (Folkma, J. et al., *J. Biol. Chem.* 267: 10931–10934 (1992)). Angiogenesis is controlled by inducers and inhibitors of angiogenesis. When the balance between them is broken, that is, when angiogenesis inducers prevail over angiogenesis inhibitors, a large quantity of new blood vessels are formed. Angiogenesis is closely related to various physiological phenomena, such as embryonic development, wound healing, chronic inflammation, hemangiomas, diabetic retinopathy, rheumatoid arthritis, psoriasis, AIDS complications, and the growth and metastasis of malignant tumors (Forkman, J., Klagsbrun. M. *Science* 235: 442–447 (1987)). Angiogenesis includes a series of processes such as the migration, proliferation and differentiation of endothelial cells, and is an important prerequisite for the growth and metastasis of cancers. Tn detail, because the growing tumor cells require the formation of blood vessels from host cells, angiogenesis promotors derived from tumors stimulate to induce the angiogenesis into the consumor mass. Afterwards, the blood vessels formed around the malignant tumors facilitate to metastasize the tumor cells to other sites. Therefore, the inhibition of angiogenesis leads to the prevention of the growth and metastasis of cancers. As one of the important research areas for the developing of anti-cancer drugs, extensive attention is paid to the finding of angiogenesis inducers and angiogenesis inhibitors and the revealing of their working mechanisms.

Thus far, proteins such as prostamine and tumor necrotic factors, factors derived from cartilage tissues, and cortisone called angiostatic steroids and various steroid derivatives, have been found to be able to play roles as angiogenesis inhibitors. In particular, hydrocortisone exhibits antiangiogenetic activity by cotreatment with heparin (Lee, A. et al., *Science* 221: 1185–1187 (1983); Crum, R. et al., *Science* 230: 1375–1378 (1985)). However, these compounds have a potential problem to treat cancers effectively owing to their cytotoxicity.

Percutaneous coronary interventions (PCI) play an important role in the management of coronary artery stenosis, narrowing of the lumen as a result of growth of an atherosclerotic plaque in the intima (Inner coat) of the vessel, with success rate of more than 95%, but these are complicated by significant renarrowing of the artery (restenosis) in 20–50% of patients with 6 months after the intervention (Bult, H. *Tips*, 21; 274–279 (2000)). The biology of restenosis is not completely understood, but the predominant cellular mechanisms that contribute to restenosis include thrombosis, vascular smooth muscle cell migration and proliferation, and adventitious scarring. Different form atherosclerosis, restenosis is not dependent on the concentration or composition of atherogenic plasma lipids.

Finding effective therapies for restenosis has been difficult because of incomplete understanding of biology of restenosis and the lack of suitable animal models. Some drug classes, glycoprotein IIb/IIIa antagonist, antioxidant probucol, have recently demonstrated potential benefits in clinical trials (Bult, H. *Tips*, 21; 274–279 (2000)). Since angiogenesis restenosis is characterized by intensive proliferative activity, then development of drugs to reduce vascular smooth muscle cell proliferation are being pursued.

The intensive research on the development of compounds with the above-mentioned pharmacological efficacies by the inventors, found that the benzopyranyl guanidine derivatives represented by the formula 1 have superior cardioprotective and neuroprotective activity from ischemia-reperfusion and hypoxic damage. The compounds also exhibit various pharmacological efficacies, including protection of neurons, prevention of lipid peroxidation and reactive oxygen species formation, protection of ischemic retina, improvement of impaired nociceptive responses in diabetic rats, inhibition of NO formation, and suppression of angiogenesis and restenosis. Thus the compound of the present invention can be useful in the prevention and treatment of various diseases related to cardiovascular system such as cardiac infarction and congestive heart failure; stroke; neuronal damage such as infant asphyxia, glaucoma, diabetic neuropathy and head trauma; oxygen free radical-related disease such as neurodegenerative diseases and atherosclerosis; angiogenesis such as cancers and diabetic retinopathy, or restenosis, and also can be used in protecting preserving organs such as heart, kidney, liver, and tissues and protecting organs in major cardiovascular surgery.

SUMMARY OF THE INVENTION

One of the objectives of the present invention is to provide novel benzopyranyl guanidine derivatives of formula Another objective of the present invention is to provide process for the preparation of the benzopyranyl guanidine derivatives.

Further objective of the present invention is to provide pharmaceutical use of the benzopyranyl guanidine derivatives. In particular, the present invention provides the use of the benzopyranyl guanidine derivatives for the protection of heart and brain from ischemic and hypoxia injury, neuroprotection, inhibition of NO formation, lipid peroxidation and reactive oxygen species generation, or suppression of and suppression of angiogenesis and restenosis.

DETAILED DESCRIPTION OF THE INVENTION

The present invention provides benzopyranyl guanidine derivatives represented by the following formula 1 and their pharmaceutically acceptable salts.

FORMULA 1

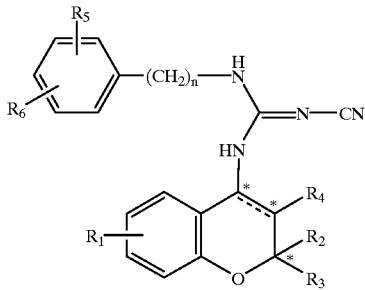

Wherein $R_1$ R represents H, halogen, $CF_3$, $NO_2$, CN, $OR^a$, $O(C=O)R^a$, $COOR^a$, $NH_2$, $NHS(O)_m R^a$, $NH(C=O)R^a$ or $S(O)_m R^a$; $R^a$ represents straight or branched alkyl group of $C_1$–$C_4$ or aryl group; and m is an integer of 0–2, $R_2$ represents straight or branched alkyl group of $C_1$–$C_4$, $R_3$ represents $CH_2OR^a$,

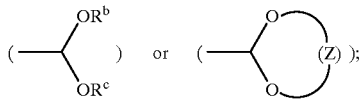

$R^a$ is defined as above; $R^b$ and $R^c$ are independent each other and represent straight or branched alkyl group of $C_1$–$C_4$, respectively; and Z represents straight or branched alkyl group of $C_1$–$C_5$;

$R_4$ represents OH, H, halogen, $ONO_2$, or $O(C=O)R^a$; and $R^a$ is defined as above; $R_5$ and $R_6$ are independent each other and represent H, halogen, straight or branched alkyl group of $C_1$–$C_3$, $OR^a$, $CX_3$, $NO_2$, $CO_2R^a$, —$(C=O)R^a$ or $SO_3R^a$; $R^a$ is defined above; and X represents halogen, and n is an integer of 0–2.

And * represents the chiral center.

In the formula 1, more preferably $R_1$ represents $NO_2$, CN, $NH_2$ or $S(O)_m R^a$; $R^a$ represents straight or branched alkyl group of $C_1$–$C_2$, or aryl group; and m is an integer of 0–2, $R_2$ represents $CH_3$, $R_3$ represents

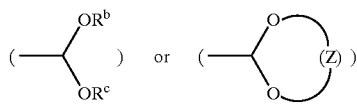

$R^b$ and $R^c$ are independent each other and represent straight or branched alkyl group of $C_1$–$C_3$, respectively; and Z represents straight or branched alkyl group of $C_1$–$C_5$, $R_4$ represents OH, H or $O(C=O)R^a$; and $R^a$ represents straight or branched alkyl group of $C_1$–$C_3$;

$R_5$ and $R_6$ are independent each other and represent H, halogen, straight or branched alkyl group of $C_1$–$C_3$, $OR^a$, $CX_3$ or $NO_2$; $R^a$ represents straight or branched alkyl group of $C_1$–$C_3$; and X represents halogen, and n is an integer of 0–2.

The present invention includes all the solvates and hydrates which can be prepared from benzopyranyl guanidine derivatives of formula 1 in addition to benzopyranyl guanidine derivatives of formula 1 and their pharmaceutically acceptable salts.

The present invention includes all the separate stereochemical isomers, i. e. diastereomerically pure or enantiomerically pure compounds which have one or more chiral centers at 2, 3 and 4-positions, in addition to the racemic mixtures or diastereomer mixtures of benzopyranyl guanidine derivatives of formula 1.

In case of having three chiral centers at 2, 3 and 4-positions, the 3,4-dihydro benzopyran derivatives according to the present invention are represented by the optical isomers such as $(I_1)$, $(I_2)$, $(I_3)$ and $(I_4)$ (See the following formula 3).

FORMULA 3

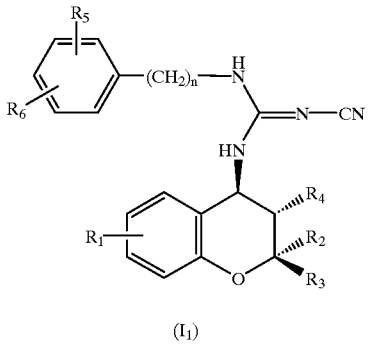

$(I_1)$

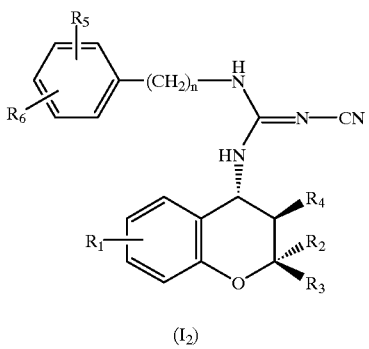

$(I_2)$

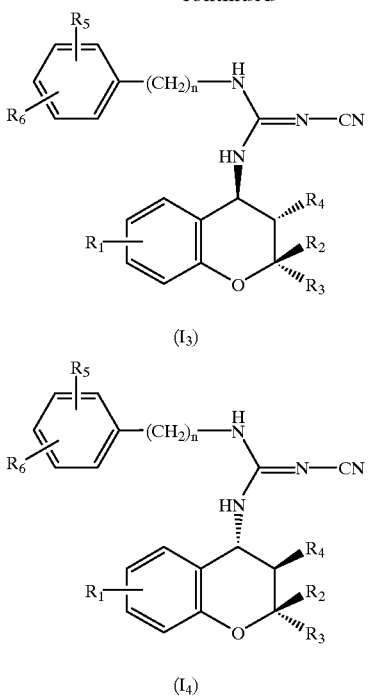

(I₃)

(I₄)

Wherein R₁, R₂, R₃, R₄, R₅, R₆ and n are defined as above.
In particular, the preferable compounds of the present invention are:

1) (2R,3R,4S)-N"-cyano-N-(6-nitro-3,4-dihydro-3-hydroxy-2-methyl-2-dimethoxymethyl-2H-benzopyran-4 yl)-N'-(4-chlorophenyl)guanidine;
2) (2R,3S,4R)-N"-cyano-N-(6-nitro-3,4-dihydro-3-hydroxy-2-methyl-2-dimethoxymethyl-2H-benzopyran-4-yl)-N'-(4-chlorophenyl)guanidine;
3) (2R,3R,4S)-N"-cyano-N-(6-nitro-3,4-dihydro-3-hydroxy-2-methyl-2-dimethoxymethyl-2H-benzopyran-4-yl)-N'-(3-chlorophenyl)guanidine;
4) (2R,3S,4R)-N"-cyano-N-(6-nitro-3,4-dihydro-3-hydroxy-2-methyl-2-dimethoxymethyl-2H-benzopyran-4-yl)-N'-(3-chlorophenyl)guanidine;
5) (2R,3R,4S)-N"-cyano-N-(6-nitro-3,4-dihydro-3-hydroxy-2-methyl-2-dimethoxymethyl-2H-benzopyran-4-yl)-N'-(4-nitrophenyl)guanidine;
6) (2R,3R,4S)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;
7) (2R,3S,4R)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;
8) (2R,3R,4S)-N"-cyano-N-(6-nitro-3,4-dihydro-3-hydroxy-2-methyl-2-dimethoxymethyl-2H-benzopyran-4-yl)-N'-(4-methoxyphenyl)guanidine;
9) (2R,3S,4R)-N"-cyano-N"-6-nitro-3,4-dihydro-3-hydroxy-2-methyl-2-dimethoxymethyl-2H-benzopyran-4 yl)-N'-(4-methoxyphenyl)guanidine;
10) (2S,3R,4S)-N"-cyano-N-(6-nitro-3,4-dihydro-3-hydroxy-2-methyl-2-dimethoxymethyl-2H-benzopyran-4-yl)-N'-(4-chlorophenyl)guanidine;
11) (2S,3S,4R)-N"-cyano-N-(6-nitro-3,4-dihydro-3-hydroxy-2-methyl-2-dimethoxymethyl-2H-benzopyran-4-yl)-N'-(4-chlorophenyl)guanidine;
12) (2S,3R,4S)-N"-cyano-N-(6-nitro-3,4-dihydro-3-hydroxy-2-methyl-2-dimethoxymethyl-2H-benzopyran-4-yl)-N'-(3-chlorophenyl)guanidine;
13) (2S,3S,4R)-N"-cyano-N-(6-nitro-3,4-dihydro-3-hydroxy-2-methyl-2-dimethoxymethyl-2H-benzopyran-4-yl)-N'-(3-chlorophenyl)guanidine;
14) (2S,3S,4R)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;
15) (2S,3S,4R)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;
16) (2S,3R,4S)-N"-cyano-N-(6-nitro-3,4-dihydro-3-hydroxy-2-methyl-2-dimethoxymethyl-2H-benzopyran-4-yl)-N'-(4-methoxyphenyl)quanidine;
17) (2S,3S,4R-N"-cyano-N-(6-nitro-3,4 dihydro-N'-(4-methoxyphenyl)guanidine;
18) (2R,3R,4S)-N"-cyano-N-(6-nitro-3,4-dihydro-3-hydroxy-2-methyl-2-dimethoxymethyl-2H-benzopyran-4-yl)-N'-(4-methylphenyl)guanidine;
19) (2R,3S,4R)-N"-cyano-N-(6-nitro-3,4-dihydro-3-hydroxy-2-methyl-2-dimethoxymethyl-2H-benzopyran-4-yl)-N'-(4-methylphenyl)guanidine;
20) (2R,3R,4S)-N"-cyano-N-(6-nitro-3,4-dihydro-3-hydroxy-2-methyl-2-dimethoxymethyl-2H-benzopyran-4-yl)-N'-(4-methoxybenzyl)guanidine;)
21) (2R,3S,4R)-N"-cyano-N-(6-nitro-3,4-dihydro-3-hydroxy-2-methyl-2-dimethoxymethyl-2H-benzopyran-4-yl)-N'-(4-methoxybenzyl)guanidine;
22) (2R,3R,4S)-N"-cyano-N-(6-nitro-3,4-dihydro-3-hydroxy-2-methyl-2-dimethoxymethyl-2H-benzopyran-4-yl)-N'-benzylguanidine;
23) (2R,3S,4R)-N"-cyano-N-(6-nitro-3,4-dihydro-3-hydroxy-2-methyl-2-dimethoxymethyl-2H-benzopyran-4-yl)-N'-benzylguanidine;
24) (2S,3S,4R)-N"-cyano-N-(6-nitro-3,4-dihydro-3-hydroxy-2-methyl-2-dimethoxymethyl-2H-benzopyran-4-yl)-N'-benzylguanidine;
25) (2S,3S,4R)-N"-cyano-N-(6-nitro-3,4-dihydro-3-hydroxy-2-methyl-2-dimethoxymethyl-2H-benzopyran-4 yl)-benzylguanidine;
26) (2R,3R,4S)-N"-cyano-N-(3,4-dihydro-3-hydroxy-2-methyl-2-dimethoxymethyl-2H-benzopyran-4-yl)-N'-(4-chlorophenyl)guanidine;
27) (2R,3S,4R)-N"-cyano-N-(3,4-dihydro-3-hydroxy-2-methyl-2-dimethoxymethyl-2H-benzopyran-4-yl)-N'-(4-chlorophenyl)guanidine;
28) (2R,3R,4S)-N"-cyano-N-(6-nitro-3,4-dihydro-3-hydroxy-2-methyl-2-hydroxymethyl-2H-benzopyran-4-yl)-N'-(4-chlorophenyl)guanidine;
29) (2R,3S,4R)-N"-cyano-N-(6-nitro-3,4-dihydro-3-hydroxy-2-methyl-2-hydroxymethyl-2H-benzopyran-4-yl)-N'-(4-chlorophenyl)guanidine;
30) (2R,3R,4S)-N"-cyano-N-(6-nitro-3,4-dihydro-3-hydroxy-2-methyl-2-methoxymethyl-2H-benzopyran-4-yl)-N'-(4-chlorophenyl)quanidine;
31) (2R,3S,4R)-N"-cyano-N-(6-nitro-3,4-dihydro-3-hydroxy-2-methyl-2-methoxymethyl-2H-benzopyran-4-yl)-N'-(4-chlorophenyl)guanidine;
32) (2S,3R,4S)-N"-cyano-N-(6-nitro-3,4-dihydro-3-hydroxy-2-methyl-2-dimethoxymethyl-2H-benzopyran-4-yl)-N'-(2-chlorophenyl)guanidine;
33) (2S,3S,4R)-N"-cyano-N-(6-nitro-3,4dihydro-3-hydroxy-2-dimethoxymethyl-2H-benzopyran-4 -yl)-N'-(2-chlorophenyl)guanidine;
34) (2S,3R,4S)-N"-cyano-N-(6-nitro-3,4-dihydro-3-hydroxy-2-methyl-2-dimethoxymethyl-2H-benzopyran-4-yl)-N'-(2-trifluoromethylphenyl)guanidine;
35) (2S,3S,4R)-N"-cyano-N-(6-nitro-3,4-dihydro-3-hydroxy-2-methyl-2-dimethoxymethyl-2H-benzopyran-4-yl)-N'-(2-trifluoromethylphenyl)guanidine;

36) (2S,3S,4S)-N"-cyano-N-(6-nitro-3,4-dihydro-3-hydroxy-2-methyl-2-dimethoxymethyl-2H-benzopyran-4-yl)-N'-(2-chlorobenzyl)guanidine;
37) (2S, 3S, 4R)-N"-cyano-N-(6-nitro-3,4-dihydro-3-hydroxy-2-methyl-2-dimethoxymethyl-2H-benzopyran-4-yl)-N'-(2-chlorobenzyl)guanidine;
38) (2S,3S,4R)-N"-cyano-N-(6-nitro-3,4-dihydro-3-acetoxy-2-methyl-2-dimethoxymethyl-2H-benzopyran-4-yl)-N'-benzylguanidine;
39) (2S)-N"-cyano-N-(6-nitro-2-methyl-2-dimethoxymethyl -2-H-benzopyran-4-yl)-N'-benzylguanidine;
40) (2S,3S,4P)-N"-cyano-N-(6-amino-3,4-dihydro-3-hydroxy-2-methyl-2-dimethoxymethyl-2H-benzopyran-4-yl)-N"'-benzylguanidine;
41) (2S,3S,4R)-N"-cyano)-N-(6-acetoxyamino-3,4-dihydro-3-hydroxy-2-methyl-2-dimethoxymethyl-2H-benzopyran -4-yl)-N'-benzylguanidine;
42) (2S,3S,4R)-N"-cyano-N-(6-methanesulfonylamino -3,4-dihydro-3-hydroxy-2-methyl-2-dimethoxymethyl-2H-benzopyran-4-yl)-N'-benzylguanidine;
43) (2S,3S,4R)-N"-cyano-N-(6-cyano-3,4-dihydro-3-hydroxy-2-methyl-2-dimethoxymethyl-2H-benzopyran-4-yl)-N'-(4-chlorophenyl)guandine;
44) (2S,3R,4S)-N"-cyano-N-(6-cyano-3,4-dihydro-3-hydroxy-2-methyl-2-dimethoxymethyl-2H-benzopyran-4-yl)-N'-(4-chlorophenyl)guanidine;
45) (2S,3S,4R)-N"-cyano-N-(6-cyano-3,4-dihydro-3-hydroxy-2-methyl-2-dimethoxymethyl-2H-benzopyran-4-yl)-N'-benzylguanidine;
46) (2S,3R,4S)-N"-cyano-N-(6-cyano-3,4-dihydro-3-hydroxy-2-methyl-2-dimethoxymethyl-2H-benzopyran-4-yl)-N'-benzylguanidine;
47) (2S,3S,4R)-N"-cyano-N-(6-bromo-3,4-dihydro-3-hydroxy-2-methyl-2-dimethoxymethyl-2H-benzopyran-4-yl)-N'-benzylguanidine;
48) (2S,3S,4R)-N"-c-yano-N-(6-nitro-3,4-dihydro-3-hydroxy-2-methyl-2-(dimethoxymethyl-2H-benzopyran-4-yl)-N'-(3,4-dimethoxybenzyl)guanidine;
49) (2S,3S,4R)-N"-cyao-N-(6-amino-3,4-dihydro-3-hydroxy-2-methyl-2-(dimethoxymethyl-21-benzopyran-4-yl)-N'-(3,4-dimethoxylbenzyl)guanidine;
50) (2S,3S,4R)-N"-cyano-N-(6-nitro-3,4-dihydro-3-hydroxy-2-methyl-2-dimethoxymethyl-2H-benzopyran-4-yl)-N'-(4-methoxybenzyl)guanidine;
51) (2S,3S,4R)-N"-cyano-N-(6-amino-3,4-dihydro-3-hydroxy-2-methyl-2-dimethoxymethyl-2H-benzopyran-4-yl)-N'-(4-methoxybenzyl)guanidine;
52) (2S,3S,4R)-N"-cyano-N-(6-nitro-3,4-dihydro-3-hydroxy-2-methyl-2-dimethoxymethyl-2H-benzopyran-4-yl)-N'-(3-nitrobenzyl)guanidine;
53) (2S,3S,4R)-N"-cyano-N-(6-nitro-3,4-dihydro-3-hydroxy-2-methyl-2-dimethoxymethyl-2H-benzopyran-4-yl)-N'-(3-trifluoromethylbenzyl)guanidine;
54) 2S,3S,4R)-N"-cyano-N-(6-amino-3,4-dihydro-3-hydroxy-2-methyl-2-dimethoxymethyl-2H-benzopyran-4-yl)-N'-(3-trifluoromethylbenzyl)guanidine;
55) (2S,3S,4R)-N"-cyano-N-(6-methanesulfonyloxy -3,4-dihydro-3-hydroxy-2-methyl-2-dimethoxymethyl-2H-benzopyran -4-yl)-N'-benzylguanidine;
56) (2R,3S,4R)-N"-cyano-N-(6-methanesulfonyloxy -3,4-dihydro-3-hydroxy-2-methyl-2-dimethoxymethyl-2H-benzopyran -4-yl)-N'-benzylguanidine;
57) (2S,3R,4S)-N"-cyano-N-(6-amino-3,4-dihydro-3-hydroxy-2-methyl-2-dimethoxymethyl-2!!-benzopyran-4-yl)-N'-benzylguanidine;
58) (2R,3R,4S)-N"-cyano-N-(6-amino-3,4-dihydro-3-hydroxy-2-methyl-2-dimethoxymethyl-2H-benzopyran-4-yl)-N'-benzylguanidine;
59) (2R,3S,4R)-N"-cyano-N-(6-amino-3,4-dihydro-3-hydroxy-2-methyl-2-dimethoxymethyl-2H-benzopyran-4-yl)-N'-benzylguanidine;
60) (2S,3S,4R)-N"-cyano-N-(6-nitro-3,4-dihydro-3-hydroxy-2-methyl-2-([1,3]dioxolan-2-yl)-2H-benzopyran-4-yl)-N'-benzylguanidine;
61) (2S,3S,4R)-N"-cyano-N-(6-amino-3,4-dihydro-3-hydroxy-2-methyl-2-([1,3]dioxolan-2-yl)-2H-benzopyran-4-yl)-N'-benzylguanidine;
62) (2S,3S,4R)-N"-cyano-N-(6-nitro-3,4-dihydro-3-hydroxy-2-methyl-2-([1,3]dioxan-2-yl)-2H-benzopyran-4-yl)-N'-benzylguanidine;
63) (2S,3S,4R)-N"-cyano-N-(6-amino-3,4-dihydro-3-hydroxy-2-methyl-2-([1,3]dioxan-2-yl)-2H-benzopyran-4-yl)-N'-benzylguanidine;
64) (2S,3S,4R)-N"-cyano-N-(6-nitro-3,4-dihydro-3-hydroxy-2-methyl-2-([1,3]-5,5-dimethyldioxan-2-yl)-2H-benzopyran -4-yl)-N'-benzylguanidine;
65) (2S,3S,4R)-N"-cyano-N-(6-amino)-3,4-dihydro-3-hydroxy-2-methyl-2-([1,3]-5,5-dimethyldioxan-2-yl)-2H-benzopyran -4-y)-N'-benzylguanidine;
66) (2S,3S,4R)-N"-cyano-N-(6-nitro-3,4-dihydro-3-hydroxy-2-methyl-2-diethoxymethyl-2H-benzopyran-4-yl)-N'-benzylguanidine;
67) (2S,3S,4R)-N"-cyano-N-(6-amino-3,4-dihydro-3-hydroxy-2-methyl-2-diethoxymethyl-2H-benzopyran-4-yl)-N'-benzylguanidine;
68) (2S,3S,4R)-N"-cyano-N-(6-methoxycarbonyl -3,4-dihydro-3-hydroxy-2-methyl-2-dimethoxymethyl-2H-benzopyran -4-yl)-N'-benzylguanidine;
69) (2R,3S,4R)-N"-cyano-N-(6-methoxycarbonyl-3,4-dihydro-3-hydroxy-2-methyl-2-dimethoxymethyl-2H-benzopyran -4-yl)-N'-benzylguanidine;
70) (3S,4R)-N"-cyano-N-(8-nitro-3,4-dihydro-3-hydroxy-2-methyl-2-dimethoxymethyl-2H-benzopyran-4-yl)-N'-benzylguanidine;
71) (2S,3S,4R)-N"-cyano-N-(8-amino-3,4-dihydro-3-hydroxy-2-methyl-2-dimethoxymethyl-2H-benzopyran-4-yl)-N'-benzylguanidine; and
72) (2R,3S,4R)-N"-cyano-N-(8-amino-3,4-dihydro-3-hydroxy-2-methyl-2-dimethoxymethyl-2H-benzopyran-4-yl)-N'-benzylguanidine.

The more, preferable compounds of the present invention are:
(2S,3S,4R)-N"-cyano-N-(6-amino-3,4-dihydro-3-hydroxy-2-methyl-2-dimethoxymethyl-2H-benzopyran-4-yl)-N'-benzylguanidine;
(2S,3S,4R)-N"-cyano-N-(6-nitro-3,4-dihydro-3-hydroxy-2-methyl-2-dimethoxymethyl-2H-benzopyran-4-yl)-N'-benzylguanidine; and
(2S,3S,4R)-N"-cyano-N-(6-nitro-3,4-dihydro-3-acetoxy-2-methyl-2-dimethoxymethyl-2H-benzopyran-4-yl)-N'-benzylguanidine.

The compounds of formula 1 may be used as pharmaceutically acceptable salts derived from pharmaceutically or physiologically acceptable free acids. These salts include but are not limited to the following: angiogenesis salts with inorganic acids such as hydrochloric acid, hydrobromic acid, sulfuric acid, sulfonic acid, phosphoric acid, stannic acid, etc. and organic acids such as citric acid, acetic acid, lactic acid, maleic acid, fumaric acid, gluconic acid, methanesulfonic acid, glycolic acid, succinic acid, tartaric acid, 4-toluenesulfonic acid, galacturonic acid, embonic acid, glutamic acid, aspartic acid, etc.

The acid salts of the compounds according to the present invention can he prepared in the customary manner, for example by dissolving the compound of formula 1 in excess aqueous acid and precipitating the salt with a water-miscible organic solvent, such as methanol, ethanol, acetone or acetonitrile. It is also possible to prepare by heating equivalent amounts of the compound of formula 1 and an acid in water or an alcohol, such as glycol monomethyl ether, and then evaporating the mixture to dryness or filtering off the precipitated salt with suction.

Also the compounds of formula 1 may be in the form of pharmaceutically acceptable ammonium, alkali metals or alkaline earth metals salts. The alkali metal or alkaline earth metal salts of the compound of formula 1 can be obtained, for example, by dissolving the compound of formula 1 in equimolar amount of alkali metal or alkaline earth metal hydroxide solution, filtering from the undissolved materials and evaporating the filtrate to dryness. Sodium, potassium or calcium salts are pharmaceutically suitable. The corresponding silver salts are obtained by the reaction of an alkali metal or alkaline earth metal salt with a suitable silver salt, such as silver nitrate.

In addition, the present invention provides processes for preparing of the benzopyranyl guanidine derivatives of formula 1.

In particular, the present invention provides processes for preparing of the benzopyranyl guanidine derivatives of formula 1, represented by the following scheme 1 (Preparation Method T).

SCHEME 1

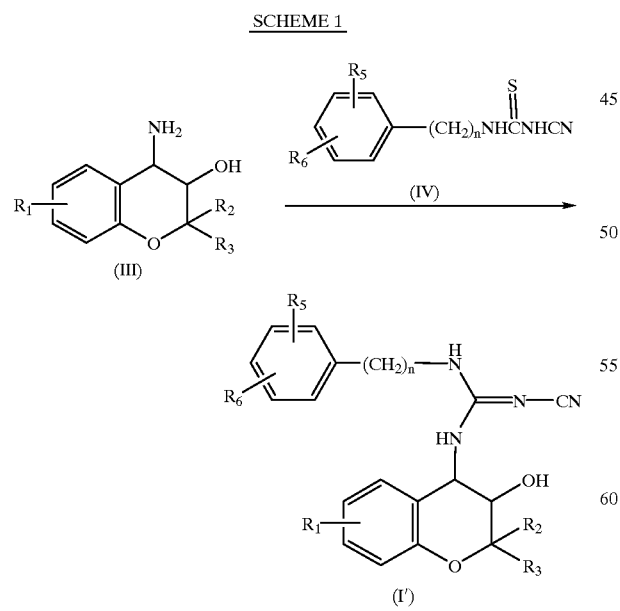

Wherein $R_1$, $R_2$, $R_3$, $R_4$, $R_5$, $R_6$ and n are each defined as above.

The present invention also provides processes for preparing of the benzopyranyl guanidine derivatives of formula 1, represented by the following scheme 2 (Preparation Method II).

SCHEME 2

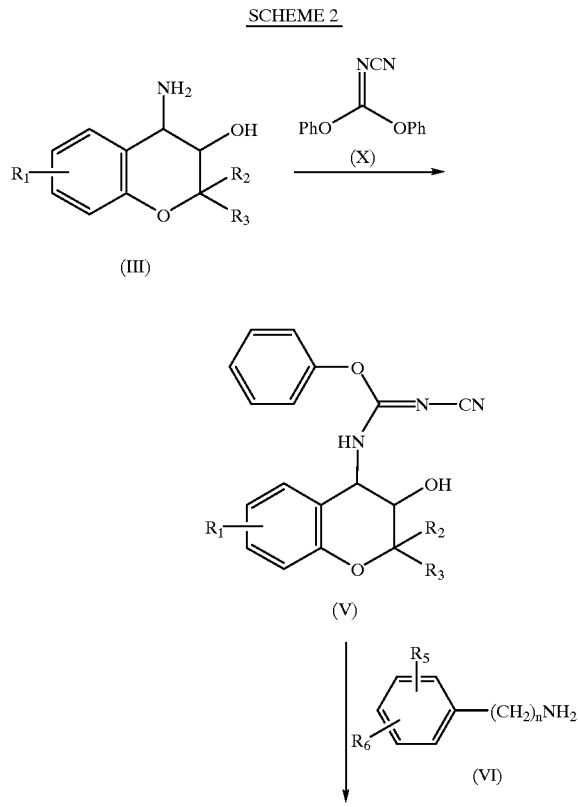

Wherein $R_1$, $R_2R_3$, $R_4$, $R_5$, $R_6$ and n are each defined as above.

In addition, the present invention provides processes for preparing of the benzopyranyl guanidine derivatives of formula 1 by using the compound (I') prepared in the scheme 1 or scheme 2, represented by the following scheme 3.

SCHEME 3

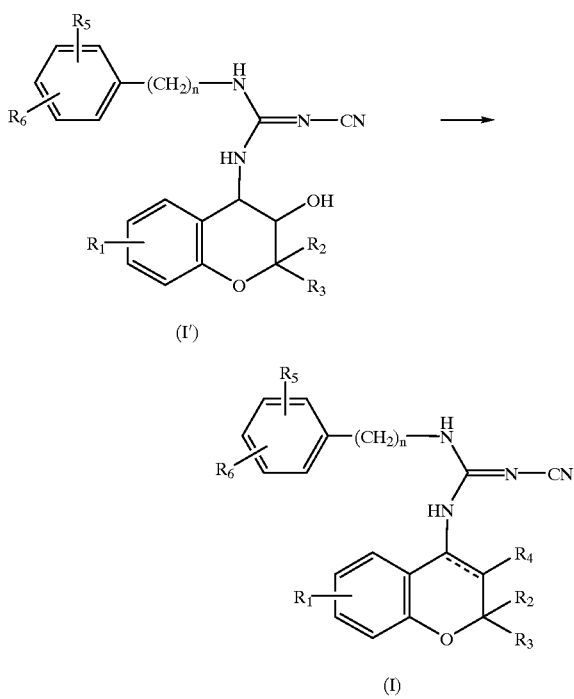

Wherein $R_1$, $R_2$, $R_3$, $R_4$, $R_5$, $R_6$ and n are each defined as to above.

The substituents of $R_1$, $R_2$, $R_3$, $R_4$, $R_5$, and $R_6$ can be modified or 3,4-double bond can be formed via the reaction represented by the above scheme 3.

The derivatives of formula 1 can be prepared separately as an optically active isomer by using the corresponding optical isomer as a starting material.

In case of using a racemic mixture as a starting material, the derivatives of formula 1 are prepared as a racemic mixture, and then the racemic mixture is separated into each optical isomers. The optical isomers can be separated by common chiral column chromatography or recrystallization.

The compounds of formula 1 can be synthesized using the reactions and techniques described herein below. The reactions are performed in a solvent appropriate to the reagents and materials employed and suitable for the transformation being effected.

I. Preparation of Starting Materials

Aminoalcohol compounds (III) which were used as a starting material in scheme I or scheme 2, can be prepared by the reaction represented by the following scheme 4.

SCHEME 4

Wherein $R_1$, $R_2$ and $R_3$ are each defined as above, (OZ) represents a leaving group and Hal represents a halogen atom.

The method for the preparation of the epoxide compound (II) represented by the above scheme 4 is described in U.S. Pat. No. 5,236,935 and KR Pat. No. 096,546 which were acquired by the present inventors, in detail.

Also, the epoxide compound (II) can be prepared from propazylether derivatives (*J. Med. Chem.* 26, 1582 (1983)).

(1) Preparation of Olefin Compounds (VIII)

Olefin compounds (VIII) exist as enantiomers ($VIII_1$ and $VIII_2$) such as formula 4.

FORMULA 4

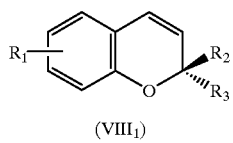

($VIII_1$)

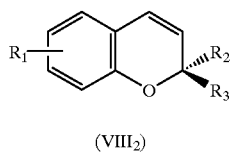

($VIII_2$)

Wherein $R_1$, $R_2$ and $R_3$ are each defined as above.

Olefin compounds (VIII) can be obtained separately as an optically active olefin compound ($VIII_1$) and olefin compound ($VIII_2$) of formula 4, respectively. The olefin compound (VIII) can be prepared by the method disclosed in KR Pat. Appln. No. 96-7399 according to the present inventors.

The following scheme 5 shows the detail process for the preparation of the olefin compound (VIII) from an alcohol compound (VII).

SCHEME 5

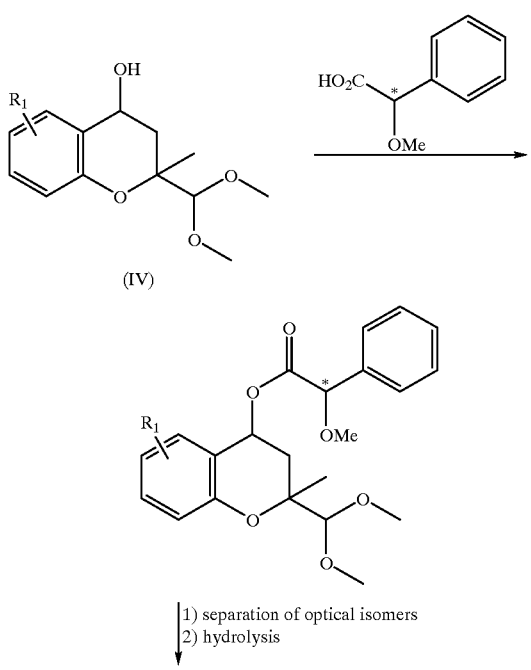

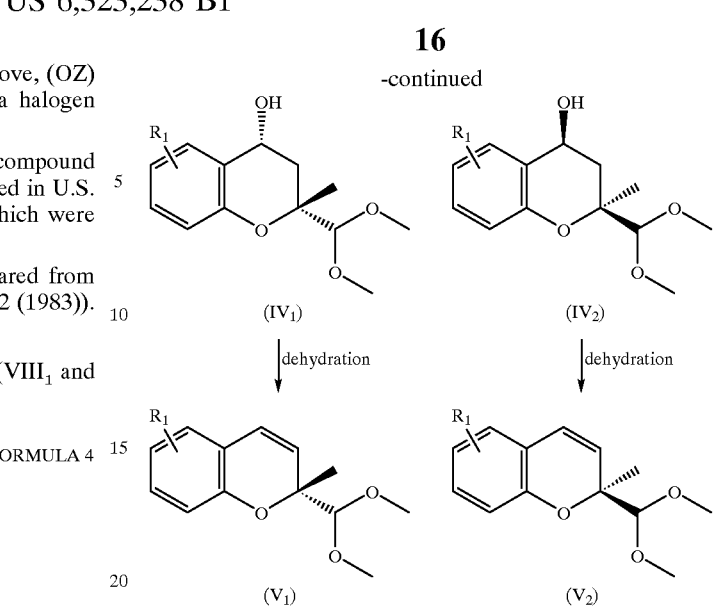

Wherein $R_1$, $R_2$ and $R_3$ are each defined as above.

(2) Preparation of Epoxide Compounds (II)

Epoxide compounds ($II_1$) and epoxide compounds ($II_2$) can be prepared from the compound ($VIII_1$) and epoxide compounds ($II_3$) and epoxide compounds ($II_4$) can be prepared from the compound ($VIII_2$) as represented by the following scheme 6, by using the compound ($VIII_1$) and the compound ($VIII_2$) prepared in scheme 5 as a starting material, respectively.

SCHEME 6

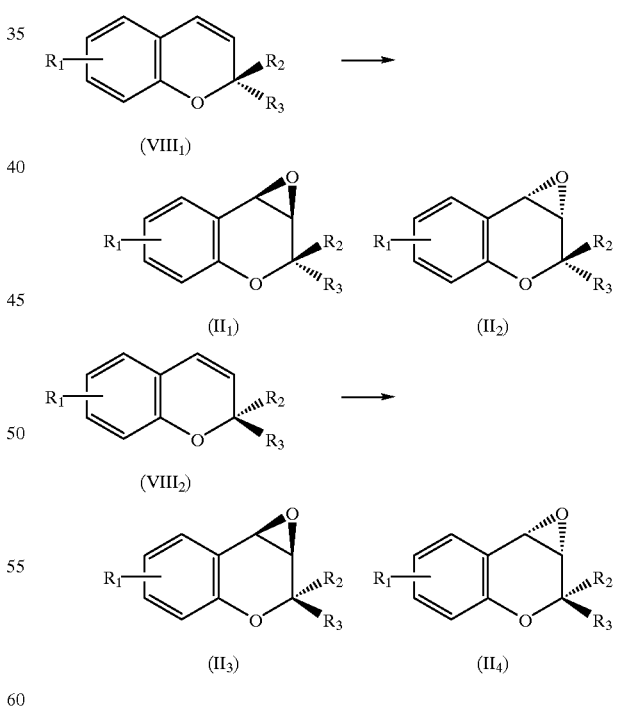

Wherein $R_1$, $R_2$ and $R_3$ are each defined as above.

The epoxide compounds ($II_1$) and ($II_2$) can be separated to each optical isomer, and all the separated epoxide compounds or the mixture thereof an be used in the next: step. Also the epoxido compounds ($II_3$) and ($II_4$) can be separated, and all the separated epoxide compounds or the mixture thereof can be used in the next step.

Epoxide compounds (II$_1$) and (II$_2$) and epoxide compounds (II$_3$) and (II$_4$) can be prepared from olefin compounds (VIII$_1$) and (VIII$_2$), respectively, by the preparation method disclosed in U.S. Pat. No. 5,236,935 and KR Pat. No. 096,546 which were acquired by the present inventors.

It is also possible to prepare optical isomers (II$_1$), (II$_2$), (II$_3$) and (II$_4$) of epoxide compounds, respectively, from olefin compounds (VIII$_1$) or (VIII$_3$), by using Mn(III) salen epoxidation catalysts (E. N. Jacobsen et al., *Tetrahedron Lett.*, 38, 5055 (1991)). In case of using (R, R)—Mn(III) salen catalyst, epoxide compounds (II$_1$) can be prepared from olefin compounds (VIII$_1$) and epoxide compounds (II$_3$) from the olefin compounds (VIII$_2$). In case of using (S, S)—Mn(III) salen catalyst, epoxide compounds (II$_2$) can be prepared from the olefin compounds (VIII$_1$) and epoxide compounds (II$_4$) from the olefin compounds (VIII$_2$). This epoxidation reaction is performed in mixture of methylene chloride and water by using NaOCl as an oxidizing agent.

(3) Preparation of Aminoalcohol Comopunds (III)

Aminoalcohol compounds (III) are prepared by the reaction of the epoxide compound (II) with ammonia gas (NH$_3$) or ammonium hydroxide (NH$_4$OH) in the presence of a suitable solvent, in the above scheme 4. Preferred solvent are alcohols such as methanol, ethanol, isopropanol, etc. The reaction temperature may range from 5° C. to the boiling point of the solvent employed.

In case of using each epoxide compound (II$_1$), (II$_2$), (II$_3$) and (II$_4$) as a starting material, aminoalcohol compounds (III$_1$), (III$_2$), (III$_3$) and (III$_4$) can be obtained, respectively. In case of using a mixture of epoxy compound (II$_1$) and (II$_2$) as a starting material, a mixture of aminoalcohol compounds (III$_1$) and (III$_2$) is obtained. And in case of using a mixture of epoxide compound (II$_3$) and (II$_4$) as a starting material, a mixture of aminoalcohol compounds (III$_3$) and (III$_4$) is obtained.

FORMULA 5

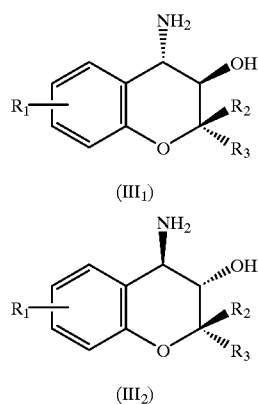

(III$_1$)

(III$_2$)

Wherein R$_1$, R$_2$ and R$_3$ are each defined as above.

FORMULA 6

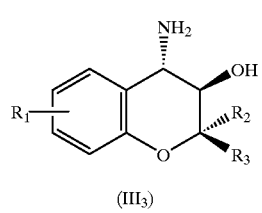

(III$_3$)

-continued

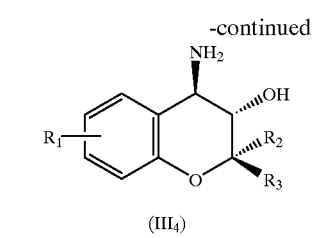

(III$_4$)

Wherein R$_1$, R$_2$ and R$_3$ are each defined as above.

II. Preparation Method I

The method for the preparation of the compounds formula 1 comprises the step of reacting an aminoalcohol compound (III) and a thiourea compound (IV) in the presence of a suitable condensing agent and a suitable solvent. The compound (I'), which is a compound of formula 1 with the R$_4$=OH, is prepared by this reaction.

Examples of such condensing agents include carbodiimide-type condensing agents such as 1-[3-(dimethylamino)propyl]-3-ethylcarbodiimide hydrochloride, and N,N'-dicyclohexylcarbodiimide, etc. More preferably water-soluble carbodiimide-type condensing agents are employed.

One to three equivalents of the condensing agent is preferable, to that of the aminoalcohol compound (III). Also one to two equivalent of thiourea compound (IV) is preferable, to that of the aminoalcohol compound (III).

Preferable solvents are methylene chloride, chloroform, dimethylformamide, dimethylsulfoxide, tetrahydrofuran, 1,2-dichloroethane, dioxane, etc.

Reaction temperature may range from 5° C. to 40° C.

In case of using each stereoisomer of the aminoalcohol compound (III) as a starting material, the product with the same configuration to that of the starting material is obtained, respectively. That is, the compounds (I$_1$), (I$_2$), (I$_3$) and (I$_4$) of formula 1 can be prepared from aminoalcohol compounds (III$_1$), (III$_2$), (III$_3$) and (III$_4$), respectively. In case of using a mixture of aminoalcohol compounds (III$_1$) and (III$_2$) as a starting material, a mixture of compounds (I$_1$) and (I$_2$) is obtained. And in case of using a mixture of aminoalcohol compounds (III$_3$) and (III$_4$) as a starting material, a mixture of compounds (I$_3$) and (I$_4$) is obtained. A mixture of the compounds of formula 1 can be separated to afford the separated optical isomers. The optical isomers can be separated by common column chromatography or recrystallization.

The thiourea compound (IV) used in the above reaction can be prepared by the reaction of an isocyanate compound (IX) with sodium cyanamide (NaHNCN) in ethanol as represented by the following scheme 7.

SCHEME 7

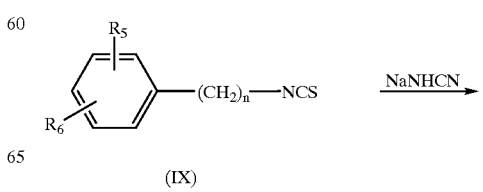

(IX)

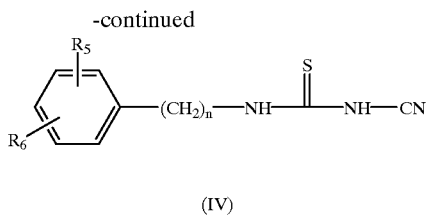

(IV)

Wherein $R_5$, $R_6$ and n are each defined as above.

III. Preparation Method II

Another method for the preparation of the compounds of formula 1 comprises 1) reacting an aminoalcohol compound (III) with diphenyl cyanocarbonimidate (X) in the presence of a base to prepare the compound (V) (step 1); and
2) reacting the compound (V) with an appropriate amine compound (VI) in a suitable solvent to prepare the compound (I') (step 2).

The compound (I') which is a compound of formula with $R_4$=CH, is prepared by this reaction.

In step 1, various inorganic and organic bases can be employed. Examples of such inorganic bases include $CaCO_3$, NaOH, KOH, $Na_2O_3$, $NaHCO_3$, etc. Examples of such organic bases include metal salts of alcohols such as sodium methoxide ($CH_3ONa$), sodium ethoxide ($CH_3CH_2ONa$) etc.; sodium acetate ($CH_3COONa$); metal salts of ammonia; bicyclic amines such as 1,8-diazabicyclo[5.4.0]undec-7-ene (DBU), 1,5-diazabicyclo[4.3.0]non-5-ene (DBN), etc.; triethylainine; N,N-diisoprocylethylamine; pyridine; lutidine; N,N-dimethylaniline; 4-(dimethylamino)-pyridine; 1,4-diazabicyclo[2.2.2]octane (DABCO), etc. More prefereablly tertiary amines are employed such as triethylamine, N,N-diisopropylethylamine, pyridine, 1,8-diazabicyclo[5.4.0]undec-6-ene, 4-(dimethylamino)pyridine, etc.

One to three equivalent of the base is preferable, to that of the aminoalcohol compound (III). And one to two equivalent of diphenyl cyanocarbonimidate (X) is preferable, to that of the aminoalcohol compound (III).

Preferred solvents are alcohols such as ethanol, isopropanol, etc., dimethylformamide (DMF), dimethylsulfoxide (DMSO), chloroform, etc.

Reaction temperature is preferably maintained from 5° C. to the boiling point of solvent employed.

In step 2, one to five equivalent of the amine compound (VI) is preferable, to that of the aminoalcohol compound (III).

Examples of the reaction solvent are alcohols such as ethanol, Lsoproparioi, etc., dimethylformamide, dimethylsulfoxide, chloroform, methylene chloride, tetrahydrofuran (THe), etc.

Reaction temperature is preferably maintained from 5° C. to the boiling point of solvent employed.

In addition, the reaction of step 2 can be carried out in the presence of a base. Examples of such bases are mentioned as above.

In case of using each optical isomer of aminoalcohol compound (III) as a starting material, the product (I') with the same configuration of the starting material is obtained, respectively. Tn case of using a mixture of aminoalcohol compounds ($II_1$) and ($III_2$) as a starting material, a mixture of compounds ($I_1$) and ($I_2$) is obtained. In case of using a mixture of aminoalcohol compounds ($III_3$) and ($III_4$) as a starting material, a mixture of compounds ($I_3$) and ($I_4$) is obtained. A mixture of optical isomers can be separated to afford the separated optical isomers of compounds (I'). The optical isomers can be separated by common column chromatography or recrystallization.

IV. Preparation of Compounds (I) from Compounds (I')

The substituents $R_1$, $R_2$, $R_3$, $R_4$, $R_5$ or $R_6$ can be modified to other functional groups, and a double bond can be formed at 3,4-position by the reaction of scheme 3. In this reaction, the compounds (I') are used as a starting material, which has been prepared by the above scheme 1 or scheme 2.

A starting material, reactants and the reaction condition are determined according to the structure of product, that is what are the substituents $R_1$, $R_2$, $R_3$, $R_4$, $R_5$ and $R_6$ and whether there is a double bond at 3,4-position. Therefore the present invention includes all the reaction types, reactants and reaction condition by which it is possible to prepare the compound of formula 1.

Several processes for the preparation of the compounds of formula 1 according to scheme 3 are described below in detail. However, the description of the process should not be understood to limit the present invention.

(1) Introduction of Acethoxy Group at $R_4$

Acetoxy group can be introduced at $R_4$ by reacting the compound (I') with acetic anhydride in suitable solvent in the presence of a suitable catalyst as represented in the below scheme 8.

SCHEME 8

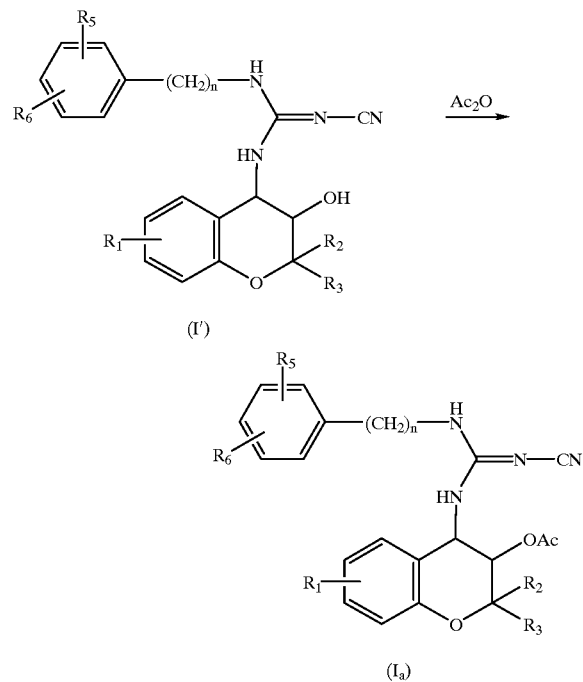

Wherein $R_1$, $R_2$, $R_3$, $R_4$, $R_5$, $R_6$ and n are each defined as above.

Preferred bases are mentioned as above. More preferably triethylamine, pyridine or N,N-diisopropylethylamine is employed.

Preferred catalyst is 4-(dimethylamino)pyridine. One to three equivalent of the base is preferable, to that of the compound (I'). And 0.05–0.5 equivalent of the catalyst is preferable, to that of the compound (I').

Preferred solvents are methylene chloride, chloroform, tetrahydrofuran, acetonitrile, etc. The reaction 10 temperature is preferably 0–40° C.

(2) Introduction of Double Bond at 3,4-position $R_4$ is substituted with hydrogen atom and a double bond is formed at 3,4-position by reacting the acetate compound ($I_a$) prepared in the above scheme 8 with suitable base in suitable solvent as represented in the below scheme 9.

SCHEME 9

(I$_a$)

(I$_b$)

Wherein $R_1$, $R_2$, $R_3$, $R_4$, $R_5$, $R_6$ and n arc each defined as above.

Preferred bases are mentioned as above. More preferably 1,8-diazabicyclo[5.4.0]undec-7-ene, 1,5-diazabicyclo[4.3.0]non-5-ene or 1,4-diazabicyclo[2.2.2]octane is employed.

One to three equivalents of the base is preferable, to that of compound ($I_a$).

Preferred solvents are toluene, benzene, xylene, dioxane, etc. The reaction temperature is preferably from 5° C. to the boiling point of solvent.

(3) Introduction of $NH_3$ Group at $R_1$ p The compound ($I_d$) of formula 1 whose $R_1$ is $NH_2$ can be prepared by the reduction of the compound ($I_c$) with $R_1=NO_2$ as represented in the below scheme 10.

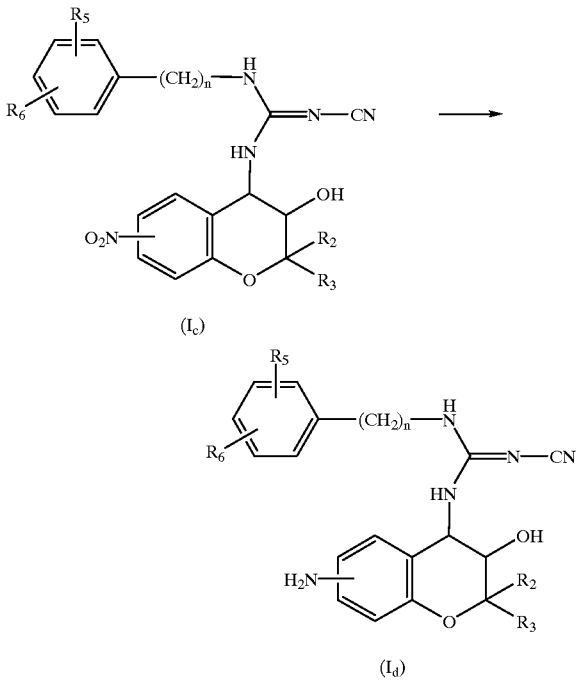

SCHEME 10

(I$_c$)

(I$_d$)

Wherein $R_2$, $R_3$, $R_5$, $R_6$ and n are each defined as above.

The $NO_2$ group can be reduced to $NH_2$ group by hydrogenation using metal catalysts such as platinum, palladium, palladium on carbon (Pd/C), Paney-nickel, etc. in a suitable solvent. Preferred solvents are alcohols such D as methanol, ethanol, etc., and ethyl acetate.

In addition, the reduction of $NO_2$ group to $NH_2$ group can be carried out by using a reducing agent such as $NaBH_4$ in the presence of $CuSO_4$, $Cu(OAc)_2$, $CoCl$, $SnCl_2$ or $NiCl_2$. At this time, preferred solvent is a mixture of water and methanol and room temperature for reaction temperature is preferred.

(4) Introduction of NH(C=O)$R^a$ at $R_1$

The compound of formula 1 with $R^1$=NH(C=O)$R^a$ can be prepared by the reaction of the compound ($I_d$) prepared in the above scheme 10 with acylchloride or acid anhydride in the presence of a base.

Preferred bases are mentioned as above. More preferably bases are employed such as triethylamine, N,N-diisopropylethylamine, pyridine or 4-(dimethylamino) pyridine. Preferred solvents are methylene chloride, chloroform, dimethylsulfoxide, dimethylformamide, tetrahydrofuran and dioxane.

(5) Introduction of —NHS(O)$_m$R$^a$ at $R_1$

The compound of formula 1 with $R_1$=—NHS(O)$_m$R$^a$ can be prepared by the reaction of the compound (Id) prepared in the above scheme 10 with alkylsulfonyl chloride or arylsulfonyl chloride in the presence of a base.

Preferred bases are mentioned as above. More preferably bases are employed such as triethylamine, N,N-diisopropylethylamine, pyridine and 4-(dimethyLamino) pyridine. Preferred solvents are methylene chloride, chloroform, dimethylsulfoxide, dimethylformamide, tetrahydroturan and dioxane.

In addition, the present invention provides pharmaceutical compositions which contain the benzopyranyl guanidine derivatives of claim 1 or their pharmaceutically acceptable salts as an active ingredient. In particular, the present invention provides pharmaceutical compositions for protecting heart, protecting neuronal cells or protecting of brain injury, or protecting preserving organs, inhibiting NO generation and lipid peroxidation or suppressing angiogenesis and restenosis.

In the experiments using isolated rat aorta, the compounds of the present invention showed remarkably low vasorelaxant activity compared to the reference $K_{ATP}$ openers such as Cromakalim and BMS-180448. While the KAY openers have cardioprotective properties by exerting their effects on heart, those have vasorelaxant properties by acting on the $K_{ATP}$ located in smooth muscle. The vasodilation effect is unnecessary, probably contraindicated for ischemia, due to under perfusion of the tissue already at risk. In other words, the vasorelaxant effect of these compounds would limit their utility in treating myocardial ischemia. As mentioned above, the compounds of the present invention are nearly devoid of vasorelaxant activity, thus their cardiac selectivity might offer a higher margin of safety as cardioprotectants.

Accordingly, the compounds of the present invention are confirmed their antiischemic activity with significant improvement in cardiac selectivity. In the ischemic myocardium injury models of anesthetized rats, the compounds of the present invention exhibited equal or superior antiischemic activity compared to that of BMS-180448. Further, in contrast to BMS-180448, the compounds of the present invention have noticeably low vasorelaxant activity and thus, they are far superior to the conventional drugs as cardiac selective cardioproteclants. In addition, in the ischemic myocardium unjury models of anesthetized beagle dogs, the compounds of the present invention considerably reduced the size of infarct zone as a percentage of area at risk (%IZ/AAR), which was superior to the reference BMS180448.

As described above, the compounds of the present invention show almost no vasodilatation activity, but exert excellent anti-ischemic activity on various animals, so that they can be used for the prevention or treatment of the diseases related to myocardial ischemia, such as postischemic contractile dysfunction as well as a cardiprotective in myocardial infarction, angina pectoris and congestive heart failure.

In addition, the compounds of the present invention have an ability to protect neurons. In detail, the compounds of the present invention protect neurons from oxidative injury by iron dose-dependently. Also, the compounds of the present invention protect retinal cell death from ischemic damage dose-dependently, and represent neuroprotective effects by improving impaired MNCV (motor nerve conduction velocity) and nociceptive responses using hot plates in diabetic rats. And the compounds of the present invention protect hypoxic brain injury in newborn rats by, decreasing the value of lipid/NAA (N-aetyl aspartate) and (lipid)/Cr (creatine) in proton PRS (magnetic resonance spectroscopy). Therefore, the compounds of the present invention can be used as a neuroprotectives and can also be applied for the treatment of neurodegenerative disorders caused by the apoptosis or necrosis of neurons, such as stroke, cerebral dementia, infant asphyxia, glaucoma, diabetic neuropathy, and head trauma.

Further, the compounds of the present invention inhibit the lipid peroxidation induced by iron or copper and LDL (low density lipoprotein) oxidation in A7r5 (rat aortic smooth muscle cell), whose antioxidant effect was more significant when $H_2O_2$ was added. In addition, the compounds of the present invention inhibit ROS (reactive oxygen species) induced by $H_2O_2$ both in A7r5 and HUVEC cells, and remove oxygen radicals in ORAC (oxygen radical absorbance capacity) test using AAPH (2.2'-azobis(2-aminopropane)dihydrodichloride) as a radical generator. Hence, the compounds of the present invention can be used as an antioxidant against lipid peroxidation and can be effectively applied for the medical treatment of the neurological disorders caused by the accumulation of free radical species within neurons, such as neurodegenerative diseases (stroke and dementia), atherosclerosis and inflammation.

Furthermore, the compounds of the present invention inhibit No (nitric oxide) formation induced by endotoxins such as lipopolysaccharide (LPS), dose-dependently. Therefore, the compounds of the present invention can be used as inhibitors against NO production and can be effectively applied for the treatment of inflammatory diseases such as arthritis, cardiac infarction, arteriosclerosis, and dementia, which are caused by the injury of tissues or organs as a result of the apoptoic or necroptic cell death due to accumulation of NO within the cells.

Moreover, the compounds of the present invention effectively protect the brain from ischemia-reperfusion injury. The compounds of the present invention have advantage over the reference MK801. While the MK 801-treated rats showed decreased motility as a side effect, rats treated with the compounds of the present invention did not show any significant side effects such as behavioral change. Hence, the compounds of the present invention can be used as a neuroprotective agent against brain ischemia-reperfusion damage and can be effectively applied for the treatment of various diseases caused by brain ischemic injury such as ischemic cerebral vascular occlusion induced by thrombi.

In the experiment of the formation of new blood vessels induced by antiotensin II, the compounds of the present invention effectively inhibit the angiogenesis. In particular the compounds of the present invention are able to almost completely prevent the formation of new blood vessels in a dose-dependent manner. Therefore, the compounds of the present invention can be used as an angiogenesis inhibitor and can be usefully applied for the medical treatment of various diseases induced by angiogenesis, such as rheumatoid arthritis, psoriasis, AIDS complications, and cancers.

Also, the compounds of the present invention significantly suppress vascular smooth muscle cell proliferation by inhibition of DNA synthesis in [$^3$H]-thymidine incorporation experiments. Hence, the compounds of the present invention can be used for the prevention and treatment of restenosis, frequently occurred after percutaneous coronary intervention.

Also, the compounds of the present invention can be used for protection of preserving organs such as heart, kidney, liver, and tissues and for the protection of organs in major cardiovascular surgery.

The present invention includes pharmaceutical formulations which contain, in addition to non-toxic, inert pharmaceutically suitable additives, one or more than one active ingredients according to the present invention and processes for the preparation of these formulations.

The present invention also includes pharmaceutical formulations in dosage units. The dosage unit of each formulations, for example tablets, coated tablets, capsules, pills, suppositories and ampules, contain the more than one active ingredients corresponding to a fraction or a multiple of an individual dose. For example the dosage units can contain 1, 2, 3 or 4 times or ½, ⅓ or ¼ active ingredients of an individual dose. A dosage unit preferably contains the amount of active ingredients which is administered in one application or which usually corresponds to a whole, one half, one third or a quarter of a daily dose.

Non-toxic inert pharmaceutically suitable vehicle includes as solid, semi-solid or liquid diluents, fillers and formulation additives of all types.

Preferred pharmaceutical formulations are tablets, coated tablets, capsules, pills, granules, suppositories, solutions, suspensions and emulsions, pastes, ointments, gels, reams, lotions, dusting powders and sprays.

Tablets, coated tablets, capsules, pills and granules can contain more than one additives in addition to the active ingredient or ingredients, such as (a) fillers and diluents, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrants, for example agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate, and solid polyethylene glycols, or mixtures of the substances listed under (a) to (i).

The tablets, coated tablets, capsules, pills and granules can be provided with the customary coatings and shells, optionally containing opacifying agents, and can also be of a composition such that they release the active ingredient or ingredients only or preferentially in a certain part of the intestinal tract, if appropriate in a delayed manner, examples of embedding compositions which can be used being polymeric substances and waxes.

If appropriate, the active ingredient or ingredients can also be present in microencapsulated form with one or more of the above mentioned excipients.

Suppositories can contain, in addition to the active ingredient or ingredients, the customary water-soluble or water-insoluble excipients, for example polyethylene glycols, fats, for example cacao fat, and higher esters (for example, $C_{14}$-alcohol with $C_{16}$-fatty acid) or mixtures of these substances.

Ointments, pastes, creams and gels can contain, in addition to the active ingredient or ingredients, the customary oxcipients, for example animal and vegetable fats, waxes, paraffins, starch, tragacanth, cellulose derivatives, polyethylene glycols, silicones, bentonites, silicic acid, talc and zinc oxide, or mixtures of these substances.

Dusting powders and sprays can contain, in addition to the active ingredient or ingredients, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active ingredient or ingredients, the customary excipients, such as solvents, solubilizing agents and emulsifiers, for example water, ethyl alcohol, isopropyl alcohol, ethylcarbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuyl alcohol, polyethylene glycols and fatty acid esters of sorbitan, or mixtures of these substances.

For parenteral. administration, the solutions and emulsions are also be in a sterile form which is isotonic with blood.

Suspensions can contain, in addition to the active ingredient or ingredients, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain coloring agents, preservatives and additives which improve the smell and taste, for example peppermint oil and eucalyptus oil, and sweeteners, for example saccharin.

The therapeutically active ingredients should preferably be present in the abovementioned pharmaceutical formuLations in a concentration of about 0.1 to 99.5, preferably about 0.5 to 95% by weight of the total mixture.

The abovementioned pharmaceutical formulation can also contain other pharmaceutical active compounds in addition to the compounds according to the present invention.

The abovementioned pharmaceutical formulations are prepared in the customary manner by known methods, for example by mixing the active ingredient or ingredients with vehicles.

The formulations mentioned can be used on humans and animals either orally, rectally, parenterally (intravenously, intramuscularly or subcutaneously), intracisternally, intravaginally, intraperitoneally or locally (dusting, powder, ointment, drops) and for the therapy of infections in hollow spaces and body cavities. Possible suitable formulations are injection solutions, solutions and suspensions for oral therapy and gels, infusion formulations, emulsions, ointments or drops, ophthalmological and dermatological formulations, silver salts and other salts, eardrops, eye ointments, dusting powders or solutions can be used for local therapy. In the case Of animals, intake can also be in suitable formulations via the feed or drinking water.

Gels, powders, dusting powders, tablets, delayed release tablets, premixes, concentrates, granules, pellets, boli, capsules, aerosols, sprays and inhalants can further more be used on humans and animals. The compounds according to the present invention can moreover be incorporated into other carrier materials, such as for example, plastics (chain of plastic for local therapy), collagen or bone cement.

D In general, it has proved advantageous in human medicine to administer the active ingredient or ingredients according to the present invention in total amounts of about 0.1 to about 100, preferably 0.1 to 20 mg/kg of body weight every 24 hours, if appropriate in the form of several individual doses, to achieve the desired results. However, it may be necessary to deviate from the dosages mentioned, and in particular to do so as a function of the nature and body weight of the object to be treated, the nature and severity of the disease, the nature of the formulation and of the administration of the medicament and the period or interval within which administration takes place.

Thus in some cases it can suffice to manage with less than the abovementioned amount of active ingredient, while in other cases the abovementioned amount of active ingredient must be exceeded. The particular optimum dosage and mode of administration required for the active ingredient can be determined by any expert on the basis of his expert knowledge.

The molecular structure of the compounds according to the present invention was identified by IR spectroscopy, UV spectroscopy, NMR spectroscopy, mass spectroscopy, liquid chromatography, X-ray diffraction, optical rotation analysis and elemental analysis.

PREPARATION EXAMPLES

The starting materials (III) of scheme 1 or scheme 2 were prepared by the following preparation examples.

Preparation Example 1

Preparation of (2R,3R,4S)-6-nitro-2-methyl-2-dimethoxymethyl-3-hydroxy-4-amino-3,4-dihydro-2H-1-benzopyran and (2R,3S,4R)-6-nitro-2-methyl-2-dimethoxymethyl-3-hydroxy-4-amino-3,4-dihydro-2H-1-benzopyran (Step 1) Preparation of (2R)-6-nitro-2-methyl-2-dimethoxymethyl-3,4-epoxy-3,4-dihydro-2H-1-benzopyran To a solution of 75 g (0.28 mol) of (2R)-6-nitro-2-methyl-2-dimethoxymethyl-2H-1-benzopyran in 1 L of acetone was added 1 L of water. To the mixture was added 84 g (0.99 mol) of sodium hydrogen carbonate and the mixture was stirred for 10 min. To the mIxture was added 174 g (0.28 mol) of oxone and the mixture was strongly stoed. Sodium hydrogencarbonate and oxone were added to the mixture three times more every 15 min. The reaction mixture was filtered, acetone was removed under reduced pressure and the residue was extracted with ethyl acetate (500 ml×2). The organic layer was dried over anhydrous magnesium sulfate, filtered, concentrated and purified by silica gel column chromatography (n-hexane:ethyl acetate=4:1) to afford 76 g (yield: 95%) of the desired compound as a white solid.

(Step 2) Preparation of (2R,3R,4S)-6-nitro-2-methyl-2-dimetshoxymethyl-3-hydroxy-4-amino-3,4-dihydro-2H-1-benzopyran and (2R,3S,4R)-6-nitro-2-methyl-2-dimethoxymethyl-3-hydroxy-4-amino-3,4-dihydro-2H-1-benzopyran 8.8 g of the epoxide compound prepared in the step 1 was dissolved in 250 ml of the saturated ammonia ethanol and the reaction mixture was stirred for 7 days at room temperature. The solvent was removed and the residue was purified by silica gel column chromatography (n-hexane:ethyl ethyl acetate=1:4) to recover 2.58 g of the starting material and to afford 5.6 g (yield: 60%) of the desired compound as a racemic mixture.

Preparation Example 2

Preparation of (2S,3R,4S)-6-nitro-2-methyl-2-dimethoxymethyl-3-hydroxy-4-amino-3,4-dihydro-2H-1-benzopyran and (2S,3S,4R)-6-nitro-2-methyl-2-dimethoxymethyl-3-hydroxy-4-amino-3,4-dihydro-2H-1-benzopyran (Step 1) Preparation of (2S)-6-nitro-2-methyl-2-dimethoxymethyl-3,4-epoxy-3,4-dihydro-2H-1-benzopyran To a solution of 5 g (19 mmol) of (2R)-6-nitro-2-methyl-2-dimethoxymethyl-2H-1-benzopyran in 100 ml of acetone was added 100 ml of water. To the mixture was added 5.6 g (66 mmol) of sodium hydrogen carbonate and the mixture was stirred for 10 min. To the mixture was added 11.6 g (19 mmol) of oxone and the mixture was strongly stirred. Sodium hydrogencarbonate and oxone were added to the mixture three times more every 15 min. The reaction mixture was filtered, acetone was removed under reduced pressure and the residue was extracted with ethyl acetate (100 ml×2). The organic layer was dried over anhydrous magnesium sulfate, filtered, concentrated under reduced pressure and purified by silica gel column chromatography (n-hexane:ethyl acetate=4:1) to afford 5.1 g (yield: 97%) of the desired compound, a white solid as a racemic mixture.

(Step 2) Preparation of (2S,3R,4S)-6-nitro-2-methyl-2-dimethoxymethyl-3-hydroxy-4-amino-3,4-dihydro-4-amino-3,4-dihydro-2H-1-benzopyran and (2S,3S,4R)-6-nitro-2-methyl-2-dimethoxymethyl-3-hydroxy-4-amino-3,4-dihydro-4-amino-3,4-dihydro-2H-1-benzopyran 5.1 g of the epoxide compound prepared in the step 1 was dissolved in 100 ml of the saturated ammonia ethanol and the reaction mixture was stirred for 7 days at room temperature. The solvent was removed and the residue was purified by silica gel column chromatography (n-hexane:ethyl acetate=1:4) to afford 4.4 g (yield: 80%) of the desired compound as a racemic mixture.

Preparation Example 3

Preparation of (2R,3R,4S)-2-methyl-2-dimethoxymethyl-3-hydroxy-4-amino-3,4-dihydro-2H-1-benzopyran and (2R,3S,4R)-2-methyl-2-dimethoxymethyl-3-hydroxy-4-amino-3,4-dihydro-2H-1-benzopyran (Step 1) Preparation of (2R)-2-methyl-2-dimethoxymethyl-3,4-epoxy-3,4-dihydro-2H-1-benzopyran To a solution of 400 mg (1.82 mmol) of (2R)-2-methyl-2-dimethoxymethyl-2H-1-benzopyran dissolved in 1 ml of DMSO was added 82 ul of distilled water. The reaction mixture was allowed to cool to 0° C., and to the mixture was added 647 mg of N-bromosuccinimide slowly. After 30 min, 1 ml of water was added to the mixture and the mixture was extracted with ethyl acetate. The organic layer was dried over anhydrous magnesium sulfate, filtered and concentrated under reduced pressure. The residue was dissolved in 1 ml of dioxane-water (3:1) and 146 mg of NaOH was added to the mixture. The reaction mixture was stirred for 24 min at room temperature and extracted with ethyl acetate. The organic layer was dried over anhydrous magnesium sulfate, filtered and concentrated under reduced pressure. The residue was purified by silica gel column chromatography (n-hexane:ethyl acetate=10:1) to afford 358 mg (yield: 83%) of the desired compound as a racemic mixture.

(Step 2) Preparation of (2R,3R,4S)-2-methyl-2-dimethoxymethyl-3-hydroxy-4-amino-3,4-dihydro-2H-1-benzopyran and (2R,3S,4R)-2-methyl-2-dimethoxymethyl-3-hydroxy-4-amino-3,4-dihydro-2H-1-benzopyran 560 mg (2.37 mmol) of the epoxide compound prepared in the step was dissolved in 20 ml of the saturated ammonia ethanol and the reaction mixture was stirred for 7 days at room temperature. The solvent was removed and the residue was purified by silica gel column chromatography (n-hexane:ethyl acetate=1:2) to afford 340 mg (yield: 57%) of the desired compound as a racemic mixture.

Preparation Example 4

Preparation of (2R,3R,4S)-6-nitro-2-methyl-2-hydroxymethyl-3-hydroxy-4-amino-3,4-dihydro-2H-1-benzopyran and (2R,3S,4R)-2-methyl-2-hydroxymethyl-3-hydroxy-4-amino-3,4-dihydro-2H-1-benzopyran (Step 1) Preparation of (2R)-6-nitro-2-methyl-2-hydroxymethyl-3,4-epoxy-3,4-dihydro-2H-1-benzopyran The reaction with 708 mg (3.20 mol) of (2R)-6-nitro-2-methyl-2-hydroxymethyl-2H-1-benzopyran in place of (2R)-6-nitro-2-methyl-2-dimethoxymethyl-2H-1-benzopyran as a starting material, was performed by the same method to the step 1 of preparation example 1. The residue was purified by silica gel column chromatography (n-hexane:ethyl acetate=2:1) to afford 625 mg (yield: 82%) of the desired compound as a racemic mixture.

(Step 2) Preparation of (2R,3R,4S)-6-nitro-2-methyl-2-hydroxymethyl-3-hydroxy-4-amino-3,4-dihydro-2H-1-benzopyran and (2R,3S,4R)-2-methyl-2-hydroxymethyl-3-hydroxy-4-amino-3,4-dihydro-2H-1-henzopyran 625 mg (2.63 mmol) of the epoxide compound prepared in the step 1 was dissolved in 10 ml of the saturated ammonia ethanol and the reaction mixture was stirred for 7 days at room temperature. The solvent was removed and the residue was purified by silica gel column chromatography (n-hexane:ethyl acetate=1:5) to afford 328 mg (yield: 49%) of the desired compound as a racemic mixture.

Preparation Example 5

Preparation of (2R,3R,4S)-6-nitro-2-methyl-2-methoxymethyl-3-hydroxy-4-amino-3,4-dihydro-2H-1-benzopyran and (2R,3S,4R)-2-methyl-2-methoxymethyl-3-hydroxy-4-amino-3,4-dihydro-2H-1-benzopyran (Step 1) Preparation of (2R)-6-nitro-2-methyl-2-methoxymethyl-3,4-epoxy-3,4-dihydro-2H-1-benzopyran The reaction with 580 ml g (2.47 mmol) of (2R)-6-nitro-2-methyl-2-methoxymethyl-2H-1-benzopyran in place of (2R)-6-nitro-2-methyl-2-dimethoxymethyl-2H-1-benzopyran as a starting material, was performed by the same method to the step 1 of preparation example 1. The residue was purified by silica gel column chromatography (n-hexane:ethyl acetate=2:1) to afford 328 mg (yield: ethyl 98% of the desired compound as a racemic mixture.

Step 2) Preparation of 2R,3R,4S)-6-nitro-2 -methyl-2-methoxymethyl-3-hydroxy-4-amino-3,4-dihydro-2H-1-benzopyran and (2R,3S,4R)-2-methyl-2-methoxymethyl-3-hydroxy-4-amino-3,4-dihydro-2H-1-benzopyran 607 mg (2.42 mmol) of the epoxide compound prepared in the step 1 was dissolved in 10 ml of the saturated ammonia ethanol and the reaction mixture was stirred for 7 days at room temperature. The solvent was removed and the residue was purified by silica gel column chromatography (n-hexane:ethyl acetate=1:4) to afford 345 mg (yield: 53%) of the desired compound as a racemic mixture.

Preparation Example 6

Preparation of (2S,3S,4R)-6-cyano-2-methyl-2-dimethoxymethyl-3-hydroxy-4-amino-3,4-dihydro-2H-1-benzopyran The reaction with 1.2 g (4.90 mmol) of (2S)-6-cyano-2-methyl-2-dimethoxymethyl-2H-1-benzopyran in place of (2R)-6-nitro-2-methyl-2-dimethoxymethyl-2H-1-benzopyran as a starting material, was performed by the same method to the step and step 2 of preparation example 1. The residue was purified by silica gel column chromatography (n-hexane:ethyl acetate=4:1) to afford 0.65 g (yield: 48%) of the desired compound of (2S,3S,4R) stereochemistry.

Preparation Example 7

Preparation of (2S,3R,4S)-6-cyano-2-methyl-2-dimethoxymethyl-3-hydroxy-4-amino-3,4-dihydro-2H-1-benzopyran The reaction was performed by the same method to the preparation example 6. The residue was purified by silica gel column chromatography (n-hexane:ethyl acetate 4:1) to afford 0.30 g (yield: 22%) of the desired compound of (2S,3R,4S) stereochemistry.

Preparation Example 8

Preparation of (2S,3S,4R)-6-bromo-2-methyl-2-dimethoxymethyl-3-hydroxy-4-amino-3,4-dihydro-2H-1-benzopyran The reaction with 1.6 g (5.35 mmol) of (2S)-6-bromo-2-methyl-2-dimethoxymethyl-2H-1-benzopyran in place of (2R)-6-nitro-2-methyl-2-dimethoxymethyl-2H-1-benzopyran as a starting material, was performed by the same method to the step 1 and step 2 of preparation example 1. The residue was purified by silica gel column chromatography (n-hexane:ethyl acetate=1:4) to afford 1.28 g (yield: 72%) of the desired compound of (2S,3S, 4R) stereochemistry.

Preparation Example 9

Preparation of (2S,3S,4R)-4-amino-6-methanesulfonyloxy-4-dihydro-3 -hydroxy-2-methyl-2-dimethoxymethyl -2H-1-benzopyran The reaction with 2.52 g (8.45 mmol) of (2S)-6-methanesulfonyloxy-2-methyl-2-dimethoxymethyl-2H-1-benzopyran in place of (2R)-6-nitro-2-methyl-2-dimethoxymethyl-2H-1-benzopyran as a starting material, was performed by the same method to the step 1 and step 2 of preparation example 1. The residue was purified by silica gel column chromatography (n-hexane:ethyl acetate 1:5) to afford 1.74 g (yield: 62%) of the desired compound of (2S,3S,4R) stereochemistry.

Preparation Example 10

Preparation of (2R,3S,4R)-4-amino-6-methanesulfonyloxy-3,4-dihydro-3-hydroxy-2-methyl-2-dimethoxymethyl-2H-1-benzopyran The reaction with 0.79 g (2.65 mmol) of (2R)-6-methanesulfonyloxy-2-methyl-2-dimethoxymethyl-2H-1-benzopyran in place of (2R)-6-nitro-2-methyl-2-dimethoxymethyl-2H-1-benzopyran as a starting material, was performed by the same method to the step 1 and step 2 of preparation example 1. The residue was purified by silica gel column chromatography (n-hexane:ethyl acetate=1:5) to afford 0.60 g (yield: 68%) of the desired compound of (2R,3S,4R) stereochemistry.

Preparation Example 11

Preparation of (2S,3S,4R)-2-methyl-2-([,3]dioxolan-2-yl)-6-nitro-3-hydroxy-4-amino-3,4-dihydro-2H-1-benzopyran (Step 1) Preparation of (2S)-2-methyl-2-([1,3]dioxolan-2-yl)-6-nitro-2H-1-benzopyran 1 g (3.77 mmol) of (2S)-2-methyl-2-dimethoxymethyl-6-nitro-2H-1-benzopyran, 0.63 ml (11.31 mmol) of ethylene glycol and 71.7 mg (0.377 mol) of p-toluenesulfonic acid were dissolved in 20 ml of toluene, and the reaction mixture was refluxed for 5 hours. The reaction mixture was washed with saturated aqueous NaHCO solution and extracted with water and ethyl acetate. The organic layer was dried over anhydrous magnesium sulfate, filtered and concentrated under reduced pressure. The residue was purified by silica gel column chromatography (n-hexane:ethyl acetate=6:1) to afford 0.93 g (yield: 93%) of the desired compound.

¹H NMR (CDCl₃, 200 MHz) δ6 1.48(s, 3H), 3.91–3.97 (m, 4H), 4.95(s, 1H), 5.73(d, 1H), 6.49(d, 1H), 6.83(d, 1H), 7.86(d, 1H), 8.01(dd, 1H)

(Step 2) Preparation of (2S,3S,4R)-2-methyl-2-([1,3]dioxolan-2-yl)-6-nitro-3-3,1-epoxy-3,4-dihydro-2H-1-benzopyran Into 100 ml one-neck flask was pouted 25.6 (14.08 mmol) of 0.55M aqueous NaOCl solution and 9.6 ml of 0.05M Na₂HPO₄, and the mixture was allowed to cool to 0° C. To the mixture were added 0.93 g (3.52 mmol) of the compound prepared in the step 1 and 96.22 mg (0.176 mmol) of Jacobsen's catalyst (S, S) in 7 ml of methylene chloride.

The reaction mixture was stirred for 8 hours at room temperature and filtered on cellite pad to remove Jacobsen's catalyst. The methylene chloride layer was washed with brine, dried over Na₂SO₄, filtered and concentrated under reduced pressure. The residue was purified by silica gel column chromatography (n-hexane:ethyl acetate=4:1) to afford 470 mg (yield: 48%) of the desired compound.

¹H NMR (CDCl₃, 200 MHz) 67 1.57(s, 3H), 3.73(d, 1H), 3.80–3.90(m, 4H), 4.02(d, 1H), 4.96(s, 1H), 6.88(d, 1H), 8.13(dd, 1H), 8.29(d, 1H)

(Step 3) Preparation of (2S,3S,4R)-2-methyl-2-([1,3]dioxolan-2-yl)-6-nitro-3-hydroxy-4-amino-3,4-dihydro-2H-1-benzopyran To a solution of 40 mg (1.68 mmol) of the compound prepared in the step 2 dissolved in 15 ml of ethanol was added 2.3 ml (16.3 mmol) of 25% NH₄OH solution, and the reaction mixture was stirred for 5 (days at 25° C. Ethanol was removed under reduced pressure. The residue was extracted with ethyl acetate, washed with brine, dried over Na₂SO₄, filtered and concentrated under reduced pressure. The residue was purified by silica gel column chromatography (n-hexane:ethyl acetate=1:3) to afford 440 mg (yield: 80%) of the desired compound.

Preparation Example 12

Preparation of (2S,3S,4R)-2-methyl-2-([1,3]dioxan-2-yl)-6-nitro-3-hydroxy-4-amino-3,4-dihydro-2H-1-benzopyran (Step 1) Preparation of (2S)-2-methyl-2-([1,3]dioxan-2-yl)-6-nitro-2H-1-benzopyran -

The reaction of 1 g (3.77 mmol) of (2S)-2-methyl-2-dimethoxymethyl-6-nitro-2H-1-benzopyran with 2.73 ml of 1,3-propanediol, was performed by the same method to the step 1 of preparation example 11. The residue was purified by silica gel column chromatography (n-hexane:ethyl acetate=6:1) to afford 1 g (yield: 96%) of the desired compound.

(Step 2) Preparation of (2S,3S,4S)-2-methyl-2-([1,3]dioxan-2-yl)-6-nitro-3,4-epoxy-3,4-dihydro-2H-1-benzopyran The reaction was performed by the same method of the step 2 of preparation example 11 except using the compound prepared in the above step 1 as a starting material. The residue was purified by silica gel column chromatography (n-hexane:ethyl acetate=4:1) to afford 0.57 g (yield: 54%) of the desired compound.

(Step 3) Preparation of (2S,3S,4R)-2-methyl-2-([1,3]dioxan-2-yl)-6-nitro-3-hydroxy-4-amino-3,4-dihydro-2H-1-benzopyran The reaction was performed by the same method of the step 3 of preparation exmaple 11 except using the compound prepared in the above step 2 as a starting material. The residue was purified by silica gel column chromatography (n-hexane:ethyl acetate=1:3) to afford 0.46 g (yield: 76%) of the desired compound.

Preparation Example 13

Preparation of (2S,3S,4R)-2-methyl-2-([1,3]-5,5-dimethyldioxan-2-yl)-6-nitro-3-hydroxy-4-amino-3, 4-dihydro-2H-1-benzopyran (Step 1) Preparation of (2S)-2-methyl-2-([1,3]-5,5-dimethyldioxan-2-yl)-6-nitro-2H-1-benzopyran The reaction was performed by the same method to the step 1 of preparation example 11 except using 1 g (3.77 mmol) of (2S)-2-methyl-2-dimethoxymethyl-6-nitro-2H-1-benzopyran and 2,80 ml of 2,2-dimethyl- 1,3-propanediol as a starting material. The residue was purified by silica gel column chromatography (n-hexane:ethyl acetate=6:1) to afford 1.01 g (yield: 88%) of the desired compound.

(Step 2) Preparation of (2S,3S,4S)-2-methyl-2-([3]-5,5-dimethyldioxan-2-yl)-6-nitro-3,4-epoxy-3,4-dihydro-2H-1-benzopyran The reaction was performed by the same method of the step 2 of preparation exmaple 11 except using the compound prepared in the above step 1 as a starting material. The residue was purified by silica gel column chromatography (n-hexane:ethyl acetate=4:1) to afford 0.62 g (yield: 58%) of the desired compound.

(Step 3) Preparation of (2S,3S,4R)-2-methyl-2-([1,3]-5,5-dimethyldioxan-2-yl)-6-nitro-3-hydroxy-4-amino-3,4-dihydro-2H-1-benzopyran The reaction was performed by the same method of the step 3 of preparation example 11 except using the compound prepared in the above step 2 as a starting material. The residue was purified by silica gel column chromatography (n-hexane:ethyl acetate=1:3) to afford 0.53 g (yield: 82%) of the desired compound.

Preparation Example 14

Preparation of (2S,3S,4R)-2-methyl-2-diethoxymethyl-6-nitro-3-hydroxy-4-amino-3,4-dihydro-2H-1-benzopyran (Step 1) Preparation of (2S)-2-methyl-2-diethoxymethyl-6-nitro-2H-1-benzopyran The reaction was performed by the same method to the step 1 of preparation example 11 except using 1 g (3.77 mmol) of (2S)-2-methyl-2-dimethoxymethyl-6-nitro-2H-1-benzopyran and 3.0 ml of ethanol as a starting material. The residue was purified by silica gel column chromatography (n-hexane:ethyl acetate=6:1) to afford 1.01 g (yield: 91%) of the desired compound.

(Step 2) Preparation of (2S,3S,4S)-2-methyl-2-diethoxymethyl-6-nitro-3,4-epoxy-3,4-dihydro-2H-1-benzopyran The reaction was performed by the same method of the step 2 of preparation example 11 except using the compound prepared in the above step 1 as a starting material. The residue was purified by silica gel column chromatography (n-hexane:ethyl acetate=4:1) to afford 0.71 g (yield: 67.) of the desired compound.

(Step 3) Preparation of (2S,3S,4R)-2methy-2-diethoxymethyl-6-nitro-3-hydroxy-4-amino-3,4-dihydro-2H-1-benzopyran The reaction was performed by the same method of the step 3 of preparation example 11 except using the compound prepared in the above step 2 as a starting material. The residue was purified by silica gel column chromatography (n-hexane:ethyl acetate=1:3) to afford 0.65 g (yield: 86%) of the desired compound.

Preparation Example 15

Preparation of (2S,3S,4R)-2-methyl-2-dimethoxymethyl-6-methoxycarbonyl-3-hydroxy-4-amino-3,4-dihydro-2H-1-benzopyran The reaction was performed by the same method to the step 1 and step 2 of preparation example 1 except using 1.41 g (5.32 mmol) of (2S)-2-methyl-2-dimethoxy methyl-6-methoxycarbonyl-2H-1-benzopyran as a starting material. The residue was purified by silica gel column chromatography (n-hexane:ethyl acetate=1:4) to afford 0.86 g (yield: 52%) of the desired compound.

Preparation Example 16

Preparation of (2R,3S,4R)-2-methyl-2-dimethoxymethyl-6-methoxycarbonyl-3-hydroxy-4-amino-3,4-dihydro-2H-1-benzopyran The reaction was Performed by the same method to the step 1 and step 2 of preparation example 1 except using 1.27 g (4.79 mmol) of (2R)-2-methyl-2-dimethoxy methyl-6-methoxycarbonyl-2H-1-benzopyran as a starting material. The residue was purified by silica gel column chromatography (n-hexane:ethyl acetate=1:4) to afford 0.85 g (yield: 57%) of the desired compound.

Preparation Example 17

Preparation of (3S,4R)-2-methyl-2-dimethoxymethyl-8-nitro-3-hydroxy-4-amino-3,4-dihydro-2H-1-benzopyran The reaction was performed by the same method to the step 1 and step 2 of preparation example 1 except using 1.82 g (6.86 mmol) of (2S)-2-methyl-2-dimethoxy methyl-8-nitro-2H-1-benzopyran as a starting material. The residue was purified by silica gel column chromatography (n-hexane:ethyl acetate=1:4) to afford 1.31 g (yield: 64%) of the desired compound.

EXAMPLES

The compounds of formula 1 were prepared by the following examples.

Example 1

Preparation of (2R,3R,4S)-N"-cyano-N-(6-nitro-3,4-dihydro-3-hydroxy-2-methyl-2-dimethoxymethyl-2H-benzopyran-4-yl)-N'-(4-chlorophenyl)guanidine To a solution of 508 mg of N-cayno-N'-(4-chlorophenyl)thiourea sodium salt and 500 mg (1.68 mmol) of the aminoalcohol compound prepared in the preparation example 1 dissolved in 5 ml of DMF was added 418 mg of 1-[3-(dimethylamino)propyl]-2-ethylcarbodiimide hydrochloride. The reaction mixture was stirred for 5 hours at room temperature, and extracted with ethyl acetate (30 ml×2) after acidifying the mixture by adding 10 ml of 1N HCl. The organic layer was washed with water and brine, dried over anhydrous magnesium sulfate and concentrated under reduced pressure. The residue was purified by silica gel column chromatography (n-hexane:ethyl acetate=1:1) to afford 260 mg (yield: 339') of the desired compound of (2R,3R,4S) stereochemistry.

$^1$H NMR (DMSO-d$_6$, 300 MHz) δ1.35(s, 3H), 3.36(d, 6H), 3.85(t, 1H, 4.59(s, 1H), 5.10(t, 1H), 5.97(s, 1H), 6.3(d, 1H), 7.35(dd, 4H), 7.62(d, 1H), 8.01(d, 2H), 9.44(s, 1H).

Example 2

Preparation of (2R,3S,4R)-N"-cyano-N-(6-nitro-3,4-dihydro-3-hydroxy-2-methyl-2-dimethoxymethyl-2H-benzopyran-4-yl)-N'-(4-chlorophenyl)guanidine The reaction was performed by the same method to the example 1. The residue was purified by silica gel column chromatography (n-hexane:ethyl acetate=1:4) to afford 200 mg (yield: 25%) of the desired compound of (2R,3S, 4R) stereochemistry.

$^1$H NMR (DMSO-d$_6$, 300 MHz) 67 1.23(s, 3H), 3.42(d, 6H), 4.07(t, 1H), 4.48(s, 1H), 4.99(t, 1H), 5.80(s, 1H), 6.96(d, 1H), 7.36(dd, 4H), 7.76(s, 1H), 8.03(s, 2H), 9.48(s, 1H)

Example 3

Preparation of (2R,3R,4S)-N"-cyano-N-(6-nitro-3,4-dihydro-3-hydroxy-2-methyl-2-dimethoxymethyl-2H-benzopyran-4-yl)-N'-(3-chlorophenyl)guanidine To a solution of 508 mg of N-cyano-N'-(4-chlorophenyl)thiourea sodium salt and 500 mg of the aminoalcohol compound prepared in the preparation example 1 dissolved in 5 ml of DMF was added 418 mg of 1-[3-(dimethylamino)propyl]-2-ethylcarbodiimide hydrochloride. The reaction mixture was stirred for 6 hours at room temperature, and extracted with ethyl acetate (30 ml×2) after acidifying the mixture by adding 10 ml of 1N HCl. The organic layer was washed with water and brine, dried over anhydrous magnesium sulfate and concentrated under reduced pressure. The residue was purified by silica gel column chromatography (n-hexane:ethyl acetate=1:1) to afford 230 mg (yield: 29%) of the desired compound of (2R,3R,4S) stereochemistry.

$^1$H NMR (DMSO-d$_6$, 300 MHz) δ1.35(s, 3H), 3.38(d, 6H), 3.88(s, 3H), 4.59(s, 1H), 5.11(s, 1H), 5.97(s, 1H), 6.94(d, 1H), 7.28(m, 4H), 7.79(d, 1H), 8.04(m, 2H), 9.49(s, 1H)

Example 4

Preparation of (2R,3S,4R)-N"-cyano-N-(6-nitro-3,4-dihydro-3-hydroxy-2-methyl-2-dimethoxymethyl-2H-benzopyran-4-yl)-N'-(3-chlorophenyl)guanidine The reaction was performed by the same method to the example 3. The residue was purified by silica gel column chromatography (n-hexane:ethyl acetate=1:4) to afford 200 mg (yield: 25%) of the desired compound of (2R,3S, 4R) stereochemistry.

$^1$H NMR (DMSO-d$_6$, 300 MHz) δ1.23(s, 3H), 3.42(d, 5H), 4.08(t, 1H), 4.49(s, 1H), 4.99(t, 1H), 6.98(d, 1H), 7.30(m, 4H), 7.91(d, 1H), 8.04(d, 2H), 9.6(s, 1H)

Example 5

Preparation of (2R,3R,4S)-N"-cyano-1-(6-nitro-3,4-dihydro-3-hydroxy-2-methyl-2-dimethoxymethyl-2H-benzopyran-4-yl)-N'-(4-nitrophenyyl)guanidine To a solution of 532 mg of N-cyano-N'-(4-nitrophenyl)thiourea sodium salt and 500 mg of the aminoalcohol compound prepared in the preparation example 1 dissolved in 5 ml of DMF was added 418 mg of 1-[3-(dimethylamino)propyl-2-ethylcarbodiimide hydrochloride. The reaction mixture was stirred for 6 hours at room temperature, and extracted with ethyl acetate (30 ml×2) after acidifying the mixture by adding 10 ml of 1N HCl. The organic layer was washed with water and brine, to dried over anhydrous magnesium sulfate and concentrated under reduced pressure. The residue was purified by silica gel column chromatography (n-hexane:ethyl acetate=1:1) to afford 210 mg (yield: 26%) of the desired compound of (2R,3R,4S) stereochemistry.

$^1$H NMR (DMSO-d$_6$, 300 MHz) δ1.36(s, 3H), 3.38(d, 6H), 3.88(t, 1H), 4.60(s, 1H), 5.12(t, 1H) 6.2(s, 1H), 6.97(d, 1H), 7.48(d, 1H), 8.04(dd, 1H), 8.11(s, 1H), 8.20(d, 2H), 8.33(d, 1H), 10.07(s, 1H)

Example 6

Preparation of (2R,3R,4S)-N"-cyano-N-(6-nitro-3,4-dihydro-3-hydroxy-2-methyl-2-dimethoxymethyl-2H-benzopyran-4-yl )-N'-(3-trifluoromethylphenyl)guandine To a solution of 500 mg of N-cyano-N'-(4 -trifluoromethylphenyl)thiourea sodium salt and 500 mg of the aminoalcohol compound prepared in the preparation example 1 dissolved in 5 ml of DMF was added 418 mg of 1-[3-(dimethylamino))propyl]-2-ethylcarbodiimide hydrochloride. The reaction mixture was stirred for 5 hours at room temperature, and extracted with ethyl acetate (30 ml×2) after acidifying the mixture by adding 10 ml of 1N HCl. The organic layer was washed with water and brine, dried over anhydrous magnesium sulfate and concentrated under reduced pressure. The residue was purified by silica gel column chromatography (n-hexane:ethyl acetate=1:1) to afford 250 mg,(yield: 29%) of the desired compound of (2R,3R,4S) stereochemistry.

$^1$H NMR (DMSO-d$_6$, 300 MHz) δ1.34(s, 3H), 3.38(d, 6H), 3.38(t, 1H), 4.59(s, 1H), 5.10(t, 1H), 6.0(s, 1H), 6.94(d, 1H), 7.52(d, 1H), 7.57(m, 3H), 7.86(d, 1H), 8.02(dd, 1H), 8.09(s, 1H)

Example 7

(2R,3S,4R)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine The reaction was performed by the same method to the example 6. The residue was purified by silica gel column chromtography (n-hexane:ethyl acetate=1) to afford 200 mg (yield: 23%) of the desired compound of (2R,3S, 4R) stereochemistry.

$^1$H NMR (DMSO-d$_6$, 300 MHz) δ1.23(s, 3H), 3.43(d, 6H), 4.08(t, 1H), 4.49(s, 1H), 5.01(t, 1H), 5.85(s, 1H), 6.98(d, 1H), 7.49(d, 1H), 7.60(m, 3H), 8.03(m, 3H), 9.7(s, 1H)

Example 8

Preparation of (2R,3R,4S)-N"-cyano-N-(6-nitro-3,4-dihydro-3-hydroxy-2-methyl-2-dimethoxymethyl-2H-benzopyran-4-yl)-N'-(4-methoxyphenyl)guanidine To a solution of 500 mg of N-cyano-N'-(4-methoxyphenyl)thiourea sodium salt and 500 mg of the aminoalcohol compound prepared in the preparation example 1 dissolved in 5 ml of DMF was added 418 mg of 1-[3-(dimethylamino)propyl]-2-ethylcarbodiimide hydrochloride. The reaction mixture was stirred for 5 hours at room temperature, and extracted with ethyl acetate (30 ml×2) after acidifying the mixture by adding 10 ml of 1N HCl. The organic layer was washed with water and brine, dried over anhydrous magnesium sulfate and concentrated under reduced pressure. The residue was purified by silica gel chromatography (n-hexane:ethyl acetate=1:1) to afford 49 mg (yield: 6%) of the desired compound of (2R,3R,4S) stereochemistry.

$^1$H NMR (DMSO-d$_6$, 300 MHz), δ1.24(s, 3H), 3.35(d, 6H), compound of (2R,2R,4S) stereochemistry.

$^1$H NMR (DMSO-$_6$, 300 MHz) δ1.24(s, 3H), 3.55(d, 6H), 3.70(s, 3H), 4.08(t, 1H), 4.45(s, 1H), 5.64(d, 1H), 5.78(t, 1H), 6.93 (m, 3H), 7.24(d, 2H), 8.02(d, 2H), 8.17(s, 1H), 9.59(s, 1H)

Example 9

Preparation of (2R,3S,4R)-N"-cyano-N-(6-nitro-3,4-dihydro-3-hydroxy-2-methyl-2-dimethoxymethyl-2H-benzopyran-4-yl)-N'-(4-methoxyphenyl)guanidine The reaction was performed by the same method to the example 8. The residue was performed by silica gel chromatography (n-hexane:ethyl acetate=1:1) to afford 190 mg (yield: 24%) of the desired compound of (2R,3S, 4R) stereochemistry.

$^1$H NMR (DMSO-$_6$, 300 MHz) δ1.33(s, 3H), 3.38(d, 6H), 3.72(s, 3H), 3.78(t, 1H), 4.58(s, 1H), 5.10(t, 1H), 5.88(s, 1H), 6.19(d, 3H), 7.20(d, 3H), 7.20(d, 3H), 7.97(s, 1H), 9.14(s, 1H)

Example 10

Preparation of (2S,3R,4S)-N"-cyano-N-(6-nitro-3,4-dihydro-3-hydroxy-2-methyl-2-dimethoxymethyl-2H-benzopyran-4-yl)-N'-(4-chlorophenyl)guanidine To a solution of 508 mg of N-cyano-N'-(4-chlorophenyl)thiourea sodium salt and 500 mg of the aminoalcohol compound prepared in the preparation example hydrochloride. The reaction mixture was stirred for 5 hours at room temperature, and extracted with ethyl acetate (30 ml×2) after acidifying the mixture by adding 10 ml of 1N HCl. The organic layer was washed with water and brine, dried over anhydrous magnesium sulfate and concentrated under reduced pressure. The residue was purified by silica gel chromatography (n-hexane:ethyl acetate=1:1) to afford 260 mg (yield: 33%) of the desired compound of (2S, 3R,4S) stereochemistry.

$^1$H NMR (DMSO-d$_6$, 300 MHz) δ1.35(s, 3H), 3.37(d, 6H), 3.85(t, 1H), 4.59(s, 1H), 5.11(t, 1H), 5.91(s, 1H), 6.93(d, 1H), 7.35(dd, 4H), 7.63(d, 1H), 8.01(d, 2H), 9.44(s, 1H)

Example 11

Preparation of (2S,3S,4R)-N"-cyano-N-(6-nitro-3,4-dihydro-3-hydroxy-2-methyl-2-dimethoxymethyl-2H-benzopyran-4-yl)-N'-(4-chlorophenyl)guanidine The reaction was performed by the same method to the example 10. The residue was purified by silica gel chromatography (n-hexane:ethyl acetate=1:1) to afford 200 mg (yield: 25%) of the desired compound of (2S,3S,4R) stereochemistry.

$^1$H NMR (DMSO-$d_6$, 300 MHz) δ1.23(s, 3H), 3.43(d, 6H), 4.05(t, 1H), 4.48(s, 1H), 4.99(t, 1H), 5.81(s, 1H), 6.97(d, 1H), 7.37(dd, 4H), 7.76(s, 1H), 8.03(s, 2H), 9.49(s, 1H)

Example 12

Preparation of (2S,3R,4S)-N"-cyano-N-(6-nitro-3,4-dihydro-3-hydroxy-2-methyl-2-dimethoxymethyl-2H-benzopyran-4-yl)-N'-(3-chlorophenyl)guanidine The reaction was performed by the same method to the example 10. The residue was purified by silica gel chromatography (n-hexane:ethyl acetate=1:1) to afford 188 mg (yield: 24%) of the desired compound of (2S,3R, 4S) stereochemistry.

$^1$H NMR (DMSO-$d_6$, 300 MHz) δ1.35(s, 3H), 3.43(d, 6H) 3.88(t, 1H), 4.60(s, 1H), 5.11(t, 1H), 5.97(s, 1H), 6.95(d, 1H), 7.17(d, 1H), 7.25(d, 1H), 7.34(d, 2H), 7.79(d, 1H), 8.03(m, 2H), 9.49(s, 1H)

Example 13

Preparation of (2S,3S,4R)-N"-cyano-N-(6-nitro-3,4-dihydro-3-hydroxy-2-methyl-2-dimethoxymethyl-2H-benzopyran-4-yl)-N'-(3-chlorophenyl)guanidine The reaction was performed by the same method to the example, 12. The residue was purified by silica gel chromatography (n-hexane:ethyl acetate=1:1) to afford 270 mg (yield: 34%) of the desired compound of (2S,3S,4R) stereochemistry.

$^1$H NMR (DMSO-$d_6$, 300 MHz) δ1.18(s, 3H), 3.43(d, 6H), 4.09(t, 1H), 4.49(s, 1H), 5.00(t, 1H), 5.85(s, 1H), 6.98(d, 1H), 7.29(d, 1H), 7.37(d, 1H), 7.40(m, 2H), 7.91(d, 1H), 8.05(m, 2H)

Example 14

Preparation of (2S,3R,4S)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine The reaction was performed by the same method to the example 10 except using 582 mg of N-cyano-N'-(3-trifluoromethylphenyl)thiourea sodium salt and 500 mg of the aminoalcohol compound prepared in the preparation example 2. The residue was purified by silica gel chromatography (n-hexane:ethyl acetate=1:1) to afford 220 mg (yield: 26%) of the desired compound of (2S,3R, 4S) stereochemistry.

$^1$H NMR (DMSO-$d_6$, 300 MHz) δ1.34(s, 3H), 3.43(d, 6H), 3.88(t, 1H), 4.60(s, 1H), 5.11(t, 1H), 5.95(s, 1H), 6.95(d, 1H), 7.45(d, 1H), 7.57(m, 3H), 7.88(d, 1H), 8.03(dd, 1H), 8.10(s, 1H), 9.62(s, 1H)

Example 15

Preparation of (2S,3S,4R)-N"-cyano-N-(6-nitro-3,4-dihydro-3-hydroxy-2-methyl-2-dimethoxymethyl-2H-benzopyran-4-yl)-N'-(3-trifluoromothyl phenyl)guanidine The reaction was performed by the same method to the example 14. The residue was purified by silica gel chromatography (n-hexane:ethyl acetate=1:1) to afford 320 mg (yield: 37%) of the desired compound of (2S,3S, 4R) stereochemistry.

$^1$H NMR (DMSO-$d_6$, 300 MHz) δ1.24(s,3 H), 3.43(d, 6H), 4.08(t, 1H), 4.49(s, 1H), 5.01(t, 1H), 5.82(s, 1H), 6.98(d, 1H), 7.47 (d, 1H), 7.57 (m, 3H), 7.98(d, 1H), 8.03 (m, 2H), 9.67(s, 1H)

Example 16

Preparation of (2S,3R,4S)-N"-cyano-N-(6-nitro-3,4-dihydro-3-hydroxy-2-methyl-2-dimethoxymethyl-2-benzopyran-4-yl)-N'-(4-methoxyphenyl)guanidine The reaction was performed by the same method to the example 10 except using 500 mg of N-cyano-N'-(4-methoxyphenyl)thiourea sodium salt and 500 mg of the aminoalcohol compound prepared in the preparation example 2. The residue was purified by silica gel chromatography (n-hexane:ethyl acetate=1:1) to afford 170 mg (yield: 21%) of the desired compound of (2S,3R, 4S) stereochemistry.

$^1$H NMR (DMSO-$d_6$, 300 MHz) δ1.33(s, 3H), 3.36(d, 6H), 3.72(s, 3H), 3.86(t, 1H), 4.58(s, 1H), 5.09(t, 1H), 5.88(s, 1H), 6.91(d, 3H), 7.20(d, 3H), 7.97(s, 1H), 8.00(d, 1H)

Example 17

Preparation of (2S,3S,4R)-N"-cyano-N-(6-nitro-3,4-dihydro-3-hydroxy-2-methyl-2-dimethoxymethyl-2H-benzopyran-4-yl)-N'-(4-methoxyphenyl)guanidine The reaction was performed by the same method to the example 16. The residue was purified by silica gel chromatography (n-hexane:ethyl acetate=1:1) to afford 270 mg (yield: 34%) of the desired compound of (2S,3S,4R) stereochemistry.

$^1$H NMR (DMSO-$d_6$, 300 MHz) δ1.22(s, 3H), 3.38(d, 6H), 3.72(s, 3H), 4.06(t, 1H), 4.45(s, 1H), 4.99(t, 1H), 5.75(s, 1H), 6.93(t, 3H), 7.20(d, 2H), 7.35(s, 1H), 8.01(s, 1H), 8.03(d, 1H), 9.19(s, 1H)

Example 18

Preparation of (2R,3R,4S)-N"-cyano-N-(6-nitro-3,4-dihydro-3-hydroxy-2-methyl-2-dimethoxymethyl-2H-benzopyran-4-yl)-N'-(4-methylphenyl)guanidine The reaction was performed by the same method to the example 1 except using 465 mg of N-cyano-N'-(4-methylphenyl)thiourea sodium salt and 500 mg of the aminoalcohol compound prepared in the preparation example 2. The residue was purified by silica gel chromatography (n-hexane:ethyl acetate=1:1) to afford 158 mg (yield: 21%) of the desired compound of (2R,3R,4S) stereochemistry.

$^1$H NMR (DMSO-$d_6$, 300 MHz) δ1.34(s, 3H), 2.26(s, 3H), 3.37(d, 6H), 3.87(s, 1H), 4.59(s, 1H), 5.11(t, 1H), 5.93(s, 1H), 6.92(d, 1H), 7.16(s, 3H), 7.38(d, 1H), 8.00 (1H, 2H), 9.24(s, 1H)

Example 19

Preparation of (2R,3S,4R)-N"-cyano-N-(6-nitro-3,4-dihydro-3-hydroxy-2-methyl-2-dimethoxymethyl-2H-benzopyran-4-yl)-N'-(4-methylphenyl)guanidine The reaction was performed by the same method to the example 18. The residue was purified by silica gel chromatography (n-hexane:ethyl acetate=1:1) to afford 250 mg (yield: 33%) of the desired compound of (2R,3S,4R) stereochemistry.

¹H NMR (DMSO-d₆, 300 MHz) δ1.22(s, 3H), 2.26(s, 3H), 3.38(d, 6H), 4.06(t, 1H), 4.46(s, 1H), 4.99(t, 1H), 5.74(s, 1H), 6.95(d, 1H), 7.16(s, 3H), 7.53(s, 1H), 8.02(d, 2H), 9.28(s, 1H)

Example 20

Preparation of (2R,3R,4S)-N"-cyano-N-(6-nitro-3,4-dihydro-3-hydroxy-2-methyl-2-dimethoxymethyl-2H-benzopyran-4-yl)-N'-(4-methoxybenzyl)quanidine The reaction was performed by the same method to the example 1 except using 530 mg of N-cyano-N'-4-methoxybenzyl)thiourea sodium salt and 500 mg of the aminoalcohol compound prepared in the preparation example 1. The residue was purified by silica gel chromatography (n-hexane:ethyl acetate=1:1) to afford 134 mg (yield: 16%) of the desired compound of (2R,3R,4S) stereochemistry.

¹H NMR (CDCl₃, 300 MHz) δ1.47(s, 3H), 3.51(d, 6H), 3.77(s, 3H), 3.80(d, 2H), 4.44(t, 1H), 4.56(s, 1H), 5.32(m, 1H), 6.06(s, 1H), 6.40(d, 1H), 6.90(m, 3H), 7.12(m, 2H), 7.30(d, 1H), 8.00(dd, 1H), 8.03(s, 1H)

Example 21

Preparation of (2R,3S,4R)-N"-cyano-N-(6-nitro-3,4-dihydro-3-hydroxy-2-methyl-2-dimethoxymethyl-2H-benzopyran-4-yl)-N'-(4-methoxybenzyl)guanidine The reaction was performed by the same method to the example 20. The residue was purified by silica gel chromatography (n-hexane:ethyl acetate=1:1) to afford 140 mg (yield: 17%) of the desired compound of (2R,3S,4R) stereochemistry.

¹H NMR (CDCl₃, 300 MHz) δΣ1.32(s, 3H), 3.49(s, 6H), 3.58(t, 1H), 3.77(s, 3H), 4.04(d, 1H), 4.41(s, 1H), 4.65(s, 2H), 6.35(s, 1H), 6.88(dd, 4H), 7.26(d, 2H), 8.04(dd, 1H), 8.08(s, 1H)

Example 22

Preparation of (2R,3R, 4S)-N"-cyano-N-( 6-nitro-3, 4-dihydro-3-hydroxy-2-methyl-2-dimethoxymethyl-2H-benzopyran-4-yl)-N'-benzylguanidine The reaction was performed by the same method to the example except using 465 mg of N-cyano-N'-benzylthiourea sodium salt and 500 mg of the aminoalcohol compound prepared in the preparation example 1. The residue was purified by silica gel chromatography (n-hexane:ethyl acetare=1:1) to afford 260 mg (yield: 34%) of the desired compound of (2R,3R,4S) stereochemistry.

¹H NMR (DMSO-d₆, 300 MHz) δ1.24(s, 3H), 3.41(m, 1H), 3.44(d, 6H), 4.04(m, 1H), 4.51(s, 1H), 4.76(s, 2H), 5.70(s, 1H), 6.98(d, 1H), 7.32 (m, 4H), 8.03(m, 2H), 8.16(s, 1H)

Example 23

Preparation of (2R,3S,4R)-N"-cyano-N-(6-nitro-3,4-dihydro-3-hydroxy-2-methyl-2-dimethoxymethyl-2H-benzopyran-4-yl)-N'-benzylguanidine The reaction was performed by the same method to the example 22. The residue was purified by silica gel chromatography (n-hexane:ethyl acetate=1:1) to afford 200 mg (yield: 26%) of the desired compound of (2R,3S,4R) stereochemistry.

¹H NMR (DMSO-d₆, 300 MHz) δ1.26(s, 3H), 3.36(d, 6H), 3.44(d, 1H), 3.87(t, 1H)), 4.44(d, 21), 4.56(s, 2H), 5.02(t, 1H), 5.86(s, 1H), 6.94(d, 1H), 1.29(m, 4H), 7.75(t, 1H), 7.93(s, 1H), 7.99(dd, 1H)

Example 24

Preparation of (2S,3R,4S)-N'-cyano-N-(6-nitro-3,4-dihydro-3-hydroxy-2-methyl-2-dimethoxymethyl-2H-cenzopyran-4-yl)-N'-benzylguanidine The reaction was performed by the same method to the example 10 except using 508 mg of N-cyano-N'-benzylthiourea sodium salt and 500 mg of the aminoalcohol compound prepared in the preparation example 2. The residue was purified by silica gel chromatography (n-hexane:ethyl acetate=1:1) to afford 170 mg (yield: 22%) of the desired compound of (2S,3R,4S) stereochemistry.

¹H NMR (CDCl₃, 300 MHz) δ1.27(s, 3H), 3.48(d, 6H), 3.5(m, 1H), 4.02(d, 1H), 4.48(s, 1H), 4.75(s, 2H), 6.0(s, 1H), 6.72(s, 1H), 6.87(d, 1H), 7.30(m, 5H), 8.0(d, 1H), 8.02(s, 1H)

Example 25

Preparation of (2S,3S,4R)-N"-cyano-N-(6-nitro-3,4-dihydro-3-hydroxy-2-methyl-2-dimethoxymethyl-2H-benzopyran-4-yl)-N'-benzylguanidine The reaction was performed by the same method to the example 24. The residue was purified by silica gel chromatography (n-hexane:ethyl acetate=1:1) to afford 190 mg (yield: 25%) of the desired compound of (2S,3S, 4R) stereochemistry.

¹H NMR (CDCl₃, 300 MHz) δ1.31(s, 3H), 3.44(d, 6H), 3.5(m, 1H), 3.71(d, 1H), 4.47(s, 1H), 5.14(m, 2H), 5.69(s, 1H), 6.70(s, 1H), 6.58(d, 1H), 7.25(m, 5H), 8.0(d, 1H) 8.02(s, 1H)

Example 26

Preparation of (2R,3R,4S)-N"-cyano-N-(3,4-dihydro-3-hydroxy-2-methyl-2-dimethoxymethyl-2H-benzopyran-4-yl)-N'-(4-chlorophenyl)guanidine The reaction was performed by the same method to the example 1 except using 500 mg of N-cyano-N'-(4-chlorophenyl)thiourea sodium salt and 500 mg of the aminoalcohoL compound prepared in the preparation example 3. The residue was purified by silica gel chromatography (n-hexane:ethyl acetate=1:1) to afford 170 mg (yield: 23%) of the desired compound of (2R,3R,4S) stereochemistry.

¹H NMR (DMISO-d₆, 300 MHz) δ1.25(s, 3H), 3.37(d, 6H), 3.82(t, 1H), 4.52(s, 1H), 5.00(t, 1H), 5.45(s, 1H), 6.71(d, 1H), 6.90(t, 1H), 7.10(m, 2H), 7.24(d, 2H), 7.38(d, 2H) 7.54(d, 1H), 9.24(s, 1H)

Example 27

Preparation of (2R,3S,4R)-N"-cyano-N-(3,4-dihydro-3-dydroxy-2-methyl-2-dimethoxymethal-2H-benzopyran- 4-yl)-N'-(4-chlorophenyl)guanidine The reaction was performed by the same method to the example 26. The residue was purified by silica gel chromatography (n-hexane:ethyl acetate=1:1) to afford 190 mg (yield: 26%) of the desired compound of (2R,3S,4R) stereochemistry.

¹H NMR (DMSO-d₆, 300 MHz) δ1.16(s, 3H), 3.40(d, 6H), 4.01(t, 1H), 4.43(s, 1H), 4.92(t, 1H), 5.48(s, 1H), 6.72(d, 1H), 6.90(t, 1H), 7.15(m, 3H), 7.31(m, 4H), 7.67(s, 1H), 9.29(s, 1H)

Example 28

Preparation of (2R,3R,4S)-N"-cyano-N-(6-nitro-3,4-dihydro-3-hydroxy-2-methyl-2-hydroxymethyl-2H-benzopyran-4-yl)-N'-(4-chlorophenyl)guanidine The reaction was performed by the same method to the example except using 289 mg of N-cyano-N'-(4-chlorophenyl)thiourea sodium salt and 210 mg of the aminoalcohol compound prepared in the preparation example 4. The residue was purified by silica gel chromatography (n-hexane:ethyl acetate=1:1) to afford 40 mg (yield: 11%) of the desired compound Of (2R,3R,4S) stereochemistry.

¹H NMR (DMSO-d₆, 300 MHz) δ1.35 s, 3), 3.5 (m, 1H), 3.75(m, 1H), 4.95(t, 1H), 5.2(t, 1H), 6.0(s, 1H), 6.97(d, 1H), 7.4(m, 4), 7.7(d, 1H), 8.0(m, 2H), 9.51(s, 1H)

Example 29

Preparation of (2R,3S,4R)-N"-cyano-N-(6-nitro-3,4-dihydro-3-hydroxy-2-methyl-2-hydroxymethyl-2H-benzopyran-4-yl)-N'-(4-chlorophenyl)guanidine The reaction was performed by the same method to the example 28. The residue was purified by silica gel chromatography (n-hexane:ethyl acetate=1:1) to afford 40 mg (yield: 11%) of the desired compound of (2R,3S,4R) stereochemistry.

¹H NMR (DMSO-d₆, 300 MHz) δ1.2(s, 3H), 3.65 (m, 2H) 4.11(t, 1H), 5.08(t, 1H), 5.85(s, 1H), 7.01(d, 1H), 7.4(m, 4H), 7.9(d, 1H), 8.1(d, 2H), 9.58(s, 1H)

Example 30

Preparation of (2R,3R,4S)-N"-cyano-N-(6-nitro-3,4-dihydro-3-hydroxy-2-methyl-2-methoxymethy-2H-benzopyran-4-yl)-N'-(4-chlorophenyl)guanidine The reaction was performed by the same method to the example 1 except using 800 mg of N-cyano-N'-(4-chlorophenyl)thiourea sodium salt and 200 mg of the aminoalcohol compound prepared in the preparation example 5. The residue was purified by silica gel chromatography (n-hexane ethyl acetate=1:1) to afford 108 mg (yield: 32 32%) of the desire compound of (2R,3R,4S) stereochemistry.

¹H NMR (DMSO-d₆, 300 MHz) δ1.4(s, 3H), 3.15(s, 3H), 3.45(d, 1H), 3.64(d, 1H), 3.8(t, 1H), 5.08(t, 1H), 6.09(s, H), 6.94(d, 1H), 7.34(dd, 4H), 7.64(s, 1H), 8.01(d, 2H), 9.5(s, 1H)

Example 31

Preparation of (2R,3S,4R)-N"-cyano-N-(6-nitro-3,4-dihydro-3-hydroxy-2-methyl-2-methoxymethyl-2H-benzopyran-4-yl)-N'-(4-chlorophenyl)guanidine The reaction was performed by the same method to the example 30. The residue was purified by silica gel chromatography (n-hexane:ethyl acetate=1:1) to afford 107 mg (yield: 32%) of the desired compound of (2R,3S,4R) stereochemistry.

¹H NMR (DMSO-d₆, 300 MHz) δ1.15(s, 3H), 3.3(s, 3H), 3.45(d, 1H), 3.6(d, 1H), 4.06(t, 1H), 5.00(t, 1H), 5.9(s, 1H), 6.96(d, 1H), 1.34(dd, 4H), 7.8(s, 1H), 8.0(m, 2H), 7.48(s, 1H)

Example 32

Preparation of (2S,3R,4S)-N"-cyano-N-(6-nitro-3,4-dihydro-3-hydroxy-2-methyl-2-dimethoxymethyl-2H-benzopyran-4-yl)-N'-(2-chlorophenyl)guanidine The reaction was performed by the same method to the example 10 except using 508 mg of N-cyano-N-40 -(2-chlorophenyl)thiourea sodium salt and 500 mg of the aminoalcohol compound prepared in the preparation example 2. The residue was purified by silica gel chromatography (n-hexane:ethyl acetate=1:1) to afford 188 mg (yield: 24%) of the desired compound of (2S,3R,4S) stereochemistry.

¹H NMR (DMSO-d₆, 300 MHz) δ1.35(s, 3H), 3.43(d, 6H), 3.88(t, 1H), 4.60(s, 1H), 5.11(t, 1H), 5.97(s, 1H), 6.95(d, 1H), 7.17(d, 1H) 7.25(d, 1H), 7.34(d, 2H), 7.19(d, 1H), 8.03(m, 2H), 9.49(s, 1H)

Example 33

Preparation of (2S,3S,4R)-N"-cyano-N-(6-nitro-3,4-dihydro-3-hydroxy-2-methyl-2-dimethoxymethyl-2H-benzopyran-4-yl)-N'-(2-chlorophenyl)guanidine The reaction was performed by the same method to the example 32. The residue was purified by silica gel chromatography (n-hexane:ethyl acetate=1:1) to afford 270 mg (yield: 34%) of the desired compound of (2S,3S,4R) stereochemistry.

¹H NMR (DMSO-d₆, 300 MHz) δ1.24(s, 3H), 3.43(d, 6H), 4.10(t, 1H, 4.49(s, 1H), 5.00(s, 1H), 5.85(s, 1H), 6.98(d, 1H), 7.19(d, 1H), 7.28(d, 1H), 7.35(m, 2H), 7.10(d, 1H), 8.05(d, 1H), 9.53(s, 1H)

Example 34

Preparation of (2S,3R,4S)-N"-cyano-N-(6-nitro-3,4-dihydro-3-hydroxy-2-methyl-2-dimethoxymethyl-2H-benzopyran-4-yl)-N'-(2-trifluoromethylphenyl)guanidine The reaction was performed by the same method to the example 10 except using 582 mg of N-cyano-N'-(2-trifluoromethylphenyl)thiourea sodium salt and 500 mg of the aminoalcohol compound prepared in the preparation example 2. The residue was purified by silica gel chromatography (n-hexane:ethyl acetate=1:1) to afford 220 mg (yield: 26%) of the desired compound of (2S,3R,4S) stereochemistry.

¹H NMR (DMSO-d₆, 300 MHz) δ1.34(s, 3H), 3.43(d, 6H), 3.88(t, 1H), 4.60(s, 1H), 5.11(t, 1H), 5.97(s, 1H), 6.95(d, 1H), 7.45(d, 1H), 7.60(m, 3H), 7.87(d, 1H), 8.03(dd, 1H), 8.10(s, 1H), 9.62(s, 1H)

Example 35

Preparation of (2S,3S,4R)-N"-cyano-N-(6-nitro-3,4-dihydro-3-hydroxy-2-methyl-2-dimethoxymethyl-2H-benzopyran-4-yl)-N'-(2-trifluoromethylphenyl,)guanidine The reaction was performed by the same method to the example 34. The residue was purified by silica gel chromography (n-hexane:ethyl acetate=1:1) to afford 320 mg (yield: 37%) of the desired compound of (2S,3S, 4R) stereochemistry.

¹H NMR (DMSO-d₆, 300 MHz) δ1.24(s, 3H), 3.43(d, 6H), 4.08(t, 1H), 4.49(s, 1H), 5.00(s, 1H), 5.82(s, 1H), 6.98(d, 1H), 7.47(d, 1H), 7.61(dd, 3H), 8.03(m, 3H), 9.67(s, 1H)

Example 36

Preparation of (2S,3R,4S)-N"-cyano-N-(6-nitro-3,4-dihydro-3-hydroxy-2-methyl-2-dimethoxymethyl-2H-benzopyran-4-yl)-N'-(2-chlorobenzyl)guanidine The reaction was performed by the same method to the example 10 except using 540 mg of N-cyano-N'-(2-chlorobenzyl)thiourea sodium salt and 500 mg of the aminoalcohol compound prepared in the preparation example 2. The residue was purified by silica gel chromatography (n-hexane:ethyl acetate=1:1) to afford 73 mg (yield: 9%) of the desired compound of (2S,3R,4S) stereochemistry.

$^1$H NMR (DMSO-d$_6$, 300 MHz) δ1.36(s, 3H), 3.47(d, 6H), 3.68(s, 1H), 4.13 (m, 1H), 4.39(s, 1H), 4.52(s, 2H), 5.57(s, 1), 6.6(s, 1H), 6.88 (m, 1H), 7.25 (m, 6H), 8.01(d, 1H), 8.16(s, 1H)

Example 37

Preparation of (2S,3S,4R)-N"-cyano-N-(6-nitro-3,4-dihydro-3-hydroxy-2-methyl-2-dimethoxymethyl-2H-benzopyran-4-yl)-N'-(2-chlorobenzyl)guanidine The reaction was performed by the same method to the example 36. The residue was purified by silica gel chromatography (n-hexane:ethyl acetate=1:1) to afford 100 mg (yield: 12%) of the desired compound of (2S,3S, 4R) stereochemistry.

$^1$H NMR (DMSO-d$_6$, 300 MHz) δ1.28(s, 3H), 3.5(d, 6H), 3.6(s, 1H), 3.98(d, 1H), 4.53(m, 3H), 5.61(d, 1H), 5.89(t, 1H), 6.88(d, 1H), 7.25 (m, 3H), 7.40(d, 1H), 8.02(m, 2H), 8.14(s, H)

Example 38

Preparation of (2S,3S,4R)-N"-cyano-N-(6-nitro-3,4-dihydro-3-acetoxy-2-methyl-2-dimethoxymethyl-2H-benzopyran-4-yl)-N'-benzylguanidine To a solution of 68 mg (0.15 mmol) of the compound prepared in the example 25 dissolved in 3 ml of methylene chloride were added 21 ul of acetic anhydride, 42 ul of triethylamine and 2 mg of DMAP (4-(dimethylamino) pyridine). The reaction mixture was stirred for 5 hours at room temperature and extracted with ethyl acetate (10 ml×2) after adding 5 ml of water. The organic layer was washed with water and brine, dried over anhydrous magnesium sulfate, filtered and concentrated under reduced pressure. The residue was purified by silica gel chromatography (n-hexane:ethyl acetate=1:1) to afford 67 mg (yield: 90%) of the desired compound.

$^1$H NMR (DLSO-d$_6$, 300 MHz) δ1.3(s, 3H), 1.25(s, 1H), 2.1(s, 1H), 3.3(s, 3H), 3.5(s, 3H), 4.35(s, 1H), 4.52(s, 2H), 5.25(m, 1H) 5.32(s, 1H), 6.98(d, 2H), 7.38(s, 5H), 8.15(d, 2H)

Example 39

Preparation of (2S)-N"-cyano-N-(6-nitro-2-methyl-2-dimethoxymethyl-2H-benzopyran-4-yl)-N'-benzylguanidine To a solution of 54 mg (0.11 mmol) of the compound prepared in the example 38 dissolved in 2 ml of toluene was added 24 ul (0.1628 mol) of DBU. The reaction mixture was stirred for 24 hours at room temperature and extracted with ethyl acetate. The organic layer was dried over anhydrous magnesium sulfate, filtered and concentrated under reduced pressure. The residue was purified by silica gel chromatography (n-hexane:ethyl acetate=1:1) to afford 31 mg (yield: 64%) of the desired compound.

$^1$H NMR (DMSO-d$_6$, 300 MHz) δ1.43(s, 3H), 3.29(s, 3H), 3.39(s, 3H), 4.21(s, 1H), 4.59(d, 2H), 5.45(s, 1H), 7.02(d, 1H), 7.36(m, 5H), 8.29(dd, 2H), 8.82(d, 1H)

Example 40

Preparation of (2S,3S,4R)-N"-cyano-N-(6-amino-3,4-dihydro-3-hydroxy-2-methyl-2-dimethoxymethyl-2H-benzopyran-4-yl)-N'-benzylguanidine To a solution of 1.11 g of the compound prepared in the example 24 dissolved in 20 ml of methanol was added 10 ml of the saturated cupric acetate solution. To this mixture was added 276 mg of sodium borohydride slowly. The reaction mixture was stirred for 3 hours at room temperature and extracted with 100 ml of ethyl acetate after adding 50 ml of water. The organic layer was dried over anhydrous magnesium sulfate, filtered and concentrated under reduced pressure. The residue was purified by silica gel chromatography (n-hexane:ethyl acetate=1:3) to afford 576 mg (yield: 56%) of the desired compound.

$^1$H NMR (CDCl$_3$, 300 MHz) δ1.21(s, 3H), 3.58(s, 3H), 3.59(s, 3H), 4.14(d, 1H), 4.30(s, 1H), 4.45(d, 1H), 4.47(d, 1H), 5.46(d, 1H), 6.60–6.66((m, 3H), 7.32–7.36(m, 5H)

Example 41

Preparation of (2S,3S,4R)-N"-cyano-N-(6-acetoxyamino-3,4-dihydro-3-hydroxy-2-methyl-2-dimethoxymethyl-2H-benzopyran-4-yl)-N'-benzylguanidine To a solution of 50 mg of the compound prepared in the example, 40 dissolved in 2 ml of methylene chloride were added 25 ul of triethylamino and 10 ul of acetyl chloride.

The reaction mixture was stirred for 1 hour at room temperature and extracted with 10 ml of water and 20 ml of ethyl acetate. The organic layer was dried over anhydrous magnesium sulfate, filtered and concentrated under reduced pressure. The residue was purified by silica gel chromatography (n-hexane:ethyl acetate=1:2) to afford 51 mg (yield: 92%) of the desired compound.

$^1$H NMR (DMSO-d$_6$, 200 MHz) δ1.15(s, 3H), 1.96(s, 3H), 3.38(s, 3H), 3.51(s, 3H), 3.98(m, 2H), 4.30(s, 1H), 4.38–4.49(m, 2H), 5.22(br s, 1H), 5.48(br s, 1H), 6.64(d, 1H), 7.31(br s, 5H), 7.61(br s, 1H), 7.94(s, 1H), 9.76(s, 1H)

Example 42

Preparation of (2S,3S,4R)-N"-cyano-N-(6-methanesulfonylamino-3,4-dihydro-3-hydroxy-2-methyl-2-dimethoxymethyl-2H-benzopyran-4-yl)-N'-benzylguanidine To a solution of 91 mg of the compound prepared in the example 40 dissolved in 2 ml of methylone chloride were added 45 ul of triethylamine and 20 ul of methanesulfonyl chloride. The reaction mixture was stirred for 2 hours at room temperature and extracted with 10 ml of water and 20 ml of ethyl acetate. The organic layer was dried over anhydrus magnesium sulfate, filtered and concentrated under reduced pressure. The residue was purified by silica gel chromatography (n-hexane:ethyl acetate=1:2) to afford 90 mg (yield: 85%) of the desired compound.

$^1$H NMR (CDCl$_3$, 200 MHz) δ1.25(s, 3H), 2.90(s, 3H), 3.57(s, 6)H), 4.10(d, 1H), 4.25(d, 1H), 4.34(s, 1H), 4.43(d,

1H), 4.50(d, 1H), 4.61(t, 1H), 5.83(d, 1H), 6.78(d, 1H), 7.20–7.38(m, 7H), 8.18(br s, 1H)

Example 43

Preparation of (2S,3S,4R)-N"-cyano-N-(6-cyano-3, 4-dihydro-3-hydroxy-2-methyl-2-dimethoxymethyl-2H-benzopyran-4-yl)-N'-(4-chlorophenyl)guanidine To a solution of 100 mg of (2S,3S,4R)-6-cyano-2-methyl-2-dimethoxymethyl-3-hydroxy-4-amino-3,4-dihydro-2H-1-benzopyran prepared in the preparation example 6 is dissolved in 3 ml of DMF, were added 92 mg of N-cyano-N'-(4-chlorophenyl)thiourea sodium salt and 89 mg of 1-[3-(dimethylamino)propyl]-2-ethylcarbodiimide hydrochloride. The reaction mixture was stirred for 6 hours at room temperature, and extracted with 30 ml of ethyl acetate after acidifying the mixture by adding 5 ml of 1N HCl. The organic Layer was dried over anhydrous magnesium sulfate and concentrated under reduced pressure. The residue was purified by siLica gel chromatography (n-hexane:ethyl acetate=1:1 to afford 70 mg (yield: 43%) of the desired compound Of (2S,3R,4S) stereochemistry.

$^1$H NMR (CDCl$_3$, 200 MHz) δ1.36(s, 3H), 3.49(s, 3H), 3.53(s, 3H), 3.58(t, 1H), 4.34(s, 1H), 4.99(t, 1H), 5.62(s, 1H), 6.86(d, 1H), 7.25–7.55(m, 5H), 7.69(s, 1H)

Example 44

Preparation of (2S,3R,4S)-N"-cyano-N-(6-cyano-3, 4-dihydro-3-hydroxy-2-methyl-2-dimethoxymethyl-2H-benzopyran-4-yl)-N'-(4-chlorophenyl)guanidine The reaction was performed by the same method to the example 43 except using 99 mg (0.35 mmol) of (2S,3R,4S)-6-cyano-2-methyl-2-dimethoxymethyl-3-hydroxy-4-amino-3,4-dihydro-2H-1-benzopyran prepared in the preparation example 7 as a starting material. The residue was purified by silica gel chromatography (n-hexane:ethyl acetate=1:1) to afford 68 mg (yield: 42%) of the desired compound.

$^1$H NMR (CDCl$_3$, 200 MHz) δ1.50(s, 3H), 3.44(s, 3H), 3.48(s, 3H), 3.66(t, 1H), 4.43(s, 1H), 5.24(d, 2H), 6.84(d, 1H), 7.27–7.44(m, 4H), 7.55(s, 1H), 8.53(s, 1H)

Example 45

Preparation of (2S,3S,4R)-N"-cyano-N-(6-cyano-3, 4-dihydro-3-hydroxy-2-methyl-2-dimethoxymethyl-2H-benzopyran-4-yl)-N'-benzylguanidine (Step 1) Preparation of (2S,3S,4R)-4-[[(cyanoimino)phenoxymethyl]amino]-3,4-dihydro-3-hydroxy-2-methyl-2-dimethoxymethyl-2H-benzopyran-6-carbonitrile To a solution of 150 mg of (2S,3S,4R)-6-cyano-2-methyl-2-dimethoxymethyl-3-hydroxy-4-amino-3,4-dihydro-2H-1-benzopyran prepared in the preparation example 6 dissolved in 3 ml of isopropanol-DMF (2:1), were added 141 mg of diphenyl cyanocarbonimidate and 97 ul of triethylamine. The reaction mixture was stirred for 18 hours at room temperature, and extracted with 10 ml of water and 30 ml of ethyl acetate. The organic layer was dried aver anhydrous magnesium sulfate, filtered and concentrated under reduced pressure. The residue was purified by silica gel chromatography (n-hexane:ethyl acetate=1:2) to afford 182 mg (yield: 80%) of the desired compound.

(Step 2) Preparation of (2S,3S,4R)-N-cyano-N-(6-cyano-3, 4-dihydro-3-hydroxy-2-methyl-2-dimethoxymethyl-2H-benzopyran-4-yl)-N'-benzylguanidine To a solution of 182 mg of the compound prepared in the above step 1 dissolved in 2 ml of DMF was added 0.42 ml of benzylamine. The reaction mixture was stirred for 12 hours at room temperature and extracted with 20 ml of water and 50 ml of ethyl acetate. The organic layer was dried over anhydrous magnesium sulfate, fiLtered and concentrated under reduced pressure. The residue was purified by silica gel chromatography (n-hexane:ethyl acetate=1:2) to afford 163 mg (yield: 68%) of the desired compound.

$^1$H NMR (CDCl$_3$, 200 MHz) δ1.29(s, 3H), 3.45(s, 3H), 3.52(s, 3H), 4.09(t, 1H), 4.35(s, 2H), 4.43(d, 1H), 4.81(t, 1H), 5.94(s, 1H), 6.83(d, 1H), 7.28–7.40(m, 7H)

Example 46

Preparation of (2S,3R,4S)-N"-cyano-N-(6-cyano-3, 4-dihydro-3-hydroxy-2-methyl-2-dimethoxymethyl-2H-benzopyran-4-yl)-N'-benzylguanidine The reaction was performed by the same method to the step 1 and step 2 of example 45 except using 150 mg of (2S,3R,4S)-6-cyano-2-methyl-2-dimethoxymethyl-3-hydroxy-4-amino-3,4-dihydro-2H-1-benzopyran prepared in the preparation example 7 as a starting material. The residue was purified by silica gel chromatography (n-hexane:ethyl acetate=1:2) to afford 160 mg (yield: 69%) of the desired compound.

$^1$H NMR (CDCl$_3$, 200 MHz) δ1.35(s, 3H), 3.43(s, 3H), 3.44(s, 3H), 3.75(t, 1H) 3.82(s, 2H), 4.47(s, 1H) 5.05(t, 1H), 5.60(s, 1H), 6.81(d, 1H), 7.20–7.40(m, 7H)

Example 47

Preparation of (2S,3S,4R)-N"-cyano-N-(6-bromo-3, 4-dihydro-3-hydroxy-2-methyl-2-dimethoxymethyl 2H-benzopyran-4-yl)-N'-benzylguanidine The reaction was performed by the same method to the step 1 and step 2 of example 45 except using 98 mg of (2S,3S,4R)-6-bromo-2-methyl-2-dimethoxymethyl-3-hydroxy-4-amino-3,4-dihydro-2H-1-benzopyran prepared in the preparation example 8 as a starting material. The residue was purified by silica gel chromatography (n-hexane:ethyl acetate=1:2) to afford 86 mg (yield: 83%) of the desired compound.

$^1$H NMR (CDCl$_3$) δ1.21(s, 3H), 3.39(s, 3H), 3.42(s, 3H), 4.10(d, 1H), 4.29(s, 1H), 4.42(dd, 2H), 4.65(m, 2H), 5.61(d, 1H), 7.20–1.40(m, 4H)

Example 48

Preparation of (2S, 3S, 4R)-N"-cyano-N-(6-nitro-3, 4-dihydro-3-hydroxy-2-methyl-2-dimethoxymethyl-2-H-benzopyran-4-yl)-n'-(3,4-dimethoxybenzyl) guanidine (Step 1) Preparation of (2S,3S,4R)-4-[[(cyanoimino)phenoxymethyl]amino]-6-nitro-3,4-dihydro-3-hydroxy-2-methyl-2-dimethoxymethyl-2H-benzopyran The compound prepared in the preparation example 2 was separated by silica gel chromotography (n-hexane:ethyl 4R)-6-nitro-2-methyl-2-dimethoxymethyl-2H-benzopyran.

To a solution of 400 mg (1.34 mmol) of (2S,3S, 4R)-6-nitro-2-methyl-2-dimethoxymethyl-2H-benzopyran dissolved in 3 ml of DMF, were added 352 mg (1.48 mmol) of diphenyl cyanocarbonimidate and 243 ul (1.74 mmol) of triethylamine. The reaction mixture was stirred for 12 hours at room temperature and extracted with 20 ml of water and 30 ml of ethyl acetate. The organic layer was dried over anhydrous magnesium sulfate, filtered and concentrated under reduced pressure. The residue was purified by silica gel chromatography (n-hexane:ethyl acetate=1:2) to afford 498 mg (yield: 84%) of the desired compound.

(Step 2) Preparation of (2S,3S,4R)-N"-cyano-N-(6-nitro-3,4-dihydro-3-hydroxy-2-methyl-2-dimethoxymethyl-2H-benzopyran-4-yl)-N'-(3,4-dimethoxybenzyl)guanidine To a solution of 327 mg (0.74 mmol) of the compound prepared in the above step 1 dissolved in 3 ml of DMF was added 371 mg (2.22 mmol, 3 eq) of (3,4-dimethoxybenzyl) amine. The reaction mixture was stirred for 12 hours at room temperature and extracted with 20 ml of water and 30 ml of ethyl acetate. The organic layer was dried over anhydrous magnesium sulfate, filtered and concentrated under reduced pressure. The residue was purified by silica gel chromatography (n-hexane:ethyl acetate=1:2) to afford 338 mg (yield: 89%) of the desired compound.

$^1$H NMR (CDCl$_3$, 200 MHz) δ1.33(s, 3H), 3.53(s, 3H), 3.57(s, 3H), 3.86(s, 3H), 3.87(s, 3H), 4.14(d, H), 4.38(s, 1H), 4.24–4.50(m, 2H), 4.82(br t, 1H), 6.15(s, 1H), 6.61(t, 1H), 6.84 (m, 3H), 6.92(d, 1H), 8.08(dd, 1H), 8.35(s, 1H)

Example 49

Preparation of (2S,3S,4R)-N'-cyano-N-(6-amino-3,4-dihydro-3-hydroxy-2-methyl-2-dimethoxymethyl-2H-benzopyran-4-yl)-N'-(3,4-dimethoxybenzyl)guanidine To a solution of 209 mg (0.41 mmol) of the compound prepared in the example 48 dissolved in 5 ml of methanol was added 0.5 ml (0.2 mmol, 0.5 eq) of 0.4M aqueous Cu(OAc)$_2$ solution. To this mixture was added 155 mg (4.1 mmol, 10 eq) of sodium borohydride slowly for 30 min. The reaction mixture was stirred for 1 hour aL room temperature, extracted with 10 ml of ethyl acetate and filtered to remove a precipitated black solid. The filtered solution was extracted with 30 ml of ethyl acetate after adding 10 ml of the saturated aqueous NaHCO$_3$ solution. The organic layer was washed with brine, dried over anhydrous magnesium sulfate, filtered and concentrated under reduced pressure. The residue was purified by silica gel chromatography (n-hexane:ethyl acetate=9:1) to afford 169 mg (yield: 85%) of the desired compound.

$^1$H NMR (CDCl$_3$, 200 MHz) δ1.20(s, 3H), 3.57(s, 6H), 3.87(s, 6H), 4.29(s, 1H), 4.04–4.12(m, 2H), 4.32–4.58(m, 2H), 5.46(d, 1H), 6.50–6.69(m, 3H), 6.84(m, 3H), 7.26(br s, 1H)

Example 50

Preparation of (2S,3S,4R)-N"-cyano-N-(6-nitro-3,4-dihydro-3-hydroxy-2-methyl-2-dimethoxymethyl-2H-benzopyran-4-yl)-N'-(4-methoxybenzyl)guanidine The reaction was performed by the same method to the step 2 of example 48 except using 360 mg of the compound prepared in the step 1 of example 48 as a starting material and 333 mg (2.43 mmol) of 4-methoxybenzylamine in place of (3,4-dimethoxybenzyl)amine. The residue was purified by silica gel chromatography (n-hexane:ethyl acetate=1:2) to to afford 343 mg (yield: 87%) of the desired compound.

$^1$H NMR (CDCl$_3$, 200 MHz) δ1.20(s, 3H), 3.51(d, 6H), 3.77(s, 3H), 3.80(d, 2H), 4.44(t, 1H), 4.56(s, 1H), 5.32(m, 1H), 6.06(s, 1H), 6.40(d, 1H), 6.90(m, 3H), 7.12(m, 2H), 7.30(d, 1H), 8.00(dd, 1H), 8.03(s, 1H)

Example 51

Preparation of (2S,3S,4R)-N"-cyano-N-(6-amino-3,4-dihydro-3-hydroxy-2-methyl-2-dimethoxymethyl-2H-benzopyran-4-yl)-N'-(4-methoxybenzyl)guanidine The reaction was performed by the same method to the example 49 except using 304 mg (0.62 mmol) of the compound prepared in the example 50 as a starting material. The residue was purified by silica gel chromatography (n-hexane:ethyl acetate=1:4) to afford 241 mg (yield: 85%) of the desired compound.

$^1$H NMR (CDC$_3$, 200 MHz) δ1.21(s, 3H), 3.58(s, 6H), 3.81(s, 3H), 4.15(d, 1H), 4.17(d, 1H), 4.30(s, 1H), 4.36–4.54 (m, 3H), 5.48(d, 1H), 6.52–6.71(m, 3H), 6.88(d, 2H), 7.09 (br s, 1H), 7.24(d, 2H)

Example 52

Preparation of (2S,3S,4R)-N"-cyano-N-(6-nitro-3,4-dihydro-3-hydroxy-2-methyl-2-dimethoxymethyl-2H-benzopyran-4-yl)-N'-(3-nitrobenzyl)guanidine The reaction was performed by the same method to the step 2 of example 48 except using 358 mg (0.81 mmol) of the compound prepared in the step 1 of example 48 as a starting material and 458 mg (2.43 mmol) of 3-nitro) bernzylamine HCl salt in place of (3,4-dimethoxybenzyl) amine. The residue was purified by silica gel chrotography (n-hexane:ethyl acetate=1:2 to afford 302 mg (yield: 74%) of the desired compound.

$^1$H NMR (CDCl$_3$, 200 MHz) δ1.18(s, 3H), 3.43(d, 6H), 4.09(t, 1H), 4.49(s, 1H), 5.00(t, 1H), 5.85(s, 1H), 6.98(d, 1H), 7.29(d, 1H), 7.37(d, 1H), 7.40(m, 2H), 7.91(d, 1H), 8.05(m, 2H)

Example 53

Preparation of (2S,3S,4R)-N"-cyano-N-(6-nitro-3,4-dihydro-3-hydroxy-2-methyl-2-dimethoxymethyl-2H-benzopyran-4-yl)-N'-(3-trifluoromethylbenzyl)guanidine The reaction was performed by the same method to the step 2 of example 48 except using 443 mg (1.0 mmol) of the compound prepared in the step 1 of example 48 as a starting material and 525 mg (3.0 mmol) of (3-trifluoromethyl) benzylamine in place of (3,4-dimethoxyenzyl)amine. The residue was purified by silica gel chromatography (n-hexane:ethyl acetate=1:2) to afford 497 mg (yield: 95%) of the desired compound.

$^1$H NMR (CDCl$_3$, 200 MHz) δ1.33(s, 3H), 3.55(s, 3H), 3.59(s, 3H), 4.19(d, 1H), 4.38(s, 1H), 4.40 (m, 1H), 4.54(d, 1H), 4.78 (m, 1H), 6.48 (br s, 1H), 6.84 (br s, 1H), 6.94(d, 1H), 7.53(m, 5H), 8.09(dd, 1H), 8.56(s, 1H)

Example 54

Preparation of (2S,3S,4R)-N"-cyano-N-( 6-amino-3,4-dihydro-3-hydroxy-2-methyl-2-dimethoxymethyl-2H-benzopyran-4-yl)-N'-(3-trifluoromethylbenzyl)quanidine The reaction was performed by the same method to the example 49 except using 278 mg (0.53 mmol) of the compound prepared in the example 53 as a starting material. The residue was purified by silica gel chromatography (n-hexane:ethyl acetate=1:4) to afford 192 mg (yield: 73%) of the desired compound.

$^1$H NMR (CDCl$_3$, 200 MHz) δ1.23(s, 3H), 3.59(s, 6H), 4.16(d, 1H), 4.31(s, 1H), 4.40–4.67(m, 3H), 5.53(d, 1H), 6.57–6.14(m, 3H), 7.31(br t, 1H), 7.46–7.59(m, 5H)

Example 55

Preparation of (2S,3S,4R)-N"-cyano-N-(6-methanesulfonyloxy-3,4-dihydro-3-hydroxy-2-methyl-2-dimethoxymethyl-2H-benzopyran-4-yl)-N'-benzylguanidine (Step 1) Preparation of (2S,3S,4R)-4-[[(cyanoimino) phenoxymethyl]amino]-6-methanesulfonyloxy-3,4-dihydro-3-hydroxy-2-methyl-2-dimethoxymethyl-2H-1-benzopyran The reaction was performed by the same method to the step 1 of example 48 except using 58 mg (0.18 mmol) of the compound prepared in the preparation example 9 as a starting material. The residue was purified silica gel chromatography (n-hexane:ethyl acetate=1:2) to afford 64 mg (yield: 74%) of the desired compound.

(Step 2) Preparation of (2S,3S,4R)-N"-cyano-N-(6-methanesulfonyloxy-3,4-dihydro-3-hydroxy-2-methyl-2-dimethoxymethyl-2H-benzopyran-4-yl)-N'-benzylguanidine The reaction was performed by the same method to the step 2 of example 48 except using 64 mg (0.13 mmol) of the compound prepared in the above step 1 and 28 ul (0.26 mmol). The residue was purified by silica gel chromatography (n-hexane:ethyl acetate=1:1) to afford 32 mg (yield: 49%) of the desired compound.

$^1$H NMR (CDCl$_3$, 200 MHz) δ1.28(s, 1H), 3.21(s, 3H), 3.58(s, 3H), 3.59 (s, 3H), 4.15(m, 1H), 4.35(s, 1H), 4.52(m, 1H), 4.63(m, 1H), 5.45(d, 1H), 6.87(d, 1H), 6.92(br s, 1H), 7.20–7.42(m, 6H)

Example 56

Preparation of (2R,3S,4R)-N"-cyano-N-(6-methanesulfonyloxy-3,4-dihydro-3-hydroxy-2-methyl-2-dimethoxymethyl-2H-benzopyran-4-yl)-N'-benzy]guanidine (Step 1) Preparation of (2R,3S,4R)-4-[[(cyanoimino)phenoxymethyl]amino]-6-methanesulfonyloxy-3,4-dihydro-3-hydroxy-2-methyl-2-dimethoxymethyl-2H-1-benzyopyran The reaction was performed by the same method to the step 1 of example 55 except using 63 mg (0.19 mmol) of the compound prepared in the preparation example 10 as a starting material. The residue was purified by silica gel chromatography (n-hexane:ethyl acetate=1:2) to afford 75 mg (yield: 79%) of the desired compound.

(Step 2) Preparation of (2R,3S,4R)-N"-cyano-N-(6-methanesulfonyloxy-3,4-dihydro-3-hydroxy-2-methyl-2-dimethoxymethyl-2H-benzopyran-4-yl)-N'-benzylguanidine The reaction was performed by the same method to the step 2 of example 55 except using 75 mg (0.15 mmol) of the compound prepared in the above step 1 and 28 ul (0.26 mmol). The residue was purified by silica gel chromatography (n-hexane:ethyl acetate=1:2) to afford 57 mg (yield: 74%) of the desired compound.

$^1$H NMR (CDCl$_3$, 200 MHz) δ1.26(s, 3H), 3.16(s, 3H), 3.41(s, 3H), 3.47(s, 3H), 3.72(d, 1H), 4.43(s, 1H), 4.46(d, 1H), 5.02(t, 1H), 5.25(d, 1H), 6.59(t, 1H), 6.84(d, 1H), 7.02–7.20(m, 2H), 7.22–7.40(m, 4H)

Example 57

Preparation of (2S,3R,4S)-N"-cyano-N-(6-amino-3,4-dihydro-3-hydroxy-2-methyl-2-dimethoxymethyl-2H-benzopyran-4-yl)-N'-benzylguanidine The reaction was performed by the same method to the example 49 except using 884 mg (1.94 mmol) of the compound prepared in the example 24 as a starting material. The residue was purified by silica gel chromatography (n-hexane:ethyl acetate=1:3) to afford 313 mg (yield: 38%) of the desired compound.

$^1$H NMR (CDCl$_3$, 500 MHz) δ1.41(s, 3H), 1.75(br s, 1H), 3.39(s, 3H), 3.45(s, 3H), 3.46(d, 1H), 3.72(d, 1H), 4.40(s, 1H), 4.46(d, 2H), 4.78(d, 1H), 5.22(m, 1H), 6.41(m, 1H), 6.50(m, 1H), 6.59(d, 1H), 6.73(m, 1H), 7.30–7.37 (m, 4H)

Example 58

Preparation of (2R,3R, 4S)-N"-cyano-N-(6-amino-3,4-dihydro-3-hydroxy-2-methyl-2-dimethoxymethyl-2H-benzopyran-4-yl)-N'-benzylguanidine The reaction was performed by the same method to the example 49 except using 1.2 g (2.7 mmol) of the compound prepared in the example 22 as a starting material. The residue was purified by silica gel chromatography (n-hexane:ethyl ethyl acetate=1:3) to afford 547 mg (yield: 48%) of the desired compound.

$^1$H NMR (CDCl$_3$, 500 MHz) δ1.21(s, 3H), 1.80(br s, 2H), 3.57(s, 3H), 3.58(s, 3H), 4.10–4.13(m, 1H), 4.20–4.38(m, 1H), 4.31(s, 1H), 4.98(dd, 1H), 4.50(dd, 1H), 5.60(s, 1H), 6.58–6.79(m, 2H), 7.28–7.37(m, 6H)

Example 59

Preparation of (2R,3S,4R)-N"-cyano-N-(6-amino-3,4-dihydro-3-hydroxy-2-methyl-2-dimethoxymethyl-2H-benzopyran-4-yl)-N'-benzylguanidine The reaction was performed by the same method to the example 49 except using 1.07 g (2.3 mmol) of the compound prepared in the example 23 as a starting material. The residue was purified by silica gel chromatography (n-hexane:ethyl acetate=1:2) to afford 589 mg (yield: 60°) of the desired compound.

$^1$H NMR (CDCl$_3$, 500 MHz) δ1.41(s, 3H), 1.75(br s, 1H), 3.39(s, 3H), 3.45(s,3H), 3.46(d, 1H), 3.72(d, 1H), 4.40(s, 1H), 4.46(d, 2H), 4.78(d, 1H), 5.22(m, 1H), 6.41(m, 1H), 6.50(m, 1H), 6.59(d, 1H), 6.73(m, 1H), 7.30–7.37(m, 4H)

Example 60

Preparation of (2S,3S,4R)-N"-cyano-N-(6-nitro-3,4-dihydro-3-hydroxy-2-methyl-2-([1,3]dioxolan-2-yl)-2H-benzopyran-4-yl)-N'-benzylguanidine (Step 1) Preparation of (2S,3S,4R)-4-[[(cyanoimino)phenoxymethyl]amino]-6-nitro-3,4-dihydro-3-hydroxy-2-methyl-2-([1,3]dioxolan-2-yl)-2H-1-benzopyran The reaction was performed by the same method to the step 1 of example 48 except using 400 mg (1.35 mmol) of the compound prepared n the preparation example 11 as a starting material. The residue was purified by silica gel chromatography (n-hexane:ethyl acetate=1:3) to afford 400 mg (yield: 67%) of the desired compound.

1H NMR (CDCl$_3$, 200 MHz) δ1.40(s, 3H), 3.2(d, 1H), 3.81–3.9(m, 4H), 4.69(sr 1H), 5.15(t, 1H), 6.98(d, 1H), 7.15–7.42(m, 5H), 8.12(dd, 1H), 8.30(d,1H)

(Step 2) Preparation of (2S,3S,4R,)-N"-cyano-N-(6-nitro-3,4-dihydro-3-hydroxy-2-methyl-2-([1,3]dioxolan-2-yl)-2H-benzopyran-4-yl)-N'-benzylguanidine The reaction was performed by the same method to the step 2 of example 48 except using 400 mg (0.1 mmol) of the compound prepared in the above step 1 as a starting material and 0.3 ml (2.7 mmol) of benzylamine in place of (3,4-dimethoxybenzyl)amine. The residue was purified by silica gel chromatography (n-hexane:ethyl acetate=1:2) to afford 350 mg (yield: 85%) of the desired compound.

$^1$H NMR (CDCl$_3$, 200 MHz) δ1.35(s, 3H), 3.95–4.15(m, 4H), 4.49(dd, 2H), 4.91(t, 1H), 5.05(s, 1H), 5.62(s, 1H), 6.61(t, 1H), 6.95(d, 1H), 7.29–7.41(m, 5H), 8.12(dd, 1H), 8.21(d, 1H)

Example 61

Preparation of (2S,3S,4R)-N"-cyano-N-(6-amino-3, 4-dihydro-3-hydroxy-2-methyl-2-([1,3]dioxolan-2-yl)-2H-benzopyran-4-yl)-N'-benzylguanidine The reaction was performed by the same method to the example 49 except using 200 mg (0.44 mmol) of the compound prepared in the example 60 as a starting material. The residue was purified by silica gel chromatography (n-hexane:ethyl acetate=1:3) to afford 90 mg (yield: 48%) of the desired compound.

$^1$H NMR (CDCl$_3$, 200 MHz) δ1.24(s, 3H), 3.92–4.14(m, 4H), 4.45(dd, 2H), 4.97(s, 1H), 5.51(d, 1H), 6.45–6.80(m, 3H), 7.12(s, 1H), 7.25–7.42(m, 3H)

Example 62

Preparation of (2S,3S,4R)-N"-cyano-N-(6-nitro-3,4-dihydro-3-hydroxy-2-methyl-2-([1,3]dioxan-2-yl)-2H-benzopyran-4-yl)-N'-benzylguanidine (Step 1) Preparation of (2S,3S,4R)-4-[[(cyanoimino) phenoxymethyl]amino]-6-nitro-3,4-dihydro-3-hydroxy-2-methyl-2-([1,3]dioxan-2-yl)-2H-1-benzopyran The reaction was performed by the same method to the step 1 of example 60 except using 700 mg (2.26 mmol) of the compound prepared in the preparation example 12 as a starting material. The residue was purified by silica gel chromatography (n-hexane:ethyl acetate=1:1) to afford 840 mg (yield: 83%) of the desired compound.

(Step 2) Preparation of (2S,3S,4R)-N"-cyano-N-(6-nitro-3,4-dihydro-3-hydroxy-2-methyl-2-([1,31 ]dioxan-2-yl)-2H-benzopyran-4-yl)-N'-benzylguanidine The reaction was performed by the same method to the step 2 of example 48 except using 840 mg (1.85 mmol) of the compound prepared in the above step 1 as a starting material and 0.61 ml (5.56 mmol) of benzylamine in place of (3,4-dimethoxybenzyl)amine. The residue was purified by silica gel chromatography (n-hexane:ethyl acetate=1:2) to afford 750 mg (yield: 87%) of the desired compound.

$^1$H NMR (CDCl$_3$, 200 MHz) δ1.31(s, 3H), 1.4–1.52(m, 1H), 2.13–2.26(m, 1H), 3.80–3.98(m, 2H), 4.18–4.31(m, 3H), 4.45(d, 2H), 4.75(s, 1H), 4.81(t, 1H), 5.81(s, 1H), 6.75(t, 1H), 6.96(d, 1H), 7.28–7.40(m, 5H), 8.1(dd, 1H), 8.35(d, 1H)

Example 63

Preparation of (2S,3S,4R)-N"-cyano-N-(6-amino-3, 4-dihydro-3-hydroxy-2-methyl-2-([1,3]dioxan-2-yl)-2H-benzopyran-4-yl)-N'-benzylguanidine The reaction was performed by the same method of the example 49 except using 350 mg (0.75 mmol) of the compound prepared in the example 62 as a starting material. The residue was purified by silica gel chromatography (n-hexane:ethyl acetate=1:2) to afford 278 mg (yield: 85%) of the desired compound.

$^1$H NMR (CDCl$_3$, 200 MHz) δ1.23(s, 3H), 1.40–1.50(m, 1H), 2.12–2.22(m, 1H), 3.8–3.96(m, 2H), 4.15–4.32(m, 3H), 4.48(dd, 2H), 4.70(s, 1H), 5.41(d, 1H), 6.52–6.71(m, 3H), 7.15(s, 1H), 7.30–7.39(m, 5H)

Example 64

Preparation of (2S,3S,4R)-N"-cyano-N-(6-nitro-3,4-dihydro-3-hydroxy-2-methyl-2-([,3]-5,5-dimethyldioxan-2-yl)-2H-benzopyran-4-yl)-N'-benzylguanidine (Step 1) Preparation of (2S,3S,4R)-4-[[(cyanoimino) phenoxymethyl]amino]-6-nitro-3,4-dihydro-3-hydroxy-2-methyl-2-([1,3]-5,5-dimethyldioxan-2-yl)-2H-1-benzopyran The reaction was performed by the same method to the step 1 of example 60 except using 1.1 g (3.60 mmol) of the compound prepared in the preparation example 13 as a starting material. The residue was purified by silica gel chromatography (n-hexane:ethyl acetate 1:2) to afford 1 g (yield: 86%) of the desired compound. (step 2) Preparation of (2S,3S,4R)-N"-cyano-N-(6-nitro-3,4-dihydro-3-hydroxy-2-methyl-2-([1,31-5,5-dimethyldioxan-2-yl)-2H-benzopyran-4-yl)-N'-benzylguanidine The reaction was performed by the same method to the step 2 of example 48 except using 1 g (2.1 mmol) of the compound prepared in the above step 1 as a starting material. The residue was purified by silica gel chromatography (n-hexane:ethyl acetate=1:2) to afford 900 mg (yield: 87%) of the desired compound.

$^1$H NMR (CDCl$_3$, 200 MHz) δ0.78(s, 3H), 1.21(s, 3H), 1.34(s, 3H), 3.54(dd, 2H), 3.76(d, 2H), 4.20(d, 2H), 4.44(dd, 2H), 4.65(s, 1H), 4.81(t, 1H), 5.82(s, 1H), 6.72(t, 1H), 6.96(d, 1H), 7.29–7.41(m, 5H), 8.11(dd, 1H), 8.38(d, 1H)

Example 65

Preparation of (2S,3S,4R)-N"-cyano-N-(6-amino-3, 4-dihydro-3-hydroxy-2-methyl-2-([1,3]-5,5-dimethyldioxan-2-yl)-2H-benzopyran-4-yl)-N'-benzylguanidine The reaction was performed by the same method to the example 49 except using 400 mg (0.81 mmol) of the compound prepared in the example 64 as a starting material. The residue was purified by silica gel chromatography (n-hexane:ethyl acetate=1:3) to afford 350 mg (yield: 93%) of the desired compound.

$^1$H NMR (CDCl$_3$, 200 MHz) δ0.79(s, 3H), 1.21(s, 3H), 1.27(s, 3H), 3.51(dd, 2H), 3.74(d, 2H), 4.2(d, 1H), 4.35(d, 1H), 4.51(dd, 2H), 4.61(s, 1H), 4.73(s, 1H), 5.44 (dd, 1H), 6.52–6.75(m, 3H), 7.16(s, 1H), 7.28–7.41 (m, 5H)

Example 66

Preparation of (2S,3S,4R)-N"-cyano-N-(6-nitro-3,4-dihydro-3-hydroxy-2-methyl-2-dimethoxymethyl-2H-benzopyran-4-yl)-N'-benzylguanidine (Step 1) Preparation of (2S,3S,4R)-4-(cyanoimino) phenoxymethyl]amino]-6-nitro-3,4-dihydro-3-hydroxy-2-methyl-2-dimethoxymethyl-2H-1-benzopyran The reaction was performed by the same method to the step 1 of example 48 except using 234 mg (0.72 mmol) of the compound prepared in the preparation example 14 as a starting material. The residue was purified by silica gel chromatography (n-hexane:ethyl acetate=1:2) to afford 237 mg (yield: 70%) of the desired compound.

(Step 2) Preparation of (2S,3S,4R)-N"-cyano-N-(6-nitro-3,4-dihydro-3-hydroxy-2-methyl-2-dimethoxymethyl-2H-benzopyran-4-yl)-N'-benzylguanidine The reaction was performed by the same method to the step 2 of example 48 except using 217 mg (0.46 mmol) of the compound prepared in the above step 1 as a starting material. The residue was purified by silica gel chromatography (n-hexane:ethyl acetate=1:2) to afford 200 mg (yield: 90% of the desired compound.

$^1$H NMR (CDCl$_3$, 200 MHz) δ1.29(m, 9H), 3.74 (m, 5H), 4.20(d, 1H), 4.50 (m, 3H), 4.83(br s, 1H), 5.92(m, 1H), 6.52(m, 1H), 6.90(d, 1H), 7.34(m, 5H), 8.11(dd, 1H), 8.30(s, 1H)

Example 67

Preparation of (2S,3S,4R)-N'-cyano-N-(6-amino-3, 4-dihydro-3-hydroxy-2-methyl-2-dimethoxymethyl-2H-benzopyran-4-yl)-N'-benzylguanidine The reaction was performed by the same method to the example 49 except using 122 mg (0.25 mmol) of the compound prepared in the example 66 as a starting material. The residue was purified by silica gel chromatography (n-hexane:ethyl acetate=1:3) to afford 91 mg (yield: 80%) of the desired compound. $^1$H NMR (CDCl$_3$, 200 MHz) δ1.25 (m, 9H), 3.78(m, 4H), 4.18(d, 1H), 4.30(m, 4H), 5.53(d, 1H), 6.68(m, 3H), 7.18(br, 1H), 7.36(m, 5H)

Example 68

Preparation of (2S,3S,4R)-N"-cyano-N-(6-methoxycarbonyl-3,4-dihydro-3-hydroxy-2-methyl-2-dimethoxymethyl-2H-benzopyran-4-yl)-N'-benzylguanidine (Step 1) Preparation of (2S,3S,4R)-4-[[(cyanoamin)phenoxymethyl]amino]-6-methoxycarbonyl-3,4-dihydro-3-hydroxy-2-methyl-2-dimethoxymethyl-2H-1 -benzopyran The reaction was performed by the same method to the step 1 of example 48 except using 399 mg (1.28 mmol) of the compound prepared in the preparation example 15 as a starting material. The residue was purified by silica gel chromatography (n-hexane:ethyl acetate=1:2) to afford 397 mg (yield: 68%) of the desired compound.

(Step 2) Preparation of (2S,3S,4R)-N"-cyano-N-(6-methoxycarbonyl-3,4--dihydro-3-hydroxy-2-methyl-2-dimethoxymethyl-2H-benzopyran-4-yl)-N'-benzylguanidine The reaction was performed by the same method to the step 2 of example 48 except using 397 mg (0.93 mmol) of the compound prepared in the above step 1 and 0.21 ml (1.98 mmol) of benzylamine as a starting material. The residue was purified by silica gel chromatography (n-hexane:ethyl acetate=1:2) to afford 270 mg (yield: 67%) of the desired compound.

$^1$H NMR (CDCl$_3$, 200 MHz) δ1.21(s, 3H), 3.55(d, 6H), 3.86(s, 3H), 4.13(d, 1H), 4.17(s, 1H), 4.48(m, 2H), 5.77(d, 1H), 6.83(m, 1H), 6.85(d, H), 7.33(m, 4H), 7.93(dd, 1H), 7.99(s, 1H)

Example 69

Preparation of (2R,3S,4R)-N"-cyano-N-( 6-methoxycarbonyl-3,4-dihydro-3-hydroxy-2-methyl-2-dimethoxymethyl-2H-benzopyran-4-yl)-N'-benzylguanidine (Step 1) Preparation of (2R,3S,4R)-4-[[(cyanoimino)phenoxymethyl]amino]-6-methoxycarbonyl-3,4-didhydro-3-hydroxy-2-methyl-2-dimethoxymethyl-2H-1-benzopyran The reaction was performed by the same method to the step 1 of example 48 except using 121 mg (0.39 mmol) of the compound prepared in the preparation example 16 as a starting material. The residue was purified by silica gel chromatography (n-hexane:ethyl acetate=1:2) to afford 131 mg (yield: 74%) of the desired compound.

(Step 2) Preparation of (2R, 3S,4R)-N"-cyano-N-(6-methoxycarbonyl-3,4-dihydro-3-hydroxy-2-methyl-2-dimethoxymethyl-2H-benzopyran-4-yl)-N'-benzylguanidine The reaction was performed by the same method to the step 2 of example 48 except using 131 mg (0.31 mmol) of the compound prepared in the above step 1 and 60 ul (0.61 mmol) of benzylamine as a starting material. The residue was purified by silica gel chromatography (n-hexane:ethyl acetate=1:2) to afford 107 mg (yield 79%) of the desired compound.

$^1$N HMR (CDCl$_3$, 200 MHz) δ1.26(s, 3H), 3.43(d, 6H), 3.82(d, 1H), 3.77(s, 3H), 4.45(s, 1H), 4.48 (m, 2H), 5.64(d, 1H), 6.81(m, 1H), 6.83(d, 1H), 7.29(m, 4H), 7.80(dd, 1H), 7.84(s, 1H)

Example 70

Preparation of (3S,4R)-N"-cyano-N-(8-nitro-3,4-dihydro-3-hydroxy-2-methyl-2-dimethoxymethyl-2H-benzopyran-4-yl)-N'-benzylguanidine (Step 1) Preparation of (3S,4R)-4-[[(cyanoimino)phenoxymethyl]amino]-8-nitro-3,4-dihydro-3-hydroxy-2-methyl-2-dimethoxymethyl-2H-1-benzopyran The reaction was performed by the same method to the step 1 of example 48 except using 0.97 g (3.24 mmol) of the compound prepared in the preparation example 17 as a starting material. The residue was purified by silica gel chromatography (n-hexane:ethyl acetate=1:2) to afford 1.16 g (yield: 81%) of the desired compound.

(Stop 2) Preparation of (3S,4R)-N"-cyano-N-(8-nitro-3,4-dihydro-3-hydroxy-2-methyl-2-dimethoxymethyl-2H-benzopyran-4-yl)-N'-benzylguanidine The reaction was performed by the same method to the step 2 of example 48 except using 1.16 g (2.6 mmol) of the compound prepared in the above step 1 and 0.85 ml (7.8 mmol) of benzylamine as a starting material. The residue was purified by silica gel chromatography (n-hexane:ethyl acetate=1:2) to afford 0.94g (yield: 79%) of the desired compound as a racemic mixture of (2S,3S,4R- and (2R,3S,4R)-stereochemistry.

$^1$H NMR (CDCl$_3$, 200 MHz) δ1.23(s, 3H), 1.32(s, 3H), 3.37–3.40(s, 3H), 3.48(s, 3H), 3.84–3.87(d, 1H), 4.17–4.21 (d, 1H), 4.36–4.38(d, 1H), 4.41–4.45(d, 1H), 4.8(t, 1H), 5.04(t, 1H), 5.82(d, 1H), 6.09(d, 1H), 6.82–6.96(m, 2H), 1.27(s, 5H), 7.57–7.69(q, 1H)

Example 71

Preparation of (2S,3S,4R)-N"-cyano-N-(8-amino-3,4-dihydro-3-hydroxy-2-methyl-2-dimethoxymethyl-2H-benzopyran-4-yl)-N'-benzylguanidine The reaction was performed by the same method to the example 49 except using 298 mg (0.66 mmol) of the racemic mixture prepared in the example 70 as a starting material. The residue was purified by silica gel chromatography (n-hexane:ethyl acetate=1:4) to afford 117 mg (yield: 42%) f the desired compound of (2S,3S,4R) stereochemistry.

$^1$H NMR (CDCl$_3$, 200 MHz) δ1.25(s, 3H), 3.58(s, 3H), 3.8(s, 1), 4.39–4.47 (m, 4H),5.62(d, 1H), 6.58–6.61(d, 1H), 6.74–6.78(d, 1H), 7.12(s, H), 7.27–7.34(m, 5H)

Example 72

Preparation of (2R,3S,4R)-N"-cyano-N-(8-amino-3,4-dihydro-3-hydroxy-2-methyl-2-dimethoxymethyl-2H-benzopyran-4-yl)-N'-benzylguanidine The reaction was performed by the same method to the example 49 except using 298 mg (0.66 mmol) of the racemic mixture prepared in the example 70 as a starting material. The residue was purified by silica gel chromatography (n-hexane:ethyl acetate=1:4) to afford 106 mg (yield: 38%) of the desired compound of (2R,3S,4R) stereochemistry.

$^1$H NMR (CDC$_6$, 200 MHz) δ1.46(s, 3H), 3.41(s, 3H), 3.46(s, 3H), 3.73–3.81(m, 2H), 4.44(s, 1H), 4.46(s, 1H), 4.87(m, 1H), 5.2(m, 1H), 6.59–6.60(d, 1H), 6.63–6.76(t, 2H), 7.26–7.36(m, 5H)

The compounds prepared in the-above examples were listed in Table 1.

TABLE 1

| No | R₁ Sᵃ | R₁ Pᶜ | R₁ | R₃ | R₄ | R₅ S | R₅ P | R₆ S | R₆ P | n | Stereo chemistry |
|---|---|---|---|---|---|---|---|---|---|---|---|
| 1 | NO₂ | 6 | CH₃ | CH(OMe)₂ | OH | Cl | 4 | H | — | 0 | 2R, 3R, 4S |
| 2 | NO₂ | 6 | CH₃ | CH(OMe)₂ | OH | Cl | 4 | H | — | 0 | 2R, 3S, 4R |
| 3 | NO₂ | 6 | CH₃ | | OH | Cl | 3 | H | — | 0 | 2R, 3R, 4S |
| 4 | NO₂ | 6 | CH₃ | | OH | Cl | 3 | H | — | 0 | 2R, 3S, 4R |
| 5 | NO₂ | 6 | CH₃ | | OH | NO₂ | 4 | H | — | 0 | 2R, 3R, 4S |
| 6 | NO₂ | 6 | CH₃ | | OH | CF₃ | 3 | H | — | 0 | 2R, 3R, 4S |
| 7 | NO₂ | 6 | CH₃ | | OH | CF₃ | 3 | H | — | 0 | 2R, 3S, 4R |
| 8 | NO₂ | 6 | CH₃ | | OH | OCH₃ | 4 | H | — | 0 | 2R, 3R, 4S |
| 9 | NO₂ | 6 | CH₃ | | OH | OCH₃ | 4 | H | — | 0 | 2R, 3S, 4R |
| 10 | NO₂ | 6 | CH₃ | | OH | Cl | 4 | H | — | 0 | 2S, 3R, 4S |
| 11 | NO₂ | 6 | CH₃ | | OH | Cl | 4 | H | — | 0 | 2S, 3S, 4R |
| 12 | NO₂ | 6 | CH₃ | | OH | Cl | 3 | H | — | 0 | 2S, 3R, 4S |
| 13 | NO₂ | 5 | CH₃ | | OH | Cl | 3 | H | — | 0 | 2S, 3S, 4R |
| 14 | NO₂ | 6 | CH₃ | | OH | CF₃ | 3 | H | — | 0 | 2S, 3R, 4S |
| 15 | NO₂ | 6 | CH₃ | | OH | CF₃ | 3 | H | — | 0 | 2S, 3S, 4R |
| 16 | NO₂ | 6 | CH₃ | | OH | OCH₃ | 4 | H | — | 0 | 2S, 3R, 4S |
| 17 | NO₂ | 6 | CH₃ | | OH | OCH₃ | 4 | H | — | 0 | 2S, 3S, 4R |
| 18 | NO₂ | 6 | CH₃ | | OH | CH₃ | 4 | H | — | 0 | 2R, 3R, 4S |
| 19 | NO₂ | 6 | CH₃ | | OH | CH₃ | 4 | H | — | 0 | 2R, 3S, 4R |
| 20 | NO₂ | 6 | CH₃ | | OH | OCH₃ | 4 | H | — | 1 | 2R, 3R, 4S |
| 21 | NO₂ | 6 | CH₃ | | OH | OCH₃ | 4 | H | — | 1 | 2R, 3S, 4R |
| 22 | NO₂ | 6 | CH₃ | | OH | H | — | H | — | 1 | 2R, 3R, 4S |
| 23 | NO₂ | 6 | CH₃ | | OH | H | — | H | — | 1 | 2R, 3S, 4R |
| 24 | NO₂ | 6 | CH₃ | | OH | H | — | H | — | 1 | 2S, 3R, 4S |
| 25 | NO₂ | 6 | CH₃ | | OH | H | — | H | — | 1 | 2S, 3S, 4R |
| 26 | H | 6 | CH₃ | | OH | Cl | 4 | H | — | 0 | 2R, 3R, 4S |
| 27 | H | 6 | CH₃ | | OH | Cl | 4 | H | — | 0 | 2R, 3S, 4R |
| 28 | NO₂ | 6 | CH₃ | CH₂OH | OH | Cl | 4 | H | — | 0 | 2R, 3R, 4S |
| 29 | NO₂ | 6 | CH₃ | CH₂OH | OH | Cl | 4 | H | — | 0 | 2R, 3S, 4R |
| 30 | NO₂ | 6 | CH₃ | CH₂OCH₃ | OH | Cl | 4 | H | — | 0 | 2R, 3R, 4S |
| 31 | NO₂ | 6 | CH₃ | CH₂OCH₃ | OH | Cl | 4 | H | — | 0 | 2R, 3S, 4R |
| 32 | NO₂ | 6 | CH₃ | CH(OMe)₂ | OH | Cl | 2 | H | — | 0 | 2S, 3R, 4S |
| 33 | NO₂ | 6 | CH₃ | CH(OMe)₂ | OH | Cl | 2 | H | — | 0 | 2S, 3S, 4R |
| 34 | NO₂ | 6 | CH₃ | | OH | CF₃ | 2 | H | — | 0 | 2S, 3R, 4S |
| 35 | NO₂ | 6 | CH₃ | | OH | CF₃ | 2 | H | — | 0 | 2S, 3S, 4R |
| 36 | NO₂ | 6 | CH₃ | | OH | Cl | 2 | H | — | 0 | 2S, 3R, 4S |
| 37 | NO₂ | 6 | CH₃ | | OH | Cl | 2 | H | — | 1 | 2S, 3S, 4R |
| 38 | NO₂ | 6 | CH₃ | | OAc | H | — | H | — | 1 | 2S, 3S, 4R |
| 39 | NO₂ | 6 | CH₃ | | OH | H | — | H | — | 1 | 2S |

| No | R₁ S | R₁ P | R₂ | R₃ | R₄ | R₅ S | R₅ P | R₆ S | R₆ P | n | Stereo chemistry |
|---|---|---|---|---|---|---|---|---|---|---|---|
| 40 | NH₂ | 6 | CH₃ | CH(OMe)₂ | OH | H | — | H | — | 1 | 2S, 3S, 4R |
| 41 | NHCOCH₃ | 6 | CH₃ | | OH | H | — | H | — | 1 | 2S, 3S, 4R |
| 42 | NHSO₂CH₃ | 6 | CH₃ | | OH | H | — | H | — | 1 | 2S, 3S, 4R |
| 43 | CN | 6 | CH₃ | | OH | Cl | 4 | H | — | 0 | 2S, 3S, 4R |
| 44 | CN | 6 | CH₃ | | OH | Cl | 4 | H | — | 0 | 2S, 3R, 4S |
| 45 | CN | 6 | CH₃ | | OH | H | — | H | — | 1 | 2S, 3S, 4R |
| 46 | CN | 6 | CH₃ | | OH | H | — | H | — | 1 | 2S, 3R, 4S |
| 47 | Br | 6 | CH₃ | | OH | H | — | H | — | 1 | 2S, 3S, 4R |
| 48 | NO₂ | 6 | CH₃ | | OH | OCH₃ | 4 | OCH₃ | 3 | 1 | 2S, 3S, 4R |
| 49 | NH₂ | 6 | CH₃ | | OH | OCH₃ | 4 | OCH₃ | 3 | 1 | 2S, 3S, 4R |
| 50 | NO₂ | 6 | CH₃ | | OH | OCH₃ | 4 | H | — | 1 | 2S, 3S, 4R |
| 51 | NH₂ | 6 | CH₃ | | OH | OCH₃ | 4 | H | — | 1 | 2S, 3S, 4R |
| 52 | NO₂ | 6 | CH₃ | | OH | NO₂ | 3 | H | — | 1 | 2S, 3S, 4R |
| 53 | NO₂ | 6 | CH₃ | | OH | CF₃ | 3 | H | — | 1 | 2S, 3S, 4R |
| 54 | NH₂ | 6 | CH₃ | | OH | CF₃ | 3 | H | — | 1 | 2S, 3S, 4R |
| 55 | SO₂CH₃ | 6 | CH₃ | | OH | H | — | H | — | 1 | 2S, 3S, 4R |
| 56 | SO₂CH₃ | 6 | CH₃ | | OH | H | — | H | — | 1 | 2R, 3R, 4S |
| 57 | NH₂ | 6 | CH₃ | | OH | H | — | H | — | 1 | 2S, 3R, 4S |
| 58 | NH₂ | 6 | CH₃ | | OH | H | — | H | — | 1 | 2S, 3R, 4S |
| 59 | NH₂ | 6 | CH₃ | | OH | H | — | H | — | 1 | 2R, 3S, 4R |
| 60 | NO₂ | 6 | CH₃ | | OH | H | — | H | — | 1 | 2S, 3S, 4R |
| 61 | NH₂ | 6 | CH₃ | 2-methyl-1,3-dioxolane | OH | H | — | H | — | 1 | 2S, 3S, 4R |
| 62 | BO₂ | 6 | CH₃ | 2-methyl-1,3-dioxane | OH | H | — | H | — | 1 | 2S, 3S, 4R |
| 63 | NH₂ | 6 | CH₃ | | OH | H | — | H | — | 1 | 2S, 3S, 4R |

TABLE 1-continued

| 64 | NO$_2$ | 6 | CH$_3$ | (tetrahydropyran-dimethyl) | OH | H | — | H | — | 1 | 2S, 3S, 4R |
| 65 | NH$_2$ | 6 | CH$_3$ | | OH | H | — | H | — | | 2S, 3S, 4R |
| 66 | NO$_2$ | 6 | CH$_3$ | CH(OEt)$_2$ | OH | H | — | H | — | 1 | 2S, 3S, 4R |
| 67 | NH$_2$ | 6 | CH$_3$ | | OH | | | — | — | 1 | 2S, 3S, 4R |
| 68 | CO$_2$CH$_3$ | 6 | CH$_3$ | CH(OMe)$_2$ | OH | H | — | H | — | 1 | 2S, 3S, 4R |
| 69 | CO$_2$CH$_3$ | 6 | CH$_3$ | | OH | H | — | H | — | 1 | 2R, 3S, 4R |
| 70 | NO$_2$ | 8 | CH$_3$ | | OH | H | — | H | — | 1 | 3S, 4R |
| 71 | NH$_2$ | 8 | CH$_3$ | | OH | H | — | H | — | 1 | 2S, 3S, 4R |
| 72 | NH$_2$ | 8 | CH | | OH | H | — | H | — | 1 | 2R, 3S, 4R | a: S represents substituent.
b: P represents position.
*The compound of No. 39 has a double bond at 3,4-position.

EXPERIMENTAL EXAMPLES

The following experiments were made on the compounds of the formula 1 to investigate their pharmacological actions.

Experimental Example 1

Vasodilation Effects on Isolated Blood Vessels of Rats

The following experiment was conducted to examine whether the compounds of the formula 1 dilate blood vessels.

Male Sprague-Dawly rats (350–450 g, obtained from the Experimental Animal Team of the Korea Research Institute of Chemical Technology) were knocked uncious by hitting the occipital region, sacrificed by cervical dislocation, and underwent thoracotomy. After being quickly removed, the thoracic aorta was deprived of the adipose tissue and cut into aortic rings of 3 mm width. The aorta was lightly rubbed with a modified Krebs Henseleit buffer (Physiological Salt Solution, PSS) soaked cotton club to remove the inner epithelial layer therefrom. While being suspended in an organ bath containing a physiological buffer, the vascular tissue was allowed to equilibrate under a resting tension of 2 g and then, stand for 1 hour at 37° C. for stabilization with a supply of a carbogen consisting of 95% $O_2$–5% $CO_2$.

Thereafter, the vascular tissue was constricted with $10^{-5}$ M phenylephrine and washed several times with PSS and this procedure was repeated again to ensure the stable reacivity of vascular smooth muscle to repetitive triction/dilatation.

In addition, $3\times10^{-6}$ M methoxamine was used to induce an intensive triction in the vascular smooth muscle. When the vasoconstriction induced by the methoxamine reached and maintained a maximum, test compounds and controls were cumulatively added to the organ baths in concentrations of 1, 3, 10 and 30 uM so as to induce vasodilatation. As for the controls, they were Cromakalim and BMS-180448 (the compounds of the chemical formula 2), both known to be the first generation K.,, activator with potent vasodilatation and cardioprotection effects.

Following the addition of the drugs, the change in the maximal triction induced by methoxamine was calculated to plot a concentration-dilation response curve. Through a linear regression analysis, $IC_{50}$, the drug concentration at which the vascular tissue is 50% dilated, was obtained for each drug. The results are given in Table 2, below.

TABLE 2

Vasodilation and Anti-Ischemic Effect (Cardioprotective Effect) of Compounds of Formula 1

| Test Drugs | Experimental Example 1 Vasodilation Activity (in Vitro, rat aorta) ($IC_{50}$, uM) | Experimental Example 2 Anti-ischemic Activity (in vivo, rats) (0.3 mg/kg i.v.) | | Experimental Example 3 Anti-ischemic Activity (in vivo, dogs) (2 mg/kg/40 min, i.v.) | |
|---|---|---|---|---|---|
| | | AAR/LV (%) | IZ/AAR (%) | AAR/LV (%) | IZ/AAR (%) |
| Vehicle | — | 39.75 | 60.78 | 37.61 | 52.39 |
| Cromakalim | 0.067 | | | | |
| BMS-180448 | 1.38 | 38.83 | 39.14 | 37.73 | 38.02 |
| Exmp. 15 | 14.07 | | | | |
| Exmp. 24 | 9.78 | 37.92 | 48.48 | 35.33 | 28.03 |
| Exmp. 25 | >30 | 36.88 | 48.55 | | |
| Exmp. 32 | 3.57 | 42.49 | 44.72 | | |
| Exmp. 38 | 24.48 | 38.26 | 51.13 | | |
| Exmp. 41 | >30 | 33.59 | 30.25 | | |
| Exmp. 41 | >30 | | | | |

Cromakalim had an $IC_{50}$ of 0.067 uM and showed a potent dilation effect on the isolated rat aorta constricted with methoxamine (3 uM) while BMS-180448 was 1.38 uM in $IC_{50}$, showing a vasodilatation activity twenty times as weak as Cromakalim. On the other hand, the compounds of the present invention ranged, in $IC_{50}$, from 9.78 uM to greater than 30 uM, so that their vasodilatation effects were, very little, even smaller than those of the controls, Cromakalim and BMS-180448.

When exerting their actions on the KIT present in the heart, the compounds according to the present invention play a role in protecting the heart. On the other hand, the benzopyranyl guanidine derivatives acting on the $K_{ATP}$ present in peripheral blood vessels dilate the blood vessels, decreasing the blood pressure. Therefore, the compounds of the present invention have more efficient cardioprotective effects by virtue of their low vasodilatation activity.

As illustrated above, the compounds of the present invention are so low in the activity of dilating the blood vessels that they are improved in the selectivity for heart protective function.

Experiment Example 2

Heart Protective Activity in Ischemic Heart Models of Rats

In order to determine whether the compounds of the formula 1 are protective for ischemic hearts, experiments determining the anti-ischemic effects of the compounds on rats were conducted as follows.

Male rats (350–450 g, obtained from the Experimental Animal Team of the Korea Research Institute of Chemical Technology) were anesthetized by the intraperitoneal injection of pentobarbital at a dose of 75 mg/kg. After trachetomy, the rats were rendered to respire artificially at a rate of 60/min with a stroke volume of 10 ml/kg.

Cannulars were inserted into the fermoral vein and the fermorat artery and used for drug administration and blood pressure measurement, respectively.

In the ischemic myocardium damage models, the body temperature has an important influence on the results. To avoid the change in the body temperature, a body temperature measuring probe was inserted into the rectum of each rat and the body temperature was tantly kept at 37° C. with the aid of a homeothermic blanket control unit.

Afterwards, during testing, a continuous measurement was made of the mean arterial blood pressures and heart rates from the rats. For the measurement of the blood pressure, a pressure transducer, such as that manufactured by Grass Ins., MA, U.S.A., identified as Model Statham P23XL, was used. The heart rate was measured by a tachometer, such as that manufactured by Gould Inc., OH, U.S.A., identified as Biotachometer. in addition, all of the changes occuring were continuously recorded through the Gould 2000 chart recorder, manufactured by Gould Inc.

The left coronary artery was occluded according to the Selye H. method as follows. The rats underwent a left thoracotomy operation for partial opening of the chest and the right-side chest was pressurized by the middle finger of the left hand to push the heart out. Immediately after the left anterior descending coronary artery hereinafter referred to as (LAD) was carefully stitched using a suture needle with 5-0 silk ligature, the heart was then repositioned in the thoracic cavity while both ends of the ligature were situated outside. The opposite ligature ends were passed through a PE tube (PE100, 2.5 cm) and allowed to stand loose for 20 min for stabilization. Via the cannula inserted into the femoral vein, vehicles or drugs were administered into the rats which were rendered to stand for 30 min in order to sufficiently elicit the efficacies of the drugs. BMS-180448 was used as a control drug and the i.v. administration dose was 0.3 mg/kg for all test drugs of interest and the control drug.

Next, the PE tube which had the doubled strands of the ligature passed therethrough was pushed toward the heart and then, set upright by tightly pulling end regions of the ligature wits a hemostatic pincette while pressing the coronary artery. The PE tube was allowed to stand or 45 min for the occlusion of the coronary artery, followed by the removal of the hemostatic pincette and then, by the reperfusion for 90 min.

After the reocclusion of the coronary artery in accordance with the above procedure, the rats were administered with 2 ml of 1% Evans blue through an intravenous route. Subsequently, an excess of pentobarbital was intravenously injected to kill the rats, after which the heart was removed and then, deprived of the right ventricle and both atria. The left ventricle was cut horizontally to the heart apex into 5 or 6 slices which were weighed. From the surface of each slice, images were input with the aid of a Hi-scope into a computer installed with an image analyzing program (Image Pro Plus). From the images input into the computer, the area of the normal blood stream tissue region which appeared blue in a computer monitor and the area which appeared colorless were measured. The percentage of the colorless area to the total area of each slice was calculated and multiplied by the weight of each slice to determine the area at risk (AAR) of each slice. The AAR obtained from each slice was summed for all slices and the total AAR was divided by the total weight of the left ventricle to yield h AAR, as shown in the following mathematical formula 1:

[Mathematical Formula 1]

$$\% \, AAR = \frac{\sum AAR \text{ of Each Slice}}{\text{Total LeftVentricle Weight}}$$

In addition, the heart slices were incubated for 15 min in 2,3,5-triphenyltetrazolium chloride (TTC) phosphate buffer (pH 7.4) at 37° C. and fixed for 20–24 hours in a 10% formalin solution. During this fixation, 2,3,5-triphenyltetrazolium chloride was reduced into formazan dye by the myocardial dehydrogenase and its cofactor NADH, so that the normal regions of the tissue were colored brick-red. In contrast, the infarct zones of the tissue were deficient in the dehydrogenase and its cofactor, so that no reduction occurred on the 2,3,5-triphenyltetrazolium, allowing the color to remain unchanged.

According to whether the tissue regions were colored by 2,3,5-triphenyltetrazolium, a measurement was made of the areas of the normal and infarct zones in each ventricle slice. The infarct zone area of each slice was summed for all slices and the resulting summed infarct zone area was divided by total AAR weight or total left ventricle weight to yield% IZ as shown in the following mathematical formula 2:

[Mathematical Formula 2]

$$IZ(\%) = \frac{\sum \text{Infarct Region Area of Each Slice}}{\text{Weight of Total Ventricle V Total } AAR}$$

In this experimental model, some of the test drugs were determined as being of more potent anti-ischemic activity as the % IZ was smaller. The results are given in Table 2, above.

In the ischemic myocardium damage model of anesthetized rats, as seen in Table 2, the vehicle-administered group showed a myocardial infarction rate to area at risk (IZ/AAR) of 60.78%, which indicates a serious damage in the myocardial muscle. Being measured to be 39.14% in myocardial infarction rate, BMS-180448 showed noticeable anti-ischemic activity. When compared only in myocardial infarction rate, the compounds of the present invention were similar to or superior to BMS-180448. However, because the compounds of the present invention are remarkably lower in vasodilatation activity than is BMS-180448, they are far superior to the conventional drug in heart-selective anti-ischemic activity. Especially, the compound of Example 40 was of very Slow vasodilatation activity ($IC_{50}$>30 uM) with a myocardial infarction rate of as low as 30.25%, so it shows much better heart selectivity upon vasodilatation than is BMS-180448. Further, the compounds of the present invention did not act to reduce the blood pressure. Consequently, the compounds of the present invention can be used as an agent for the treatment of ischemic heart diseases by virtue of their excellent protective activity against ischemic cardiovascular diseases.

Experimental Example 3

Heart Protective Activity in Ischemic Heart Models of Beagle Dogs

In order to determine whether the compounds of the formula are protective for the ischemic hearts of larger animals, experiments determining the anti-ischemic effects of the compounds on beagle dogs were conducted as follows. The experiments on beagle dogs followed the method of Grover et al.' (G. J. Grover et al., *J. Cardiovasc. Pharmacol.* 25, 40 (1995)).

After being anesthetized by an intravenous injection of pentobarbital at a dose of 35 mg/kg, male beagle dogs (8–12 kg) were further infused with pentobarbital sodium at a dose of 3–4 mg/kg through the right cephalic vein throughout the experiments, so as to keep the anesthesia constant. For the maintenance of breathing during the experiment, a tracheal catheter was inserted into the respiratory tract of each beagle dog, after which they were allowed to respire with the aid of a respirator, such as that manufactured by CWE Inc., PA, U.S.A., identified as Model SAR-830, while the $pCO_2$ was maintained at 30–35 mmHg by use of room air and supplied oxygen. 0.5 ml of blood was taken through a catheter inserted into the femoral artery each hour and used to measure the oxygen level in blood with the aid of an apparatus, such as that manufactured by Ciba-Corning, MA, U.S.A., identified as Blood Cas Analyzer 280. While monitoring the temperature obtained at the recta, the body temperature of the experimental animals was maintained constantly (38° C.) by controlling the temperature of the laboratory tables on which the animals were laid. With the aim of measuring the blood pressure and the heart rate, a heparinized catheter was inserted into the right femoral artery. In this regard, a pressure transducer, such as that manufactured by Grass Ins., MA, U.S.A., identified as Model Statham P23XL, was used to measure the blood pressure. The heart rate was measured by a tachometer, such as that manufactured by Gould Inc., OH, U.S.A., identified as Biotachometer. In addition, all of the changes occurring during the experiment were continuously recorded through the Gould 2000 chart recorder, manufactured by Gould Inc.

The fifth intercostal space was incised to open the thorax and the TAD was separated from its surrounding tissues. A silk ligature was hung around the LAD to occlude the LAD, later. The LAD part upstream of the silk ligature was isolated from adjacent tissues and the blood flow was measured quantitatively. In this regard, a chart recorder, such as that manufactured by MFE Ins., MA, U.S.A., identified as 1400 Thermal Chart Recorder was used. Using polygraph such as Grass Model 7E, the electrocardiogram was measured and read (Lead II). For infusing the beagle dogs with the drugs of interest, a catheter was inserted into the left cephalic vein and fixed. After the operation, when all parameters were maintained stable, test compounds and vehicles were administered intravenously.

Before the occlusion of the LAD, the experimental animals were divided into a control group (PEG 400) and a test drug-administered group (KR-31372, 50 ug/kg/min). Ten minutes before the occlusion of the LAD, test drugs began to be infused through an intravenous route. The infusion of the test drugs and the vehicle lasted for 40 min. (total dose 2 mg/kg, total PEG400 volume 4 ml or less). Ten min. after the beginning of the infusion, the LAD was completely occluded and after a lapse of 90 min, reperfusion was conducted to maintain coronary flow for five hours. After 5 hours, the LAD was cannulated for perfusion with a Ringer's solution at the same pressure as the blood pressure.

A blue violet dye solution (1 mg/kg, 10 mg/ml) was injected into the left atrium, after which the heart was endered to get an electric shock and removed. After removal of both atria, the ventricles were transversely cut t an interval of 0.5 cm. Photographs were taken of the transverse sections of the resulting ventricle slices by a digital camera. For the measurement of the IZ, the tissue slices were incubated at 37° C. for 30 min in a 1% 2,3,5-triphenyltetrazolium chloride phosphate buffer, followed by taking photographs of the transverse sections with the digital camera. Using an image analyzing program (Image-Pro Plus ver. 3.0.1, Media Cybernetics, Maryland, U.S.A.), the AAR and the IZ were measured and analyzed. The IZ was expressed as a percentage to the AAR (refer to the mathematical formula 2). Lower IZ values mean more potent effects of the test drugs on this beagle dog model. The results are given in Table 2, above.

In the ischemic myocardium damage models of anesthetized beagle dogs, as indicated in Table 2, the compounds of the present invention also showed iderably decreased values for the myocardial infarction rate in the area at risk(AAR). In detail, the solvent group showed a myocardial infarction rate to area at risu (IZ/AAR) of 52.39%, which indicates a serious damage in the myocardial muscle. Being measured to be 38.02% in myocardial infarction rate, BMS-180448 showed a good anti-ischemic activity. On the other hand, when the compounds of the present invention were administered, the myocardial infarction rate was decreased down to as low as 28.03% (compound of Example 24). Of course, no significant reduction in the blood pressure was found upon the administration of the compounds of the present invention.

As described above, the compounds of the present invention exert excellent anti-ischemic action on beagle dog with superiority in anti-ischemic activity to the control BMS-180448. Therefore, the compounds of the present invention can be used as preventive or curative agents against the diseases related to ischemic heart disease.

Experimental Example 4

Protective Activity for Neurons

In order to examine whether the compounds of the formula 1 suppress the iron-induced neuronal death, experiments were conducted as follows.

From the brains of 17–18 day-old rat embryos, cerebra. cortical neurons were isolated and then, cultured at 37° C. for 7–9 days in a 5% $CO_2$ incubator. The cortical cell cultures were washed twice with a minimum essential medium (MEM) to reduce tiLe serum concentration to 0.2% and pre-treated for 30 min with 10 uM and 30 uM of each of test compounds. For the experiments, the test compounds were dissolved in DMSO and diluted in a medium. At this time, the final concentration of DMSO was not allowed to exceed For a control group, only vehicle was applied.

After the pre-treatment with test compounds or vehicle, $FeSO_4$, was added to a final concentration of 50 uM, and the cultures were maintained for 24 hours in a $CO_2$ incubator. During incubation, lactate dehydrogenase (LDH) was released into the medium upon neuronal death by the oxidative toxicity of iron. The extent of neuronal damage was assessed by measuring the amount of LDH secreted into the media. The protective effect of the compounds of interest on neurons was evaluated beg calculating the LDH reduction rate of treatment group compared with that of the control group. The results are given in Table 3, below.

TABLE 3

Protective Effect of Compounds of Formula 1 on Neurons

| Compounds | Concentration (uM) | % Protection |
|---|---|---|
| Example 24 | 30 | 47 |
| | 10 | 29 |
| Example 25 | 30 | 69 |
| | 10 | |
| Example 38 | 30 | 78 |
| | 10 | 56 |
| Example 40 | 30 | 97 |
| | 10 | 45 |

As seen in Table 3, the compounds of the present invention protected neurons from being damaged by iron in a dose-dependent manner. The compound of Example 38 protected the neuronal death by as high as 56% even at 10 uM. In addition, the compound of Example 40 showed a protection rate of as high as 97%, which demonstrates that the compound has very potent protective activity against the iron-included damage to neurons.

Since the compounds of the present invention showed an excellent protective effects on neurons, they can be used as preventive or curative agents for the medical treatment of the neurological disorders caused by the (damage or death of neurons, such as cerebral stroke and dementia as well as for the medical treatment of inflammatory diseases such as arthritis, cardiac infarction, and acute/chronic tissue damage.

Experimental Example 5

Inhibitory Activity Against Lipid Peroxidation
(1) Inhibitory Effect on Iron-induced Lipid Peroxidation In order to examine whether the compounds of the formula 1 suppress the iron-induced lipid peroxidation, experiments were conducted as follows.

The rat brain was homogenized in a Krebs buffer (15 mM HEPES, ID mM glucose, 140 mM NaCl, 3.6 mM KCl, 1.5 mM $CaCl_2$, 1.4 mM $KH_2PO_4$, 0.7 mM $MgCl_2$, pH 7.4) and the supernatant separated by centrifugation at 12,000 rpm for 10 min. was used for further experiments. $FeCl_2$ was added to a final concentration of 400 uM in the brain homogenate which was then allowed to stand at 37° C. for 30 min. for the facilitation of oxidation. Each of the test compounds was added at a concentration of 100 uM and vehicle was used as a control.

Iron facilitates the oxidation of the brain homogenate to produce malondialdehydo (MDA), a lipid peroxidation product. Thus, the lipid peroxidarion was determinne by MDA quartification. The inhibitory effect of the test compounds against the lipid peroxidation was evaluated by calculating MDA reduction rate of the test compounds compared with that of the control group.

Typically, the MDA quantification is achieved by reacting samples with 2-thiobarbituric acid (TBA) and measuring the absorbance at 530 nm. However, this method is unsuitable to treat samples on a large scale because of a boiling step. Thus, in this experiment, N-methyl-2-phenylindole was used instead of TBA. In this case, one molecule of MDA reacts with two molecules of N-methyl-2-phenylindole to form a chromogen which shows a maximal absorbance at 586 nm and requires no boiling steps. Bioxytech[R] LPO-586 Kit was used for MDA quantification. The results are given in Table 4a, below.

TABLE 4a

Inhibitory Effect of Compounds of Formula 1 on Lipid Peroxidation by iron

| Compounds | Concentration (uM) | % Inhibition |
|---|---|---|
| Example 7 | 100 | 70 |
| Example 24 | 100 | 12 |
| Example 25 | 100 | 2 |
| Example 32 | 100 | 86 |
| Example 38 | 100 | 4 |
| Example 40 | 100 | 79 |

As seen in Table 4a, the compounds of the present invention suppress the iron-induced lipid peroxidation. In particular, the compounds of Examples 7, 32 and 40 showed very potent inhibitory activity against the iron-induced lipid peroxidation with inhibitory effects of 70%, 86% and 79%, respectively.

(2) Inhibitory Effect on Copper-induced LDL Oxidation

In order to examine whether the compounds of the formula 1 suppress the oxidation of LDL (low density lipoprotein) induced by copper, experiments were conducted as follows.

ID Human LDL (sigma) was dissolved in distilled water at a concentration of 1 mg/ml. LDL was dialyzed against three changes of phosphate-buffered solution before oxidation to remove EDTA (ethylenediamine tetraacetate) at 4° C. for 18 hr. EDTA-free LDL (100 ug LDL protein/ml) was incubated in EDTA-free phosphate-buffered solution at 37° C. for 18 hr in the presence of $CuSO_4$ (10 uM) under pretreatment with the test compounds or tochopherol of which final concentrations were $10^{-9}$, $10^{-7}$, and $10^{-5}$ M. Blank was incubated without CuSO, and vehicle was used as a solvent group. Oxidation was stopped at 4° C. by addition of EDTA (200 uM).

Copper ($Cu^{+2}$) facilitates the oxidation of LDL to produce malondialdehyde (MDA), thus the lipid peroxidation was determined by MDA quantification same as the above example 5 (1). The MDA quantification was estimated by reacting samples with 2-thiobarbituric acid (TBA) and measuring the absorbance at 530 nm. 1,1,3,3-Tetramethoxy propane (Sigma) was used as a standard agent, and calculated the quantity of MDA as nmol of MDA equivalents per mg protein. The inhibitory effect of the test compounds against the lipid peroxidation was evaluated by calculating MDA reduction rate of the test compounds compared with that of the control group. The results are given in Table 4b, below.

TABLE 4b

Inhibitory Effect of Compounds of Formula 1 on Lipid Peroxidation induced by copper

| Compounds | Concentration (M) | % Inhibition |
|---|---|---|
| Example 40 | $10^{-9}$ | 7.6 |
| | $10^{-7}$ | 24.3 |
| | $10^{-5}$ | 27.6 |
| Tocopherol | $10^{-9}$ | 18.5 |
| | $10^{-7}$ | 21.3 |
| | $10^{-5}$ | 29.7 |

As seen in Table 4b, the compound of example 40 significantLy suppress the copper-induced LDL oxidation at concentration of $10^{-7}$ and $10^{-5}$ M, which was similar to that of tocopherol.

(3) Inhibitory Effect on A7r5 Mediated LDL Oxidation

In order to examine whether the compounds of the formula 1 suppress the A7r5 mediated oxidation of LDL (low density lipoprotein), experiments were conducted as follows.

A7r5 (ATCC CAL-1444, smooth muscles, thoracic aorta, BDIX rat) cells were cultured in 24 well plates, using the medium of DMEM (Dulbecco's modified Eagle's Medium) supplemented with 10% heat-inactivated FBS (fetal bovine serum) and 1% antibiotics. Confluent A7r5 from plates were washed with phosphate-buffered solution, and DMEM with 10% FBS and 1% antibiotics was added in a total volume of 0.5 ml/well. Cells ($2\times10^5$ cells/ml) were preincubated without and with either test compounds ($10^{-6}$–$10^{-4}$ M) or Tocopherel ($10^{-6}$–$10^{-4}$ M) at 37° C. for 30 min. Then, A7r5 alone or A7r5 plus $H_2O_2$ ($10^{-7}$ M) were exposed to LDL (100 ug/ml) for 24 hr.

The inhibitory effect of the test compounds against the lipid peroxidation was evaluated by calculating MDA reduction rate of the test compounds compared with that of the control group same as the above example 5 (2). The results are given in Table 4c, below.

TABLE 4c

Inhibitory Effect of Compounds of Formula 1 on A7r5 mediated LDL oxidation

| Compounds | Concentration (M) | % Inhibition | |
|---|---|---|---|
| | | LDL | LDL + $H_2O_2$ ($10^{-7}$M) |
| Example 40 | $10^{-6}$ | 40.9 | 49.7 |
| | $10^{-5}$ | 51.4 | 62.5 |
| | $10^{-4}$ | 57.5 | 64.3 |
| Tocopherol | $10^{-6}$ | 41.1 | 43.2 |
| | $10^{-5}$ | 57.0 | 53.0 |
| | $10^{-4}$ | 73.7 | 63.9 |

As seen in Table 4c, the compound of example 40 and Tocopherol significantly suppress the A7r5 mediated LDL oxidation at all concentrations tested. Especially, the compound of example 40 represented more significant inhibition of LDL oxidation when $H_2O_2$ was added.

With excellent inhibitory activity against lipid peroxidation as seen in the above experimental example 5 (1), (2), and 3), the compounds of the present invention can be used for the prevention and treatment of neurodegenerative diseases such as cerebral stroke and dementia, inflammatory diseases such as arthritis, cardiac infarction, and acute/chronic tissue damage, which may be caused by the lipid peroxidation and its accumulation in tissues.

Experimental Example 6

Inhibitory Effect on NO Production

In order to examine whether the compounds of the formula 1 inhibit the formation of nitric oxide (NO), experiments were conducted as follows.

Using RPMI1640 media supplemented with 10% fetal bovine serum (EBS), RAW 264.7 cells (obtained from American Type Culture Collection), a murine macrophage cell line, were cultured at 37° C. in a 5% $CO_2$ incubator. The RAW264.7 cells were harvested and cell density was adjusted to $5\times10^5$/ml with a RPMI medium supplemented with 0.5% FBS and plated at $5\times10^4$ cells/well to 96-well plates, which were then cultured for 20 hr in a $CO_2$ incubator. After removal of the media, the cells were pre-treated for 1 hour with fresh media containing 33 uM and 100 uM of test compounds. The test compounds were dissolved in DMSO and diluted to respective concentration in the media. In order to minimimize DMSO effect on the nitric oxide formation by the RAW264.7 cells in the wells, the media were allowed to contain DMSO at a concentration of 0.1% or less.

After completion of one hour pre-treatment, lipopolysaccharide (LPS, *E. coli* serotype 055:B5) was added to activate the cells, which were, then, maintained for 24 hours in a $CO_2$ incubator. As a result of the activation of RAW264.7 cells with LPS, NO was formed. The NO released into the media was in a form of nitrite $NO_2^-$ and quantitatively measured using the Griess reagent. A control was treated only with vehicle instead of test compounds. Using the nitrite standard it was shown that the test drugs themselves do not hinder the quantification of NO.

The inhibitory effects of the test compounds against NO production were determined as the reduction of NO quantity compared with that of the control group. The results are given in Table 5, below.

TABLE 5

Inhibitory Effect of Compounds of Formula 1 on NO Production

| Compounds | Concentration (uM) | % Inhibition |
|---|---|---|
| Example 7 | 100 | 88 |
| Example 24 | 100 | 48 |
| | 33 | 16 |
| Example 25 | 100 | 54 |
| | 33 | 39 |
| Example 32 | 100 | 83 |
| Example 38 | 100 | 85 |
| | 33 | 56 |
| Example 40 | 100 | 26 |

As indicated in Table 5, the compounds of the present invention exhibited a dose-dependent behavior in inhibiting the induction of NO production by endotoxins such as LPS. In particular, the compound of Example 38 inhibited the NO production by as high as 56% even at as low as 33 uM. In addition, 100 uM of the compounds of Examples 7 and 32 had inhibition rates of as high as 88% and 83%, respectively, showing that the compounds of the present invention exert very potent inhibitory activity against the NO production induced by LPS.

With good inhibitory activity against NO production, the compounds of the present invention can be used as preventive or curative agents for the medical treatment of neurological disorders such as cerebral stroke and dementia, which may be caused by the neuronal damage or death due to a large amount of NO released as well as for the medical treatment of inflammatroy diseases such as arthritis, cardiac infarction, and acute/chronic tissue damage.

Experimental Example 7

Preventive Effect on the Brain Damaged Induced by Brain Ischemia-Reperfusion in order to examine whether the compounds of the formula 1 are protective against the brain damage by brain ischemia-reperfusion, experiments were conducted as follows.

Male Sprague-Dawley rats (350±50 g, SamYook Experimental Animals Co., Korea) were anesthetized by the injection of pentobarbital sodium at a dose of 40 mg/kg, after which the femoral vein and the artery were cannulated with PE-10 while the left carotid artery was exposed. Five min. before the operation, 20 ug/kg of heparin sulfate was injected into the peritoneal cavity. For the continuous measurement of arterial pressure, with a insertion of a blood pressure measuring device into the femoral artery. About 10 ml of blood was taken from the femoral vein to reduce the blood pressure down to 30 mmHg. If the blood pressure is not reduced to less than 100 mmHg with a withdrawal of 7 ml of blood, the rats are considered to have high sympathetic tone. In such a case, those rats were excluded from the experiments because the blood pressure cannot be reduced to 30 mmHg or even after success in reducing the blood pressure, the rats showed high mortality after the operation.

While the blood pressure was maintained at 30 mmHg, the exposed left carotid artery was occluded for 20 min by an aneurysm clamp to cause cerebral ischemia. Then, the carotid clamps were removed and the extracted blood was reinfused. To minimize the systemic acidosis, the rats were reinfused with 5 ml of saline containing 0.84% bicarbonate sodium (bicarbonate saline). During operation and restoration period, body temperature was maintained at 37±0.5° C. with the aid of a thermal blanket and incandescent light bulbs. During their restoration from the operation, the body temperature was kept tant for 2 hours or more. After being completely recovered, the rats were transferred to an animal observatory, which was under a homeostatic condition for temperature (27° C.), humidity (60%) and light cycle (12–12 hours).

24 hours after the operation, the rats were sacrificed with a scaffold and the brain was removed rapidly (3 min). On ice, the removed brain was sliced into six 2-mm coronal sections with the aid of a brain matrix. The sections were stained in a 2% 2,3,5-triphenyltetrazolium chloride solution at 37° C. for 30 min. After photographs were taken of the stained sections, developed and printed, the percentages of the infarcted brain areas to the total brain were measured and analyzed using an image analyzing program (Image-Pro Plus ver. 3.0.1).

At 30 min before the operation and at 2, 4 and 16 hours after the carotid artery occlusion, the test compounds were peritoneally injected into the rats to a dose of 30 mg/kg. For the control, vehicle was injected. For the reference compound, MK801 (RBI, (SR,10S)-(+)-5-methyl-10,11-dihydro-5H-dibenzo[a,d]cyclo-heptene-5,10-imine hydrogen maleate) was administered at 3 mg/kg with the same intervals.

The protective effects of the test compounds on the brain damage caused by brain ischemia-reperfusion were expressed as a reduction percentages of infarcted brain areas compared with those of the control group. The results are given in Table 6, below.

TABLE 6

Protective Effect of Compounds of Formula 1 on Brain Damage Induced by Brain Ischemia-Reperfusion

| Test Drug | Dose (mg/kg) | Infarction Area Mean ± SD (%) | Reduction (%) | No. |
|---|---|---|---|---|
| Vehicle | 0 | 39.7 ± 1.6 | | 10 |
| NK801 | 3 | 29.8 ± 1.5 | 24.8* | 7 |
| Example 40 | 30 | 23.0 ± 3.3 | 42.0* | 11 |

$P < 0.01$ compared with the control group administered with only vehicle

The comparative group, in which rats were administered with MK801 at a dose of 3 mg/kg, had an infarct area of 29.8%, which was reduced by 24.8% compared with that of the control group. On the other hand, in the group treated with the compound of Example 40, the infarct area was measured to be 23.0%, which was reduced by 42.0% compared with that of the control group. Therefore, the compound of Example 42 was twice as effective in the protective activity against the brain damage cause by brain ischemia-reperfusion as the conventional compound MK801.

In the MK801-treuted group, the rats showed a side effect of low motility whereas when being administered with the compound of Example 40, the rats did not suffer from any side effects including behavorial change such as motility.

With excellent protective activity against brain damage induced by ischemia-reperfusion, the compounds of the present invention can be used as preventive or curative agents for the medical treatment of the neurological disorders such as cerebral stroke and dementia, which may be caused by the brain damage such as cerebral vascular occlusion induced by thrombi.

Experimental Example 8

Suppressive Effect Against Angiogenesis

In order to examine whether the compounds of the formula 1 had inhibitory effect on the formation of new blood vessels, experiments were conducted as follows.

(1) Effect on $^{99m}$Tc-DTPA Clearance

A polyester sponge with a size dimension of 5 mm×diameter 12 mm was used as a matrix for the growth of blood vessels. Inside each sponge, a polyethylene tube with a length of 5 mm was fixed by a thread. Sprague-Dawley rats were anesthetized by the intraperitoneal injection of chloral hydrate at a dose of 300 mg/kg. The rat's hair in the region between the neck and the dorsi was shaved and the hare regions were incised at a length of 10 mm to secure a hypodermic space large enough to accommodate the sponge. After being inserted to the hypodermic space, the sponge was secured for the tube not to rock. Except for when the drugs were administered, the tube hole was kept closed in order to prevent contamination.

In order to induce angiogenesis, Angiotensin II was employed. For use, Angiotensin II was dissolved in a phosphate buffered saline (PBS). 50 ul of a 100 nmol solution was injected. As for the compounds of the present invention, they were dissolved in PBS and injected at doses of 0.1, 0.3, and 1.0 mg/kg through the tube. In control groups, the vehicle PBS or Angiotensin II alone was injected at the same doses. The suppressive effect of the test compounds against angiogenesis was measured 7 days after the injection.

The extent of angiogenesis in transplanted sponge was examined for blood stream by the measurement of $^{99m}$Tc-DTPA (technetium-dimethylenetriamine pentaacetic acid) clearance. Seven days after the injection of the test compounds, the rats were again anesthetized by the intraperitoneal injection of chloral hydrate at a dose of 30 mg/kg, followed by careful injection of 50 ul of a solution of $^{99m}$Tc-DTPA (0.5 ) in sterilized PBS through the tube. A quantitative measurement of $^{99m}$Tc-DTPA was conducted for 60 min. With the aid of a gamma-scintillation dector while a gamma camera, such as ADAC VERTEX/SOLUS Gamma Camera, equipped with a low energy high resolution apparatus, was operated to take photographs of the sponge at 60 frames each which took 60 sec. to achieve. The continuous images thus obtained were input into a computer (Pegasys Sun Computer) for analysis.

The clearance of $^{99m}$Tc-DTPA was calculated according to the following mathematical formula 3 and the results are given in Table 7a, below.

[Mathematical Formula 3]

$$\text{Clearance of }^{99m}Tc\text{-}DTPA(\%) = \frac{\text{Initial RadioActivity} - \text{RadioActivity on the 6th min}}{\text{Initial RadioActivity}} \times 100$$

TABLE 7a

Suppressive Effect of Compounds of Formula 1 Against Angiogenesis

| | Test Drug | Dose (mg/kg) (p.o) | Clearance of $^{99m}$TC (%) |
|---|---|---|---|
| Control (PBS) | — | — | 30.3 |
| Control AII (100 nmol) | — | — | 44.71 |
| Test Group (AII (100 nmol) + Test Drug | Example 24 | 0.1 | 26.90 |
| | | 0.3 | 18.22 |
| | | 1.0 | 3.38 | p.o. per oral

As apparent from the data of Table 7a, Angiotensin II induced the formation of new blood vessels by comparing the clearance of $^{99}$mTc-DTPA between the PBS-administered control group (30.3%) and the Angiotensin II-administered control group (44.71%). When being administered at a dose of 0.1 mg/kg, the compound of Example 24 showed a $^{99m}$Tc-DTPA clearance of 26.90%, which clearly demonstrates the suppressive effect of the compound against the angiogenesis. In addition, the administration of the compound of Example 24 at doses of 0.3 and 1.0 mg/kg elicited $^{99m}$Tc-DTPA clearances of 18.22% and 3.38%, respectively, showing that the compound of the present invention suppresses the formation of new blood vessels in a dose-dependent manner. In particular, at a dose of 1.0 mg/kg, the compound of Example 24 showed almost complete suppression against the angiogenesis induced by Angiotensin II with the clearance of $^{99m}$Tc-DTPA as low as 3.38%.

(2) Inhibitory Effect on HUVEC Tube Formation

In order to examine whether the compounds of the formula 1 had inhibitory effect on the formation of new blood vessels on cell level, experiments were conducted as follows.

HUVEC, (Human umbilical vein endotheilal cells, ATCC CRL-1730) were cultured, and tubulogenesis was induced in vascular endothelial cells by plating them onto the surface of Matrigel for several hours. The effects on tube formation o)f the test compounds were compared with the vehicle treated controls, then confirmed their in vitro anti-arigiocenic effect indirectly. The results are given in table 7b).

TABLE 7b

Inhibitory Effects on HUVEC Tube Formation

| | Inhibitory Effects on Tube Formation | |
|---|---|---|
| Concentration | 10 uM | 100 uM |
| Example 2 | + | ++ |
| Example 10 | + | ++ |
| Example 16 | +/− | +/− |
| Example 24 | nd | + |

TABLE 7b-continued

Inhibitory Effects on HUVEC Tube Formation

| | Inhibitory Effects on Tube Formation | |
|---|---|---|
| Concentration | 10 uM | 100 uM |
| Example 40 | + | ++ |
| Example 52 | +/− | ++ |

−; no effect, +/−; week effect,
+; moderate effect, ++; strong effect
nd; not determined As seen in table 7b, HUVEC tube formation was inhibited ed at concentration of 10 uM, and strongly inhibited at concentration of 100 uM in the compounds of example 2, 10, 40, and 52, in a dose-dependent manner.

With such an excellent suppressive activity against angiogenesis, the compounds of the present invention can be usefully applied for the medical treatment of various diseases induced by angiogenesis, such as rheumatoid arthritis, psoriasis, AIDS complications, cancers, diabetic retinopathy, etc.

Experimental Example 9

Inhibitory Effect on Intracellular ROS Induced by Hydrogen peroxide

In order to examine whether the compounds of the formula 1 suppress the formation of intracellular ROS induced by $H_2O_2$, experiments were conducted as follows.

Measurement of intracellular ROS (Reactive Oxygen Species) was determined using $H_2$DCFDA (2',7'-dichlorodihydrofluorescein diacetate, Molecular Probes, Eugene, Oreg., USA). $H_2$DCFDA is a non-polar compound that readily diffused into cells, where it is hydrolyzed by intracellular esterase to polar derivative $H_2$DCF (2',7'-dichlorodihydrofluorescein) which can not cross the cell membrane, and thereby trapped within the cell. $H_2$DCF is low-fluorescent, but converted to high-fluorescent DCF (2', 7'-dichlorofluorescein) by intracellular a ROS. Therefore, the intracellular ROS formation can be determined from the amount of converted DCF. HUVEC (Human umbilical Vascular Endothelial Cells) or A7r5 (Rat thoracic aorta smooth muscle cells) were used. HUVEC were cultured in Kaighn's F12K medium supplemented with 10% heat-inactivated EBS, 0.1 mg/ml heparin sodium, 0.03–0.0 5 mg/ml ECGS (Endothelial cell growth supplement) and 1% antibiotics, and A7r5 were cultured in DMEM supplemented with 10% heat inactivated FBS and antibiotics. To measure the intracellular ROS, HUVEC or A7r5 were proincubated for 30 min in the presence of test compounds ($10^{-7}$–$10^{-5}$ M). Thereafter, cells were stimulated with $H_2O_2$ ($10^{-6}$ and $10^{-5}$ M for 20 min), and then incubated in the dark for 2 hr at 37° C. in 50 mM phosphate buffer (pH 7.4) containing 5 uM $H_2$DCFDA. The quantity of DCF fluorescence (485 nm excitation, 530 nm emission) was measured using Fluorescence plate reader (FL600, Biotek Instruments). The results are given in Table 8.

TABLE 8

Inhibitory Effects against intracellular ROS induced by $H_2O_2$

| Cell | Compounds | Conc. (M) | Inhibition (%) $H_2O_2$ ($10^{-6}$M) | $H_2O_2$ ($10^{-5}$M) |
|---|---|---|---|---|
| HUVEC | Tocopherol | $10^{-7}$ | 13.8 | 8.8 |
| | | $10^{-6}$ | 43.2 | 30.7 |
| | | $10^{-5}$ | 60.8 | 51.0 |
| | Example 40 | $10^{-7}$ | 17.6 | 12.0 |
| | | $10^{-6}$ | 46.1 | 25.8 |
| | | $10^{-5}$ | 63.1 | 54.9 |
| A7r5 | Probucol | $10^{-7}$ | 72.0 | |
| | | $10^{-6}$ | 184.1 | |
| | | $10^{-5}$ | 185.3 | |
| | Example 24 | $10^{-7}$ | 72.0 | |
| | | $10^{-6}$ | 110.7 | |
| | | $10^{-5}$ | 185.3 | |

As seen in table 8, the compound of example 40 inhibited $H_2O_2$-induced ROS in HUVEC cells, which is similar or a little superior to that of tocopherol. The compound of example 24 completely inhibited ROS at concentration of $10^{-6}$ and $10^{-5}$ M.

With excellent antioxidant effects to inhibit intracellular ROS formation, the compounds of the present invention can be used for the prevention and treatment of neurodegenerative diseases such as cerebral stroke and dementia; inflammatory diseases such as arthritis; atherosclerosis; cardiac infarction; and acute/chronic tissue damage, which may be caused by ROS.

Experimental Example 10

ORAC Assay

In order to examine whether the compounds of the formula 1 remove the oxygen-radical, experiments were conducted as follows.

The ORAC (Oxygen-radical absorbance capacity) assay is an in vitro method capable of assessing the radical absorbing capacity of a drug in a watery environment. The method utilized β-PE (β-phycoerythrin) as an indicator protein, and AAPH (2,2'-azobis(2-amidinopropane) dihydrochloride) as a peroxy radical generator. Reaction mixtures listed of test compounds ($10^{-6}$M and $10^{-4}$M), β-PE ($1.76 \times 10^{-8}$M), and AAPH ($3 \times 10^{-3}$M) in 75 mM phosphate buffer (pH 7.0). A final volume of 2 ml was used in 24 well plates. Test compounds were first dissolved in acetone and then added to the reaction mixture. Once AAPH was added, the reaction was initiated at 37° C. and the fluorescence (485 nm excitation, 590 nm emission) was measured every 5 min using Fluorescence reader (FL600, Biotek Instrument). The ORAC units were calculated based on the area under the fluorescence curve of β-PE in the presence of the test compound compared to the area generated by 1 uM Trolox. 1 ORAC unit represents the net protection provided by 1 uM Trolox. The results are given in table 9.

TABLE 9

ORAC Assay

| Compound | Conc. (M) | ORAC units |
|---|---|---|
| Tocopherol | $10^{-5}$ | 1.0 |
| | $10^{-4}$ | 1.568 |
| Probucol | $10^{-6}$ | 1.327 |
| | $10^{-4}$ | 1.566 |
| Example 40 | $10^{-6}$ | 2.047 |
| | $10^{-4}$ | 3.250 |

As seen in tabLe 9, the compound of example 40 showed around 2-Limes higher ORAC units compared to those of tocopherol and probucol at concentration of both $10^{-6}$ and $10^{-4}$ M, showing excellent radical absorbing capacity.

With excellent antioxidant effects to remove oxygen radicals, the compounds of the present invention can be used for the prevention and treatment of neurodeaenerative diseases such as cerebral stroke and dementia; inflammatory diseases such as arthritis; atherosclerosis; cardiac infarction; and acute/chronic tissue damage, which may be caused by free radicals.

Experimental Example 11

Protection Effects on Ischemic Retinal, Cells

In order to examine whether the compounds of the formula 1 protect the ischemic retinal cells, experiments were conducted as follows.

Test compounds were dissolved in DMSO to prepare stock solution (100 mM), which was diluted with physiological saline to the concentration of 100, 50 and 30 uM. Test compounds were administered by vitreous injection before 30 min of ischemia.

Adult rats were anaesthetized with ip (intra peritoneum) injection of chloral hydrate (400 mg/Kg), then the right eyes were treated with 1% tropicamide to dilate the pupils. The intraocular pressure (TO)P was raised to 160–180 mmHg, higher than normal blood pressure (140 mmHg), by cannulation of the anterior chamber connected to hydrostatic pressure device. Interruption of blood flow was confirmed ophtalmoscopically, the elevated IOP was maintained for 30 min. After 30 min of ischemia, both eyes were enucleated, and the retina was separated, of which cellular damage was observed. Number of cells in ganglion cell layer (250×25 um) and innernuclear layer (150×25 um) were counted, then calculated as a % of living cells compared to those of non-operated left eyes as a normal control. The results are given in table 10.

TABLE 10

Protective Effects on Ischemic Retinal cells

| | | Living cell (%) | |
|---|---|---|---|
| | | Ganglion Cell layer | Innernuclear layer |
| Normal control | | 100 | 100 |
| Ischemia | | 34.5 | 51.7 |
| Example 40 | 30 uM | 40.7 | 54.8 |
| | 50 uM | 60.2 | 69.8 |
| | 100 uM | 77.9 | 82.6 |

As seen in table 10, the compound of example 40 protected neurons both in ganglion and innernuclear layers after retinal ischemia, in a dose dependent manner.

With excellent protective effects to inhibit ischemic neuronal cell death in ganglion and innernuclear layers in retina, the compounds of the present invention can be used for the treatment of glaucoma, optical neuropathy, which may caused by ischemia.

Experimental Example 12

Effects on MNCV (Motor Nerve Conduction Velocity) in Diabetic Rats

In order to examine whether the compounds of the formula 1 improve impaired MNCV in diabetic rats, experiments were conducted as follows. Diabetes was induced with i.p. (intra peritoneum) injection of streptozocin (65 mg/Kg) in rats, then test compounds dissolved in 2 ml of media (physiological saline:ethanol:tween 80=8:1:1), were orally administered once a day. Rats were anesthetized with halothane, then the sciatic nerve was exposed to measure MNCV. The nerve was stimulated at two points. The first stimulus electrode was inserted at proximal end, and second stimulating electrode was inserted at the sciatic notch. The coaxial. needle electrode was inserted into interdigital muscle, then the muscle action potential induced by two point stimulation. The conduction velocity was calculated by dividing the distance between two stimulus points by the latency difference. Lipoic acid (100 mg/Kg) was used in comparison with the compound of formula 1 in recovery of impaired MNCV in diabectic rats. The recovery (%) of MNCV was calculated according to the following mathematical formula 4. The results are

[Mathematical formula 4]

$$\text{Recovery (\%)} = \frac{\text{MNCV of treated group} - \text{MNCV of diabetic rats}}{\text{MNCV of normal control} - \text{MNCV of diabetic rats}} \times 100$$

TABLE 11

Effects on MNCV in diabetic rats

|  | MNCV (sec) | Recovery (%) |
| --- | --- | --- |
| Normal control | 51.937 | 100 |
| Diabetic rat | 40.647 | — |
| Lipoic acid (100 mg/Kg) | 56.070 | 136.6 |
| Example 40 (30 mg/Kg) | 47.756 | 63.0 |

As seen in table 11, MNCV of diabetic rats were significantly decreased compared to that of normal control. Treatment of lipoic acid (100 mg/Kg) completely recovered impaired MNCV in diabetic rats. Administration of example 40 (30 mg/Kg) significantly improved MNCV in diabetic rats.

Experimental Example 13

Nociceptive Test (Hot Plate Test) in Diabetic Rats

In order to examine whether the compounds of the formula 1 improve impaired nociceptive responses in diabetic rats, experiments were conducted as follows.

Effects on nociceptive responses of test compounds in rats were examined using hat plate.

The same methods were applied for the induction of diabetes and treatment of test compound in rats. Rats were placed onto 50° C. hot plate, then latencies of nociceptive action such as licking were determined. The recovery (%) of nociceptive responses in diabetic rats was calculated according to the following mathematical formula 4. The results are given in table 12.

[Mathematical formula 5]

$$\text{Recovery (\%)} = \frac{\text{Response in treated group} - \text{Response in diabetic control}}{\text{Response in normal control} - \text{Response in diabetic control}} \times 100$$

TABLE 12

Effects on Nociceptive responses in Diabetic Rats

|  | Nociceptive response (sec) | Recovery (%) |
| --- | --- | --- |
| Normal control | 4.698 | 100 |
| Diabetic control | 3.986 | — |
| Lipoic acid | 4.371 | 60.2 |
| Example 40 | 4.791 | 106.5 |

As seen in table 12, Lipoic acid significantly improved impaired nociceptive responses in diabetic rats. On the contrary, the compound of example 40 completely recovered impaired nociceptive responses of diabetic rats in hot plate test.

With excellent improving activity against impaired MNCV and nociceptive responses of diabetic rats as seen in the above experimental example 12 and 13 as well as antioxidant and neuronal cell protection effects, the compounds of the present invention can be used for the prevention and treatment of diabetic neuropathy and diabetic peripheral disturbances.

Experimental Example 14

Protection Effects on Hypoxic Brain Injury

In order to examine whether the compounds of the formula 1 protect hypoxic brain injury in newborn rats, experiments were conducted as follows, using MRS (magnetic resonance spectrum).

Focal, hypoxic brain injury model in newborn rats are being most frequently used to study infant asphyxia, because whose maturity of brain is similar to that of human infant, and it is easy to get enough number of animals required for the determination of effects. It was reported that the lipid peak was increased in MRS (magnetic resonamce spectroscopy) by ischemic neuronal cell injury due to the destruction of cell membrane including blood-brain barrier [A. Bizzi et. al., Magnetic Resonance Imagin 14 581–592 (1996)], and also the concentration of lipid and apotosis are closely correlated to apotosis[Van der A. Toorn et al., Magnetic Resonance in Medicine, 36 , 914–922 (1996)]. N-Acetylaspartae (NAA) and creatine (Cr) are markers of neuronal coinS. Then it was confirmed that the value of lipid/NAA N-acetylaspartae) and lipid/Cr (creatine) are correlated with the morphological change and severity of apoptosis on hypoxic brain damage.

New born rats (within 7 days, 10–15 g) were placed in hypoxic chamber for 2 hr to induce hypoxia, and test compounds were intraperitoneally injected before 1 hr of hypoxia. Proton MPS was obtained at 1 day after brain injury, then the value of lipid/NAA and lipid/Cr were determined.

TABLE 13

Protective Effects on Hypoxic Brain Injury

|  | Lipid/NAA | Lipid/Cr |
| --- | --- | --- |
| Hypoxic control | 4.63 | 4.11 |
| Example 40 (50 mg/Kg) | 2.51 | 2.33 |

As seen in table 13, the compound of example 40 reduced the value of both Lipid/NAA and Lipid/Cr significantly, which represented protection effect on brain injury. With excellent protection effect on hypoxic brain injury in newborn rats, the compounds of the present invention can be used for the prevention and treatment of infant asphyxia.

Experimental Example 15

Inhibitory Effects on Proliferation of Vascular Smooth Muscle Cells

In order to examine whether the compounds of the formula 1 inhibit proliferation of vascular smooth muscle cells, experiments were conducted as follows.

Inhibitory effects on cell proliferation was evaluated by measurement of incorporation of [$^3$H]-thymidine into DNA. Rat aortic smooth muscle cells were grown in 24 well plate for 3 days to near confluence in DMEM containing 10% FBS, then DMEM containing FBS was washed out. Cells were cultured again in DMEM without serum for 48 hr to be quiescent. Test compounds were added 15 min before addition of angiotensin II (10-7M), which stimulate cell proliferation, then cells were incubated for 72 hr. During the last 4 hours of incubation, [$^3$H]-thymidine (1 uCi/ml) was added. Radioactive medium was removed and cells were washed 3 times with DMEM (3×1 ml) to remove non-incorporated isotopes, and treated with an aqueous solution of 15% TCA (trichloroacetic acid)for at least 2 hr followed by addition of an aqueous solution of 0.2 N NaOH (0.25 ml) for 30 min. The samples were filtered through glass microfiber filter (GF/B. Whatmann) under vacuum. After washing the filters 3 times with 2 ml of an aqueous solution of 5% TCA, the radioactivity incorporated into NA was counted by Liquid Scintilation Counter (Packard, TRI-CARB, 2100TR), then calculated incorporation % of [$^3$H]-thymidine. The results are given in table 14.

TABLE 14

Effects on [$^3$H]-thymidine incorporation (%) into DNA

| Compounds | Incorporation % |
| --- | --- |
| Angiotensin II | 100 |
| Example 7 | 37.8 |
| Example 5 | 53.6 |
| Example 2 | 59.0 |
| Example 14 | 60.0 |
| Example 22 | 64.0 |

As seen in table 14, compounds of example 2, 5, and 7 significantly inhibit the synthesis of DNA, representing below 60% of [$^3$H]-thymidine incorporation. Especially, the compound of example 7 represented 37.8% of low incorporation %.

With excellent inhibitory effect on proliferation of vascular smooth muscle cells, the compounds of the present invention can be used for the prevention and treatment of restenosis occurred after percutaneous coronary interventions of coronary artery occlusion.

Experimental Example 16

Acute Oral Toxicity Test in Rats

The test to confirm the toxicity of the compounds of formula 1 was carried out as follows.

In this test six-week old SPF SD rats were used with two rats assigned to each group. The compounds of examples 1, 2, 3, 5, 7, 8, 9, 10, 13, 14, 15, 19, 22, 23, 24, 25, 26, 28, 29, 30, 31, 32, 33, 34, 35, 36, 37, 38, 39, 40, 41, 44, 46, 47, 48, 49, 51, 52, 57, 58, 60, 62, 64, 67, 68, 69, 71 and 72 were suspended in 0.5% methyl cellulose, respectively, and administered orally at a single dose of 1 g/kg using a ball-tipped needle. The dosing volume was 10 ml/kg. After the administration, the animals were observed for clinical signs of toxicity or mortality and the body weight changes were measured. All survivors at the end of the observation period underwent laparotomy under ether anesthesia and the blood samples were taken from the abdominal aorta for hematological tests and biochemical analysis. After sacrificing the animals, autopsy was performed for macroscopic observation of the organs and tissues. Tissue samples of vital organs from macroscopic legion were removed and fixed in 10% neutral buffered formalin solution, then processed by standard procedures for histopathology and examined under light microscope. There were no significant changes in clinical symptoms, body weight and mortalities. Also in hematology, serum chemistry parameters and macroscopic observation, no drug-related changes were observed. As a result all the compounds tested did not show toxicity in rats up to a dose of 1 g/kg, and the lethal dose ($LD_{50}$) for oral administration was determined to be offer 1 g/kg in rats.

The present invention has been described in an illustrative manner, and it is to be understood that the terminology used is intended to be in the nature of description rather than of Imitation. Many modifications and variations of the present invention are possible in light of the above teachings. Therefore, it is to be understood that within the scope of the appended claims, the invention may be practiced otherwise than as specifically described.

What is claimed is:

1. Benzopyranyl guanidine derivatives represented by the following formula 1, their stereochemical isomers and their pharmaceutically acceptable salts

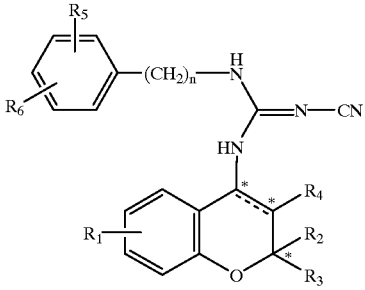

FORMULA 1 wherein $R_1$ represents H, halogen, $CF_3$, $NO_2$, CN, $OR^a$, $O(C=O)R^a$, $COOR^a$, $NH_2$, $NHS(O)_m R^a$, $NH(C=O)R^a$ or $S(O)_m R^a$; $R^a$ represents straight or branched alkyl group of $C_1$–$C_4$ or aryl group; and m is an integer of 0–2, $R_2$ represents straight or branched alkyl group of $C_1$–$C_4$,
$R_3$ represents $CH_2OR^a$,

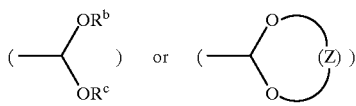

$R^a$ is defined as above; $R^b$ and $R^c$ are independent each other and represent straight or branched alkyl group of $C_1$–$C_4$, respectively; and Z represents straight or branched alkyl group of $C_1$–$C_5$, $R_4$ represents OH, H, halogen, $ONO_2$ or $O(C=O)R^a$; and $R^a$ is defined as above; $R_5$ and $R_6$ are independent each other and represent H, halogen, straight or branched alkyl group of $C_1$–$C_3$, $OR^a$, $CX_3$, $NO_2$, $CO_2R_a$, —(C=O)$R_a$ or $SO_3R^a$; $R^a$ is defined as above; and X represents halogen, and n is an integer of 0–2.

2. The benzopyranyl guanridine derivatives, their stereochemical isomers and their pharmaceutically acceptable salts according to claim 1, wherein $R_1$ represents $NO_2$, CN, $NH_2$ or $S(O)_mR^a$; $R^a$ represents straight or branched alkyl group of $C_1$–$C_2$, aryl group; and m is an integer of 0–2, $R_2$ represents $CH_3$, $R_3$ represents

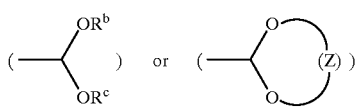

$R^b$ and $R^c$ are independent each other and represent straight or branched alkyl group of $C_1$–$C_3$, respectively; and Z represents straight or branched alkyl group of $C_1$–$C_5$, $R_4$ represents OH, H or —O(C=O)$R^a$; and $R^a$ represents straight or branched alkyl group of $C_1$–$C_3$;

$R_5$ and $R_6$ are independent each other and represent halogen straight or branched alkyl group of $C_1$–$C_3$, $OR^a$, $CX_3$ or $NO_2$; $R^a$ represents straight or branched alkyl group of $C_1$–$C_3$; and X represents halogen, and n is an integer of 0–2.

3. The benzopyranyl guanidine derivatives, their stereochemical isomers and their pharmaceutically acceptable salts according to claim 1, wherein the compound of formula 1 is selected from the group consisting of:

1) (2R,3R,4S)-N"-cyano-N-(6-nitro-3,4-dihydro-3-hydroxy-2-methyl-2-dlmethoxymethyl-2H-benzopyran-4-yl)-N'-(4-chlorophenyl)guanidine;

2) (2R,3S,4R)-N"-cyano-N-(6-nitro-3,4-dihydro-3-hydroxy-2-methyl-2-dimethoxymethyl-2H-benzopyran-4-yl)-N'-(4-chlorophenyl)guanidine;

3) (2R,3R,4S)-N"-cyano-N-(6-nitro-3,4-dihydro-3-hydroxy-2-methyl-2-dimethoxymethyl-2H-benzopyran-4-yl)-N'-(3-chlorophenyl)guanidine;

4) (2R,3S,4R)-N"-cyano-N-(6-nitro-3,4-dihydro-3-hydroxy-2-methyl-2-dimethoxymethyl-2H-benzopyran-4-yl)-N'-(3-chlorophenyl)guanidine;

5) (2R,3R,4S)-N"-cyano-N-(6-nitro-3,4-dihydro-3-hydroxy-2-methyl-2-dimethoxymethyl-2H-benzopyran-4-yl)-N'-(4-nitrophenyl)guanidine;

6) (2R,3R,4S)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;

7) (2R,3S,4R)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;

8) (2R,3R,4S)-N"-cyano-N-(6-nitro-3,4-dihydro-3-hydroxy-2-methyl-2-dimethoxymethyl-2H-benzopyran-4-yl)-N'-(4-methoxyphenyl)guanidine;

9) (2R,3S,4R)-N"-cyano-N-(6-nitro-3,4-dihydro-3-hydroxy-$^2$-methyl-2-dimethoxymethyl-2H-benzopyran-4-yl)-N'-(4-methoxyphenyl)guanidine;

10) (2S,3R,4S)-N"-cyano-N-(6-nitro-3,4-dihydro-3-hydroxy-2-methyl-2-dimethoxymethyl-2H-benzopyran-4-yl)-N'-(4-chlorophenyl)guanidine;

11) (2S,3S,4R)-N"-cyano-N-(6-nitro-3,4-dihydro-3-hydroxy-2-methyl-2-dimethoxymethyl-2H-benzopyran-4-yl)-N'-(4-chlorophenyl)guanidine;

12) (2S,3R, $^4$S)-N"-cyano-N-(6-nitro-3,4-dihydro-3-hydroxy-2-methyl -2-dimethoxymethyl-2H-benzopyran-4-yl)-N'-(3-chlorophenyl)guanidine;

13) (2S,3S,4R)-N"-cyano-N-(6-nitro-3,4-dihydro-3-hydroxy-2-methyl-2-dimethoxymethyl -2H-benzopyran-4-yl)-N'-(3-chlorophenyl)guanidine;

14) (2S,3R,4S)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;

15) (2S,3S,4R)-N"-cyano-N-(6-nitro-3,4-dihydro-3-hydroxy-2-methyl-2-dimethoxymethyl-2H-benzopyran-4-yl)-N'-(3-trifluoromethylphenyl)guanidine;

16) (2S,3R,4S)-N"-cyano-N-(6-nitro-3,4-dihydro-3-hydroxy-2-methyl-2-dimethoxymethyl-2H-benzopyran-4-yl)-N'-(4-methoxyphenyl)guanidine;

17) (2S,3S,4R)-N"-cyano-N-(6-nitro-3,4-dihydro-3-hydroxy-2-methyl-2-dimethoxymethyl-2H-benzopyran-4-yl)-N'-(4-methoxyphenyl)guanidine;

18) (2R,3R,4S)-N"-cyano-N-(6-nitro-3,4-dihydro-3-hydroxy-2-methyl-2-dimethoxymethyl-2H-benzopyran-4-yl)-N'-(4-methylphenyl)guanidine;

19) (2R,3S,4R)-N"-cyano-N-(6-nitro-3,4-dihydro-3-hydroxy-2-methyl-2-dimethoxymethyl-2H-benzopyran-4-yl)-N'-(4-methylphenyl)guanidine;

20) (2R,3R,4S)-N"-cyano-N-(6-nitro-3,4-dihydro-3-hydroxy-2-methyl-2-dimethoxymethyl-2H-benzopyran-4-yl)-N'-(4-methoxybenzyl)guanidine;

21) (2R,3S,4R)-N"-cyano-N-(6-nitro-3,4-dihydro-3-hydroxy-2-methyl -2-dimethoxymethyl-2H-benzopyran-4-yl)-N'-(4-methoxybenzyl)guanidine;

22 (2R,3R,4S)-N"-cyano-N-(6-nitro-3,4-dihydro-3-hydroxy-2-methyl-2-dimethoxymethyl-2H-benzopyran-4-yl)-N'-benzylguanidine;

23) (2R,3S,4R)-N"-cyano-N-(6-nitro-3,4-dihydro-3-hydroxy-2-methyl-2-dimethoxymethyl-2H-benzopyran-4-yl)-N'-benzylguanidine;

24) (2S,3R,4S)-N"-cyano-N-(6-nitro-3,4-dihydro-3-hydroxy-2-methyl-2-dimethoxymethyl-2H-benzopyran-4-yl-N'-benzylguanidine;

25) (2S,3S,4R)-N"-cyano-N-(6-nitro-3,4-dihydro-3-hydroxy-2-methyl-2-dimethoxymethyl-2H-benzopyran-4-yl)-N'-benzylguanidine;

26) (2R,3R,4S)-N"-(cyano-N-(3,4-dihydro-3-hydroxy-2-methyl-2-dimethoxymethyl-2H-benzopyran-4-yl)-N'-(4-chlorophenyl)guanidine;

27) (2R,3S,4R)-N"-cyano-N-(3,4-dihydro-3-hydroxy-2-methyl-2-dimethoxymethyl-2H-benzopyran-4-yl)-N'-(4-chlorophenyl)guanidine;

28) (2R,3R,4S)-N"-cyano-N-(6-nitro-3,4-dihydro-3-hydroxy-2-methyl-2-hydroxymethyl-2H-benzopyran-4-yl)-N'-4-chlorophenyl)guanidine;

29) (2R,3S,4R)-N"-cyano-N-(6-nitro-3,4-dihydro-3-hydroxy-2-methyl-2-hydroxymethyl-2H-benzopyran-4-yl)-N'-4-chlorophenyl)guanidine;

30) (2R,3R,4S)-N"-cyano-N-(6-nitro-3,4-dihydro-3-hydroxy-2-methyl-2-methoxymethyl-2H-benzopyran-4-yl)-N'-(4-chlorophenyl)guanidine;
31) (2R,3S,4R)-N"-cyano-N-(6-nitro-3,4-dihydro-3-hydroxy-2-methyl-2-methoxymethyl-2H-benzopyran-4-yl)-N'-(4-chlorophenyl)guanidine;
32) (2S,3R,4S)-N"-cyano-N-(6-nitro-3,4-dihydro-3-hydroxy-2-methyl-2-dimethoxymethyl-2H-benzopyran-4-yl)-N'-(2-chlorophenyl)guanidine;
33) (2S,3S,4R)-N"-cyano-N-(6-nitro-3,4-dihydro-3-hydroxy-2-methyl-2-dimethoxymethyl-2H-benzopyran-4-yl)-N'-(2-chlorophenyl)guanidine;
34) (2S,3R,4S)-N"-cyano-N-(6-nitro-3,4-dihydro-3-hydroxy-2-methyl-2-dimethoxymethyl-2H-benzopyran-4-yl)-N'-(2-trifluoromethylphenyl)guanidine;
35) (2S,3S,4R)-N"-cyano-N-(6-nitro-3,4-dihydro-3-hydroxy-2-methyl-2-dimethoxymethyl-2H-benzopyran-4-yl)-N'-(2-trifluoromethylphenyl)guanidine;
36) (2S,3R,4S)-N"-cyano-N-(6-nitro-3,4-dihydro-3-hydroxy-2-methyl-2-dimethoxymethyl-2H-benzopyran-4-yl)-N'-(2-chlorobenzyl)guanidine;
37) (2S,3S,4R)-N"-cyano-N-(6-nitro-3,4-dihydro-3-hydroxy-2-methyl-2-dimethoxymethyl-2H-benzopyran-4-yl)-N'-(2-chlorobenzyl)guanidine;
38) (2S,3S,4R)-N"-cyano-N-(6-nitro-3,4-dihydro-3-acetoxy-2-methyl-2-dimethoxymethyl-2H-benzopyran-4-yl)-N'-benzylguanidine;
39) (2S)-N"-cyano-N-(6-nitro-2-methyl-2-dimethoxymethyl-2H-benzopyran-4-yl)-N'-benzylguanidine;
40) (2S,3S,4R)-N"-cyano-N-(6-nitro-3,4-dihydro-3-hydroxy-2-methyl-2-dimethoxymethyl-2H-benzopyran-4-yl)-N'-benzylguanidine;
41) (2S,3S,4R)-N"-cyano-N-(6-acetoxyamino-3,4-dihydro-3-hydroxy-2-methyl-2-dimethoxymethyl-2H-benzopyran-4-yl)-N'-benzylguanidine;
42) (2S,3S,4R)-N"-cyano-N-(6-methanesulfonylamino-3,4-dihydro-3-hydroxy-2-methyl-2-dimethoxymethyl-2H-benzopyran-4-yl)-N'-benzylguanidine;
43) (2S,3S,4R)-N"-cyano-N-(6-cyano-3,4-dihydro-3-hydroxy-2-methyl-2-dimethoxymethyl-2H-benzopyran-4-yl)-N'-(4-chlorophenyl)guanidine;
44) (2S,3R,4S)-N"-cyano-N-(6-cyano-3,4-dihydro-3-hydroxy-2-methyl-2-dimethoxymethyl-2H-benzopyran-4-yl)-N'-(4-chlorophenyl)guanidine;
45) (2S,3S,4R)-N"-cyano-N-(6-nitro-3,4-dihydro-3-hydroxy-2-methyl-2-dimethoxymethyl-2H-benzopyran-4-yl)-N'-benzylguanidine;
46) (2S,3R,4S)-N"-cyano-N-(6-cyano-3,4-dihydro-3-hydroxy-2-methyl-2-2-dimethoxymethyl2H-benzopyran-4-yl)-N'-benzylguanidine;
47) (2S,3S,4R)-N"-cyano-N-(6-bromo-3,4-dihydro-3-hydroxy-2-methyl-2-2-dimethoxymethyl-2H-benzopyran-4-yl)-N'-benzylguanidine;
48) (2S,3S,4R)-N"-cyano-N-(6-nitro-3,4-dihydro-3-hydroxy-2-methyl-2-2-dimethoxymethyl-2H-benzopyran-4-yl)-N'-(3,4-dimethoxybenzyl)guanidine;
49) (2S,3S,4R)-N"-cyano-N-(6-amino-3,4-dihydro-3-hydroxy-2-methyl-2-dimethoxymethyl-2H-benzopyran-4-yl)-N'-(3,4-dimethoxybenzyl)guanidine;
50) (2S,3S,4R)-N"-cyano-N-(6-nitro-3,4-dihydro-3-hydroxy-2-methyl-2-dimethoxymethyl-2H-benzopyran-4-yl)-N'-(4-methoxybenzyl)guanidine;
51) (2S,3S,4R)-N"-cyano-N-(6-amino-3,4-dihydro-3-hydroxy-2-methyl-2-dimethoxymethyl-2H-benzopyran-4-yl)-N'-(4-methoxybenzyl)guanidine;
52) (2S,3S,4R)-N"-cyano-N-(6-nitro-3,4-dihydro-3-hydroxy-2-methyl-2-dimethoxymethyl-2H-benzopyran-4-yl)-N'-(3-nitrobenzyl)guanidine;
53) (2S,3S,4R)-N"-cyano-N-(6-nitro-3,4-dihydro-3-hydroxy-2-methyl-2-dimethoxymethyl-2H-benzopyran-4-yl)-N'-(3-trifluoromethylbenzyl)guanidine;
54) (2S,3S,4R)-N"-cyano-N-(6-amino-3,4-dihydro-3-hydroxy-2-methyl-2-dimethoxymethyl-2H-benzopyran-4-yl)-N'-(3-trifluoromethylbenzyl)guanidine;
55) (2S,3S,4R)-N"-cyano-N-(6-methanesulfonyloxy-3,4-dihydro-3-hydroxy-2-methyl-2-dimethoxymethyl-2H-benzopyran-4-yl)-N'-benzylguanidine;
56) (2R,3S,4R)-N"-cyano-N-(6-methanesulfonyloxy-3,4-dihydro-3-hydroxy-2-methyl-2-dimethoxymethyl-2H-benzopyran-4-yl)-N'-benzylguanidine;
57) (2S,3R,4S)-N"-cyano-N-(6-amino-3,4-dihydro-3-hydroxy-2-methyl-2-dimethoxymethyl-2H-benzopyran-4-yl)-N'-benzylguanidine;
58) (2R,3R,4S)-N"-cyano-N-(6-amino-3,4-dihydro-3-hydroxy-2-methyl-2-dimethoxymethyl-2H-benzopyran-4-yl)-N'-benzylguanidine;
59) (2R,3S,4R)-N"-cyano-N-(6-amino-3,4-dihydro-3-hydroxy-2-methyl-2-dimethoxymethyl-2H-benzopyran-4-yl)-N'-(benzylguanidine;
60) (2S,3S,4R)-N"-cyano-N-(6-nitro-3,4-dihydro-3-hydroxy-2-methyl-2-([1,3]dioxolan-2-yl)-2H-benzopyran-4-yl)-N'-benzylguanidine;
61) (2S,3S,4R)-N"-cyano-N-(6-amino-3,4-dihydro-3-hydroxy-2-methyl-2-([1,3]dioxolan-2-yl)-2H-benzopyran-4-yl)-N'-benzylguanidine;
62) (2S,3S,4R)-N"-cyano-N-(6-nitro-3,4-dihydro-3-hydroxy-2-methyl-2-([1,3]dioxan-2-yl)-2H-benzopyran-4-yl)-N'-benzylguanidine;
63) (2S,3S,4R)-N"-cyano-N-(6-amino-3,4-dihydro-3-hydroxy-2-methyl-2-([1,3]dioxan-2-yl)-2H-benzopyran-4-yl)-N'-benzylguanidine;
64) (2S,3S,4R)-N"-cyano-N-(6-nitro-3,4-dihydro-3-hydroxy-2-methyl-2-([1,3]-5,5-dimethyldioxan-2-yl)-2H-benzopyran-4yl)-N'(benzylguanidine;
65) (2S,3S,4R)-N"-cyano-N-(6-amino-3,4-dihydro-3-hydroxy-2-methyl-2-([1,3]-5,5-dimethyldioxan-2-yl)-2H-benzopyran-4-yl)-N'-benzylguanidine;
66) (2S,3S,4R)-N"-cyano-N-(6-nitro-3,4-dihydro-3-hydroxy-2-methyl-2-diethoxymethyl-2H-benzopyran-4-yl)-N'-benzylguanidine;
67) (2S,3S,4R)-N"-cyano-N-(6-amino-3,4-dihydro-3-hydroxy-2-methyl-2-diethoxymethyl-2H-benzopyran-4-yl)-N'-benzylguanidine;
68) (2S,3S,4R)-N"-cyano-N-(6-methoxycarbonyl-3,4-dihydro-3-hydroxy-2-methyl-2-dimethoxymethyl-2H-benzopyran-4-yl)-N'-benzylguanidine;
69) (2S,3S,4R)-N"-cyano-N-(6-methoxycarbonyl-3,4-dihydro-3-hydroxy-2-methyl-2-dimethoxymethyl-2H-benzopyran-4-yl)-N'-benzylguanidine;
70) (3S,4R)-N"-cyano-N-(8-nitro-3,4-dihydro-3-hydroxy-2-methyl-2-dimethoxymethyl-2H-benzopyran-4-yl)-N'-benzylguanidine;
71) (2S,3S,4R)-N"-cyano-N-(8-amino-3,4-dihydro-3-hydroxy-2-methyl-2-dimethoxymethyl-2H-benzopyran-4-yl)-N'-benzylguanidine; and
72) (2R,3S,4R)-N"-cyano-N-(8-amino-3,4-dihydro-3-hydroxy-2-methyl-2-dimethoxymethyl-2H-benzopyran-4-yl)-N'-benzylguanidine.

4. A process for preparing the benzopyranyl guanidine derivatives of claim 1, comprising the step of reacting an aminoalcohol compound (III) and a thiourea compound (IV) in the presence of a condensing agent to obtain a compound (I').

5. The process according to claim 4, wherein the condensing agent is selected from the group consisting of water-soluble carbodiimide-type condensing agents comprising 1-[3-(dimethylamino)propyl]-3-ethylcarbodiimide hydrochloride, and N,N'-dicyclohexylcarbodiimide.

6. The process according to claim 4, wherein the reaction solvent is selected from the group consisting of methylene chloride, chloroform, dimethylfomamide and dimethylsulfoxide.

7. A process for preparing of the benzopyranyl guanidine derivatives of claim 1, which comprises the steps of:

1) reacting an aminoalcohol compound (III) and diphenyl cyanocarbonimidate (X) in the presence of a base to prepare a compound (V) (step 1); and 2) reacting the compound (V) and an amine compound (VI) to prepare the compound (I') (step 2).

8. The process according to claim 7, wherein the base of step 1 is selected from tertiary amines comprising triethylamine, N,N-diisopropylethylamine, pyridine, 1,8-diazabicyclo[5.4.0]undec-7-ene and 4-(dimethylamino) pyridine.

9. The process according to claim 7, wherein the reaction solvent of step 1 or step 2 is selected from the group consisting of alcohols comprising ethanol and isopropanol; dimethylformamide; dimethylsulfoxide; and chloroform.

10. Pharmaceutical compositions for protecting the heart which pharmacologically prevent and treat of myocardial infarction and congestive heart failure and angina pectoris, which contain the benzopyranyl guanidine derivatives of claim 1 or their pharmaceutical acceptable salts as an active ingredient.

11. Pharmaceutical compositions for suppressing lipid peroxidation, which contain the benzopyranyl guanidine derivatives of claim 1 or their pharmaceutical acceptable salts as an active ingredient.

12. Pharmaceutical compositions which pharmacologically inhibit NO generation, which contain the benzopyranyl guanidine derivatives of claim 1 or their pharmaceutical acceptable salts as an active ingredient.

13. Pharmaceutical compositions for protecting brain injury due to brain ischemia-reperfusion, which contain the benzopyranyl guanidine derivatives of claim 1 or their pharmaceutical acceptable salts as an active ingredient.

14. pharmaceutical compositions which pharmacologically treat and diabetic retinopathy by suppressing angiogenesis, which contain the benzopyranyl guanidine derivatives of claim 1 or their pharmaceutical acceptable salts as an active ingredient.

15. Pharmaceutical compositions which pharmacologically prevent and treat neurodegenerative diseases selected from the group consisting of Alzheimer's disease and senile dementia, and atherosclerosis by suppressing lipid peroxidation and reactive oxygen species, which contain the benzopyranyl guanidine derivatives of claim 1 or their pharmaceutical acceptable salts as an active ingredient.

16. Pharmaceutical compositions which pharmacologically prevent and treat infant asphyxia, glaucoma, diabetic neuropathy and head trauma by protecting neuronal cells, which contain the benzopyranyl guanidine derivatives of claim 1 or their pharmaceutical acceptable salts as an active ingredient.

17. Pharmaceutical compositions which pharmacologically prevent and treat restenosis by suppressing cell proliferation, which contain the benzopyranyl guanidine derivatives of claim 1 or their pharmaceutical acceptable salts as an active ingredient.

18. Pharmaceutical compositions protect and preserve organs selected from a group consisting of heart, kidney, liver and tissues, and for protecting organs in major cardiovascular surgery, which contain the benzypyranyl guanidine derivatives of claim 1 or their pharmaceutical acceptable salts as an active ingredient.

* * * * *